US011020231B2

(12) United States Patent
Axelrod et al.

(10) Patent No.: US 11,020,231 B2
(45) Date of Patent: *Jun. 1, 2021

(54) TOOLING FOR CREATING TAPERED OPENING IN TISSUE AND RELATED METHODS

(71) Applicant: Cartiva, Inc., Alpharetta, GA (US)

(72) Inventors: Michael A. Axelrod, Roswell, GA (US); Letitia Tudor, Suwanee, GA (US)

(73) Assignee: CARTIVA, INC., Alpharetta, GA (US)

( * ) Notice: Subject to any disclaimer, the term of this patent is extended or adjusted under 35 U.S.C. 154(b) by 16 days.

This patent is subject to a terminal disclaimer.

(21) Appl. No.: 16/438,689

(22) Filed: Jun. 12, 2019

(65) Prior Publication Data

US 2019/0290437 A1    Sep. 26, 2019

Related U.S. Application Data

(62) Division of application No. 15/098,265, filed on Apr. 13, 2016, now Pat. No. 10,350,072.
(Continued)

(51) Int. Cl.
*A61F 2/48* (2006.01)
*A61F 2/46* (2006.01)
(Continued)

(52) U.S. Cl.
CPC .......... *A61F 2/30734* (2013.01); *A61B 17/16* (2013.01); *A61F 2/3094* (2013.01);
(Continued)

(58) Field of Classification Search
CPC ...... A61F 2/4611; A61F 2/4455; A61F 2/447; A61F 2/442; A61F 2002/30593;
(Continued)

(56) References Cited

U.S. PATENT DOCUMENTS 3,276,996 A    10/1966 Lazare
3,663,470 A    5/1972 Nishimura et al.
(Continued)

FOREIGN PATENT DOCUMENTS

DE    20218703 U1    3/2003
EP    0222404 A1    5/1987
(Continued)

OTHER PUBLICATIONS

Andrade et al., "Water as a Biomaterial," Trans. Am. Soc. Artif. Intern. Organs, 19:1 (1973).
(Continued)

*Primary Examiner* — Ann Schillinger
(74) *Attorney, Agent, or Firm* — Duane Morris LLP

(57) ABSTRACT

According to some embodiments, a method of creating for creating a reverse tapered opening within tissue comprises creating a cylindrical opening within a targeted anatomical site of a subject using a first device and removing additional tissue from the sidewalls of the cylindrical opening using a cutting member to create a reverse tapered opening within the targeted anatomical site using a second device, wherein, once the reverse tapered opening is created, a diameter or other cross-sectional dimension of a bottom surface of the opening is larger than a diameter or other cross-sectional dimension of a top surface of the opening.

15 Claims, 31 Drawing Sheets

Related U.S. Application Data

(60) Provisional application No. 62/147,548, filed on Apr. 14, 2015.

(51) Int. Cl.
    *A61F 2/30*     (2006.01)
    *A61B 17/16*     (2006.01)
    *A61B 17/56*     (2006.01)

(52) U.S. Cl.
    CPC ........ *A61F 2/30756* (2013.01); *A61F 2/4618* (2013.01); *A61B 17/1617* (2013.01); *A61B 2017/564* (2013.01); *A61F 2002/30075* (2013.01); *A61F 2002/30205* (2013.01); *A61F 2002/30677* (2013.01)

(58) Field of Classification Search
    CPC ............. A61F 2002/30841; A61F 2/28; A61F 2002/30622; A61F 2002/2835; A61F 2310/00359; A61F 2002/3023; A61F 2002/30266; A61F 2002/30281; A61F 2002/30372; A61F 2002/30373; A61B 17/155; A61B 17/1664; A61B 17/1764; A61B 17/7037; A61B 17/7056; A61B 2017/0256; A61B 17/157; A61B 17/1604; A61B 17/3421; A61B 2017/564; A61B 2017/681; A61B 2034/102
    See application file for complete search history.

(56) References Cited

U.S. PATENT DOCUMENTS

| | | | |
|---|---|---|---|
| 3,673,612 | A | 7/1972 | Merrill et al. |
| 3,849,238 | A | 11/1974 | Gould et al. |
| 3,859,421 | A | 1/1975 | Hucke |
| 4,083,906 | A | 4/1978 | Schindler et al. |
| 4,158,684 | A | 6/1979 | Klawitter et al. |
| 4,205,400 | A | 6/1980 | Shen et al. |
| 4,351,069 | A | 9/1982 | Ballintyn et al. |
| 4,472,542 | A | 9/1984 | Nambu |
| 4,517,295 | A | 5/1985 | Bracke et al. |
| 4,524,064 | A | 6/1985 | Nambu |
| 4,609,337 | A | 9/1986 | Wichterle et al. |
| 4,663,358 | A | 5/1987 | Hyon et al. |
| 4,664,857 | A | 5/1987 | Nambu |
| 4,693,939 | A | 9/1987 | Ofstead |
| 4,731,081 | A | 3/1988 | Tiffany et al. |
| 4,734,097 | A | 3/1988 | Tanabe et al. |
| 4,738,255 | A | 4/1988 | Goble et al. |
| 4,753,761 | A | 6/1988 | Suzuki |
| 4,759,766 | A | 7/1988 | Buttner-Janz et al. |
| 4,772,284 | A | 9/1988 | Suzuki |
| 4,784,990 | A | 11/1988 | Nimrod et al. |
| 4,787,905 | A | 11/1988 | Loi |
| 4,808,353 | A | 2/1989 | Nambu et al. |
| 4,828,493 | A | 5/1989 | Nambu et al. |
| 4,851,168 | A | 7/1989 | Graiver et al. |
| 4,911,720 | A | 3/1990 | Collier |
| 4,916,170 | A | 4/1990 | Nambu |
| 4,946,561 | A | 8/1990 | Fischer |
| 4,988,761 | A | 1/1991 | Ikada et al. |
| 4,995,882 | A | 2/1991 | Destouet et al. |
| 5,047,055 | A | 9/1991 | Bao et al. |
| 5,080,674 | A | 1/1992 | Jacobs et al. |
| 5,095,037 | A | 3/1992 | Iwamitsu et al. |
| 5,106,743 | A | 4/1992 | Franzblau et al. |
| 5,106,876 | A | 4/1992 | Kawamura |
| 5,108,428 | A | 4/1992 | Capecchi et al. |
| 5,108,436 | A | 4/1992 | Chu et al. |
| 5,118,667 | A | 6/1992 | Adams et al. |
| 5,141,973 | A | 8/1992 | Kobayashi et al. |
| 5,171,322 | A | 12/1992 | Kenny |
| 5,171,574 | A | 12/1992 | Kuberasampath et al. |
| 5,192,326 | A | 3/1993 | Bao et al. |
| 5,206,023 | A | 4/1993 | Hunziker |
| 5,219,360 | A | 6/1993 | Georgiade |
| 5,234,456 | A | 8/1993 | Silvestrini |
| 5,244,799 | A | 9/1993 | Anderson |
| 5,258,023 | A | 11/1993 | Reger |
| 5,258,042 | A | 11/1993 | Mehta |
| 5,258,043 | A | 11/1993 | Stone |
| 5,260,066 | A | 11/1993 | Wood et al. |
| 5,287,857 | A | 2/1994 | Mann |
| 5,288,503 | A | 2/1994 | Wood et al. |
| 5,290,494 | A | 3/1994 | Coombes et al. |
| 5,314,477 | A | 5/1994 | Marnay |
| 5,314,478 | A | 5/1994 | Oka et al. |
| 5,326,364 | A | 7/1994 | Clift, Jr. et al. |
| 5,336,551 | A | 8/1994 | Gravier et al. |
| 5,336,767 | A | 8/1994 | Della Valle et al. |
| 5,343,877 | A | 9/1994 | Park |
| 5,344,459 | A | 9/1994 | Swartz |
| 5,346,935 | A | 9/1994 | Suzuki et al. |
| 5,397,572 | A | 3/1995 | Coombes et al. |
| 5,399,591 | A | 3/1995 | Smith et al. |
| 5,401,269 | A | 3/1995 | Buttner-Janz et al. |
| 5,409,904 | A | 4/1995 | Hecht et al. |
| 5,410,016 | A | 4/1995 | Hubbell et al. |
| 5,442,053 | A | 8/1995 | Della Valle et al. |
| 5,458,643 | A | 10/1995 | Oka et al. |
| 5,458,645 | A | 10/1995 | Bertin |
| 5,486,197 | A | 1/1996 | Le et al. |
| 5,489,310 | A | 2/1996 | Mikhail |
| 5,490,962 | A | 2/1996 | Cima et al. |
| 5,492,697 | A | 2/1996 | Boyan et al. |
| 5,494,940 | A | 2/1996 | Unger et al. |
| 5,502,082 | A | 3/1996 | Unger et al. |
| 5,512,475 | A | 4/1996 | Naughton et al. |
| 5,522,898 | A | 6/1996 | Bao |
| 5,534,028 | A | 7/1996 | Bao et al. |
| 5,541,234 | A | 7/1996 | Unger et al. |
| 5,545,229 | A | 8/1996 | Parsons et al. |
| 5,556,429 | A | 9/1996 | Felt |
| 5,556,431 | A | 9/1996 | Buttner-Janz |
| 5,578,217 | A | 11/1996 | Unger et al. |
| 5,601,562 | A | 2/1997 | Wolf et al. |
| 5,626,861 | A | 5/1997 | Laurencin et al. |
| 5,645,592 | A | 7/1997 | Nicolais et al. |
| 5,656,450 | A | 8/1997 | Boyan et al. |
| 5,658,329 | A | 8/1997 | Purkait |
| 5,674,241 | A | 10/1997 | Bley et al. |
| 5,674,295 | A | 10/1997 | Ray et al. |
| 5,674,296 | A | 10/1997 | Bryan et al. |
| 5,688,459 | A | 11/1997 | Mao et al. |
| 5,700,289 | A | 12/1997 | Breitbart et al. |
| 5,705,780 | A | 1/1998 | Bao |
| 5,716,416 | A | 2/1998 | Lin |
| 5,750,585 | A | 5/1998 | Park et al. |
| 5,766,618 | A | 6/1998 | Laurencin et al. |
| 5,769,897 | A | 6/1998 | Harle |
| 5,769,899 | A | 6/1998 | Schwartz et al. |
| 5,789,464 | A | 8/1998 | Muller |
| 5,795,353 | A | 8/1998 | Felt |
| 5,824,093 | A | 10/1998 | Ray et al. |
| 5,824,094 | A | 10/1998 | Serhan et al. |
| 5,844,016 | A | 12/1998 | Sawhney et al. |
| 5,847,046 | A | 12/1998 | Jiang et al. |
| 5,855,610 | A | 1/1999 | Vacanti et al. |
| 5,863,297 | A | 1/1999 | Walter et al. |
| 5,863,551 | A | 1/1999 | Woerly |
| 5,876,452 | A | 3/1999 | Anthanasiou et al. |
| 5,876,741 | A | 3/1999 | Ron |
| 5,880,216 | A | 3/1999 | Tanihara et al. |
| 5,882,351 | A | 3/1999 | Fox |
| 5,900,245 | A | 5/1999 | Sawhney et al. |
| 5,916,585 | A | 6/1999 | Cook et al. |
| 5,925,626 | A | 7/1999 | Della Valle et al. |
| 5,928,239 | A | 7/1999 | Mirza |
| 5,935,129 | A | 8/1999 | McDevitt et al. |
| 5,944,754 | A | 8/1999 | Vacanti |
| 5,947,844 | A | 9/1999 | Shimosaka et al. |
| 5,948,829 | A | 9/1999 | Wallajapet et al. |
| 5,957,787 | A | 9/1999 | Hwang |

(56) References Cited

U.S. PATENT DOCUMENTS

| | | |
|---|---|---|
| 5,976,186 A | 11/1999 | Bao et al. |
| 5,981,826 A | 11/1999 | Ku et al. |
| 6,001,352 A | 12/1999 | Boyan et al. |
| 6,027,744 A | 2/2000 | Vacanti et al. |
| 6,060,534 A | 5/2000 | Ronan et al. |
| 6,093,205 A | 7/2000 | McLeod et al. |
| 6,102,954 A | 8/2000 | Albrektsson et al. |
| 6,103,255 A | 8/2000 | Levene et al. |
| 6,132,465 A | 10/2000 | Ray et al. |
| 6,156,067 A | 12/2000 | Bryan et al. |
| 6,171,610 B1 | 1/2001 | Vacanti et al. |
| 6,187,329 B1 | 2/2001 | Agrawal et al. |
| 6,206,927 B1 | 3/2001 | Fell |
| 6,224,630 B1 | 5/2001 | Bao et al. |
| 6,231,605 B1 | 5/2001 | Ku |
| 6,245,026 B1 | 6/2001 | Campbell |
| 6,255,359 B1 | 7/2001 | Agrawal et al. |
| 6,264,695 B1 | 7/2001 | Stoy |
| 6,268,405 B1 | 7/2001 | Yao et al. |
| 6,271,278 B1 | 8/2001 | Park et al. |
| 6,280,475 B1 | 8/2001 | Bao et al. |
| 6,334,044 B1 | 12/2001 | Wasai et al. |
| 6,337,198 B1 | 1/2002 | Levene et al. |
| 6,340,369 B1 | 1/2002 | Ferree |
| 6,341,952 B2 | 1/2002 | Gayla et al. |
| 6,344,058 B1 | 2/2002 | Ferree |
| 6,355,699 B1 | 3/2002 | Vyakarnam et al. |
| 6,358,251 B1 | 3/2002 | Mirza |
| 6,371,984 B1 | 4/2002 | Van Dyke et al. |
| 6,376,573 B1 | 4/2002 | White et al. |
| 6,379,962 B1 | 4/2002 | Holy et al. |
| 6,383,519 B1 | 5/2002 | Sapieszko et al. |
| 6,402,784 B1 | 6/2002 | Wardlaw |
| 6,402,785 B1 | 6/2002 | Zdeblick et al. |
| 6,419,704 B1 | 7/2002 | Ferree |
| 6,428,576 B1 | 8/2002 | Haldimann |
| 6,451,059 B1 | 9/2002 | Janas et al. |
| 6,472,210 B1 | 10/2002 | Holy et al. |
| 6,482,234 B1 | 11/2002 | Weber et al. |
| 6,531,523 B1 | 3/2003 | Davankov et al. |
| 6,533,818 B1 | 3/2003 | Weber et al. |
| 6,534,084 B1 | 3/2003 | Vyakarnam et al. |
| 6,558,421 B1 | 5/2003 | Fell et al. |
| 6,602,291 B1 | 8/2003 | Ray et al. |
| 6,607,558 B2 | 8/2003 | Kuras |
| 6,610,094 B2 | 8/2003 | Husson |
| 6,629,997 B2 | 10/2003 | Mansmann |
| 6,645,248 B2 | 11/2003 | Casutt |
| 6,667,049 B2 | 12/2003 | Janas et al. |
| 6,679,917 B2 | 1/2004 | Ek |
| 6,686,437 B2 | 2/2004 | Buchman et al. |
| 6,707,558 B2 | 3/2004 | Bennett |
| 6,710,126 B1 | 3/2004 | Hirt et al. |
| 6,726,721 B2 | 4/2004 | Stoy et al. |
| 6,733,533 B1 | 5/2004 | Lozier |
| 6,734,000 B2 | 5/2004 | Chin et al. |
| 6,740,118 B2 | 5/2004 | Eisermann et al. |
| 6,773,713 B2 | 8/2004 | Bonassar et al. |
| 6,783,546 B2 | 8/2004 | Zucherman et al. |
| 6,783,721 B2 | 8/2004 | Higham et al. |
| 6,800,298 B1 | 10/2004 | Burdick et al. |
| 6,802,863 B2 | 10/2004 | Lawson et al. |
| 6,827,743 B2 | 12/2004 | Eisermann et al. |
| 6,840,960 B2 | 1/2005 | Bubb |
| 6,849,092 B2 | 2/2005 | Van Dyke et al. |
| 6,855,743 B1 | 2/2005 | Gvozdic |
| 6,875,232 B2 | 4/2005 | Nigam |
| 6,875,386 B1 | 4/2005 | Ward et al. |
| 6,875,442 B2 | 4/2005 | Holy et al. |
| 6,878,384 B2 | 4/2005 | Cruise et al. |
| 6,881,228 B2 | 4/2005 | Zdeblick et al. |
| 6,893,463 B2 | 5/2005 | Fell |
| 6,893,466 B2 | 5/2005 | Trieu |
| 6,923,811 B1 | 8/2005 | Carl et al. |
| 6,960,617 B2 | 11/2005 | Omidian et al. |
| 6,982,298 B2 | 1/2006 | Calabro et al. |
| 6,993,406 B1 | 1/2006 | Cesarano, III et al. |
| 7,008,635 B1 | 3/2006 | Coury et al. |
| 7,012,034 B2 | 3/2006 | Heide et al. |
| 7,022,522 B2 | 4/2006 | Guan et al. |
| 7,029,479 B2 | 4/2006 | Tallarida et al. |
| 7,048,766 B2 | 5/2006 | Ferree |
| 7,052,515 B2 | 5/2006 | Simonson |
| 7,060,097 B2 | 6/2006 | Fraser et al. |
| 7,066,958 B2 | 6/2006 | Ferree |
| 7,066,960 B1 | 6/2006 | Dickman |
| 7,083,649 B2 | 8/2006 | Zucherman et al. |
| 7,091,191 B2 | 8/2006 | Laredo et al. |
| 7,156,877 B2 | 1/2007 | Lotz et al. |
| 7,186,419 B2 | 3/2007 | Petersen |
| 7,201,774 B2 | 4/2007 | Ferree |
| 7,201,776 B2 | 4/2007 | Ferree et al. |
| 7,214,245 B1 | 5/2007 | Marcolongo et al. |
| 7,217,294 B2 | 5/2007 | Kusanagi et al. |
| 7,235,592 B2 | 6/2007 | Muratoglu et al. |
| 7,250,060 B2 | 7/2007 | Trieu |
| 7,258,692 B2 | 8/2007 | Thelen et al. |
| 7,264,634 B2 | 9/2007 | Schmieding |
| 7,282,165 B2 | 10/2007 | Williams, III et al. |
| 7,291,169 B2 | 11/2007 | Hodorek |
| 7,316,919 B2 | 1/2008 | Childs et al. |
| 7,332,117 B2 | 2/2008 | Higham et al. |
| 7,357,798 B2 | 4/2008 | Sharps et al. |
| 7,377,942 B2 | 5/2008 | Berry |
| 7,682,540 B2 | 3/2010 | Boyan et al. |
| 7,731,988 B2 | 6/2010 | Thomas et al. |
| 7,745,532 B2 | 6/2010 | Ruberti et al. |
| 7,828,853 B2 | 11/2010 | Ek et al. |
| 7,910,124 B2 | 3/2011 | Boyan et al. |
| 7,985,781 B2 | 7/2011 | Muratoglu et al. |
| 8,002,830 B2 | 8/2011 | Boyan et al. |
| 8,142,808 B2 | 3/2012 | Boyan et al. |
| 8,318,192 B2 | 11/2012 | Boyan et al. |
| 8,334,044 B2 | 12/2012 | Myung et al. |
| 8,475,503 B2 | 7/2013 | Denoziere et al. |
| 8,486,436 B2 | 7/2013 | Boyan et al. |
| 8,709,045 B1 | 4/2014 | Folsom |
| 8,895,073 B2 | 11/2014 | Boyan et al. |
| 9,155,543 B2 | 10/2015 | Walsh et al. |
| 9,526,632 B2 * | 12/2016 | Walsh ................... A61F 2/38 |
| 9,545,310 B2 | 1/2017 | Maher et al. |
| 9,737,294 B2 | 8/2017 | Wales et al. |
| 9,907,663 B2 | 3/2018 | Patrick et al. |
| 10,350,072 B2 * | 7/2019 | Axelrod ............ A61F 2/30734 |
| 2001/0016741 A1 | 8/2001 | Burkus et al. |
| 2001/0029399 A1 | 10/2001 | Ku |
| 2001/0038831 A1 | 11/2001 | Park et al. |
| 2001/0039455 A1 | 11/2001 | Simon et al. |
| 2001/0046488 A1 | 11/2001 | Vandenburgh et al. |
| 2002/0026244 A1 | 2/2002 | Trieu |
| 2002/0031500 A1 | 3/2002 | Maclaughlin et al. |
| 2002/0034646 A1 | 3/2002 | Canham |
| 2002/0072116 A1 | 6/2002 | Bhatia et al. |
| 2002/0140137 A1 | 10/2002 | Sapieszko et al. |
| 2002/0173855 A1 | 11/2002 | Mansmann |
| 2002/0183845 A1 | 12/2002 | Mansmann |
| 2002/0183848 A1 | 12/2002 | Ray et al. |
| 2002/0187182 A1 | 12/2002 | Kramer et al. |
| 2003/0008395 A1 | 1/2003 | Holy et al. |
| 2003/0008396 A1 | 1/2003 | Ku |
| 2003/0021823 A1 | 1/2003 | Landers et al. |
| 2003/0055505 A1 | 3/2003 | Sicotte et al. |
| 2003/0059463 A1 | 3/2003 | Lahtinen |
| 2003/0082808 A1 | 5/2003 | Guan et al. |
| 2003/0175656 A1 | 9/2003 | Livne et al. |
| 2003/0176922 A1 | 9/2003 | Lawson et al. |
| 2003/0199984 A1 | 10/2003 | Trieu |
| 2003/0220695 A1 | 11/2003 | Sevrain |
| 2003/0233150 A1 | 12/2003 | Bourne et al. |
| 2003/0236573 A1 | 12/2003 | Evans et al. |
| 2004/0010048 A1 | 1/2004 | Evans et al. |
| 2004/0024465 A1 | 2/2004 | Lambrecht et al. |
| 2004/0034434 A1 | 2/2004 | Evans et al. |
| 2004/0044412 A1 | 3/2004 | Lambrecht et al. |

(56) References Cited

U.S. PATENT DOCUMENTS

| | | |
|---|---|---|
| 2004/0052867 A1 | 3/2004 | Canham |
| 2004/0059415 A1 | 3/2004 | Schmieding |
| 2004/0059425 A1 | 3/2004 | Schmieding |
| 2004/0063200 A1 | 4/2004 | Chaikof et al. |
| 2004/0064195 A1 | 4/2004 | Herr |
| 2004/0073312 A1 | 4/2004 | Eisermann et al. |
| 2004/0092653 A1 | 5/2004 | Ruberti et al. |
| 2004/0117022 A1 | 6/2004 | Marnay et al. |
| 2004/0143327 A1 | 7/2004 | Ku |
| 2004/0143329 A1 | 7/2004 | Ku |
| 2004/0143333 A1 | 7/2004 | Bain et al. |
| 2004/0147016 A1 | 7/2004 | Rowley et al. |
| 2004/0171143 A1 | 9/2004 | Chin et al. |
| 2004/0172135 A1 | 9/2004 | Mitchell |
| 2004/0220296 A1 | 11/2004 | Lowman et al. |
| 2004/0220669 A1 | 11/2004 | Studer |
| 2004/0220670 A1 | 11/2004 | Eisermann et al. |
| 2004/0249465 A1 | 12/2004 | Ferree |
| 2005/0037052 A1 | 2/2005 | Udipi et al. |
| 2005/0043733 A1 | 2/2005 | Eisermann et al. |
| 2005/0043802 A1 | 2/2005 | Eisermann et al. |
| 2005/0049706 A1 | 3/2005 | Brodke et al. |
| 2005/0055094 A1 | 3/2005 | Kuslich |
| 2005/0055099 A1 | 3/2005 | Ku |
| 2005/0071003 A1 | 3/2005 | Ku |
| 2005/0074877 A1 | 4/2005 | Mao |
| 2005/0079200 A1 | 4/2005 | Rathenow et al. |
| 2005/0090901 A1 | 4/2005 | Studer |
| 2005/0096744 A1 | 5/2005 | Trieu et al. |
| 2005/0106255 A1 | 5/2005 | Ku |
| 2005/0137677 A1 | 6/2005 | Rush |
| 2005/0137707 A1 | 6/2005 | Malek |
| 2005/0143826 A1 | 6/2005 | Zucherman et al. |
| 2005/0149196 A1 | 7/2005 | Zucherman et al. |
| 2005/0154462 A1 | 7/2005 | Zucherman et al. |
| 2005/0154463 A1 | 7/2005 | Trieu |
| 2005/0169963 A1 | 8/2005 | Van Dyke et al. |
| 2005/0171608 A1 | 8/2005 | Peterman et al. |
| 2005/0177238 A1 | 8/2005 | Khandkar et al. |
| 2005/0209704 A1 | 9/2005 | Maspero et al. |
| 2005/0216087 A1 | 9/2005 | Zucherman et al. |
| 2005/0228500 A1 | 10/2005 | Kim et al. |
| 2005/0233454 A1 | 10/2005 | Nies et al. |
| 2005/0244449 A1 | 11/2005 | Sayer et al. |
| 2005/0260178 A1 | 11/2005 | Vandenburgh et al. |
| 2005/0261682 A1 | 11/2005 | Ferree |
| 2005/0273176 A1 | 12/2005 | Ely et al. |
| 2005/0277921 A1 | 12/2005 | Eisermann et al. |
| 2005/0278025 A1 | 12/2005 | Ku et al. |
| 2005/0287187 A1 | 12/2005 | Mansmann |
| 2006/0002890 A1 | 1/2006 | Hersel et al. |
| 2006/0052874 A1 | 3/2006 | Johnson et al. |
| 2006/0052875 A1 | 3/2006 | Bernero et al. |
| 2006/0052878 A1 | 3/2006 | Schmieding |
| 2006/0058413 A1 | 3/2006 | Leistner et al. |
| 2006/0064172 A1 | 3/2006 | Trieu |
| 2006/0064173 A1 | 3/2006 | Guederian |
| 2006/0083728 A1 | 4/2006 | Kusanagi et al. |
| 2006/0100304 A1 | 5/2006 | Vresilovic et al. |
| 2006/0121609 A1 | 6/2006 | Yannas et al. |
| 2006/0122706 A1 | 6/2006 | Lo |
| 2006/0136064 A1 | 6/2006 | Sherman |
| 2006/0136065 A1 | 6/2006 | Gontarz et al. |
| 2006/0178748 A1 | 8/2006 | Dinger, III et al. |
| 2006/0200250 A1 | 9/2006 | Ku |
| 2006/0206209 A1 | 9/2006 | Cragg et al. |
| 2006/0224244 A1 | 10/2006 | Thomas et al. |
| 2006/0229721 A1 | 10/2006 | Ku |
| 2006/0235541 A1 | 10/2006 | Hodorek |
| 2006/0241777 A1 | 10/2006 | Partin et al. |
| 2006/0257560 A1 | 11/2006 | Barone et al. |
| 2006/0259144 A1 | 11/2006 | Trieu |
| 2006/0282165 A1 | 12/2006 | Pisharodi |
| 2006/0282166 A1 | 12/2006 | Molz et al. |
| 2006/0287730 A1 | 12/2006 | Segal et al. |
| 2006/0293561 A1 | 12/2006 | Abay |
| 2006/0293751 A1 | 12/2006 | Lotz et al. |
| 2007/0010889 A1 | 1/2007 | Francis |
| 2007/0014867 A1 | 1/2007 | Kusanagi et al. |
| 2007/0032873 A1 | 2/2007 | Pisharodi |
| 2007/0038301 A1 | 2/2007 | Hudgins |
| 2007/0043441 A1 | 2/2007 | Pisharodi |
| 2007/0067036 A1 | 3/2007 | Hudgins et al. |
| 2007/0073402 A1 | 3/2007 | Vresilovic et al. |
| 2007/0093906 A1 | 4/2007 | Hudgins et al. |
| 2007/0106387 A1 | 5/2007 | Marcolongo et al. |
| 2007/0116678 A1 | 5/2007 | Sung et al. |
| 2007/0118218 A1 | 5/2007 | Hooper |
| 2007/0118225 A1 | 5/2007 | Hestad et al. |
| 2007/0134333 A1 | 6/2007 | Thomas et al. |
| 2007/0135922 A1 | 6/2007 | Trieu |
| 2007/0142326 A1 | 6/2007 | Shue |
| 2007/0162135 A1 | 7/2007 | Segal et al. |
| 2007/0164464 A1 | 7/2007 | Ku |
| 2007/0167541 A1 | 7/2007 | Ruberti et al. |
| 2007/0168039 A1 | 7/2007 | Trieu |
| 2007/0173951 A1 | 7/2007 | Wijlaars et al. |
| 2007/0179606 A1 | 8/2007 | Huyghe et al. |
| 2007/0179614 A1 | 8/2007 | Heinz et al. |
| 2007/0179615 A1 | 8/2007 | Heinz et al. |
| 2007/0179617 A1 | 8/2007 | Brown et al. |
| 2007/0179618 A1 | 8/2007 | Trieu et al. |
| 2007/0179620 A1 | 8/2007 | Seaton, Jr. et al. |
| 2007/0179621 A1 | 8/2007 | McClellan, III et al. |
| 2007/0179622 A1 | 8/2007 | Denoziere et al. |
| 2007/0196454 A1 | 8/2007 | Stockman et al. |
| 2007/0202074 A1 | 8/2007 | Shalaby |
| 2007/0203095 A1 | 8/2007 | Sadozai et al. |
| 2007/0203580 A1 | 8/2007 | Yeh |
| 2007/0208426 A1 | 9/2007 | Trieu |
| 2007/0213718 A1 | 9/2007 | Trieu |
| 2007/0213822 A1 | 9/2007 | Trieu |
| 2007/0213823 A1 | 9/2007 | Trieu |
| 2007/0213824 A1 | 9/2007 | Trieu |
| 2007/0213825 A1 | 9/2007 | Thramann |
| 2007/0224238 A1 | 9/2007 | Mansmann et al. |
| 2007/0225823 A1 | 9/2007 | Hawkins et al. |
| 2007/0227547 A1 | 10/2007 | Trieu |
| 2007/0233135 A1 | 10/2007 | Gil et al. |
| 2007/0233259 A1 | 10/2007 | Muhanna et al. |
| 2007/0265626 A1 | 11/2007 | Seme |
| 2007/0270876 A1 | 11/2007 | Kuo et al. |
| 2007/0270970 A1 | 11/2007 | Trieu |
| 2007/0270971 A1 | 11/2007 | Trieu et al. |
| 2007/0276392 A1 | 11/2007 | Beyar et al. |
| 2007/0299540 A1 | 12/2007 | Ku |
| 2008/0004707 A1 | 1/2008 | Cragg et al. |
| 2008/0015697 A1 | 1/2008 | McLeod et al. |
| 2008/0021563 A1 | 1/2008 | Chudzik |
| 2008/0031962 A1 | 2/2008 | Boyan et al. |
| 2008/0045949 A1 | 2/2008 | Hunt et al. |
| 2008/0051889 A1 | 2/2008 | Hodorek |
| 2008/0057128 A1 | 3/2008 | Li et al. |
| 2008/0075657 A1 | 3/2008 | Abrahams et al. |
| 2008/0077242 A1 | 3/2008 | Reo et al. |
| 2008/0077244 A1 | 3/2008 | Robinson |
| 2008/0097606 A1 | 4/2008 | Cragg et al. |
| 2008/0103599 A1 | 5/2008 | Kim et al. |
| 2008/0114367 A1 | 5/2008 | Meyer |
| 2008/0125870 A1 | 5/2008 | Carmichael et al. |
| 2008/0131425 A1 | 6/2008 | Garcia et al. |
| 2008/0145404 A1 | 6/2008 | Hill et al. |
| 2008/0154372 A1 | 6/2008 | Peckham |
| 2008/0166329 A1 | 7/2008 | Sung et al. |
| 2008/0221505 A1 | 9/2008 | Betts |
| 2008/0269908 A1 | 10/2008 | Warburton |
| 2008/0279941 A1 | 11/2008 | Boyan et al. |
| 2008/0279943 A1 | 11/2008 | Boyan et al. |
| 2009/0043398 A1 | 2/2009 | Yakimicki et al. |
| 2009/0138015 A1 | 5/2009 | Connor et al. |
| 2009/0177205 A1 | 7/2009 | McCormack et al. |
| 2009/0182421 A1 | 7/2009 | Silvestrini et al. |
| 2009/0263446 A1 | 10/2009 | Boyan et al. |
| 2010/0161073 A1 | 6/2010 | Thomas et al. |

(56) References Cited

U.S. PATENT DOCUMENTS

| | | |
|---|---|---|
| 2010/0198258 A1 | 8/2010 | Heaven et al. |
| 2010/0324693 A1 | 12/2010 | Hardenbrook |
| 2010/0324694 A1 | 12/2010 | Hassler et al. |
| 2011/0040332 A1 | 2/2011 | Culbert et al. |
| 2011/0172771 A1 | 7/2011 | Boyan et al. |
| 2011/0208305 A1 | 8/2011 | Malinin |
| 2011/0270400 A1 | 11/2011 | Kita et al. |
| 2011/0318704 A1 | 12/2011 | Teichmann |
| 2012/0022568 A1 | 1/2012 | Koblish et al. |
| 2012/0053642 A1 | 3/2012 | Lozier et al. |
| 2012/0203346 A1 | 8/2012 | Kraus |
| 2013/0006368 A1 | 1/2013 | Walsh et al. |
| 2013/0211451 A1 | 8/2013 | Wales et al. |
| 2014/0214080 A1 | 7/2014 | Wales et al. |
| 2014/0324169 A1 | 10/2014 | Maher et al. |
| 2015/0351815 A1 | 12/2015 | Wales et al. |
| 2016/0038308 A1 | 2/2016 | Walsh et al. |
| 2016/0287392 A1 | 10/2016 | Patrick et al. |
| 2016/0287407 A1 | 10/2016 | Patrick et al. |
| 2017/0165074 A1 | 6/2017 | Walsh et al. |
| 2017/0304039 A1 | 10/2017 | Eaves, III et al. |
| 2018/0185159 A1 | 7/2018 | Patrick et al. |
| 2019/0314157 A1* | 10/2019 | Walsh .................. A61F 2/4603 |

FOREIGN PATENT DOCUMENTS

| | | |
|---|---|---|
| EP | 0222407 A2 | 5/1987 |
| EP | 0346129A 1 | 12/1989 |
| EP | 0505634 A1 | 9/1992 |
| EP | 041001OB1 | 10/1993 |
| EP | 0411105 B1 | 6/1995 |
| EP | 0845480 A1 | 6/1998 |
| EP | 0919209 A1 | 6/1999 |
| EP | 1287796A 1 | 3/2003 |
| EP | 1030697 B1 | 8/2003 |
| EP | 1344538 A1 | 9/2003 |
| EP | 1584338 A2 | 10/2005 |
| EP | 1482996 B1 | 11/2005 |
| GB | 02056882 A | 3/1981 |
| GB | 02128501 A | 5/1984 |
| JP | 02-184580 | 7/1990 |
| JP | 04053843 | 2/1992 |
| JP | 07247365 | 9/1995 |
| JP | 11035732 | 2/1999 |
| JP | 2005-199054 | 7/2005 |
| JP | 2006-101893 | 4/2006 |
| WO | W090/007545 A2 | 7/1990 |
| WO | W090/007575A 1 | 7/1990 |
| WO | W090/010018 A1 | 9/1990 |
| WO | W093/016664A 1 | 9/1992 |
| WO | W094/001483A 1 | 1/1994 |
| WO | W095/025183A 1 | 9/1995 |
| WO | W097/006101 A1 | 2/1997 |
| WO | W097/046178 A1 | 12/1997 |
| WO | W098/002146 A2 | 1/1998 |
| WO | W098/050017 A1 | 11/1998 |
| WO | W099/025391 A2 | 5/1999 |
| WO | W099/034845A 1 | 7/1999 |
| WO | W000/030998A 1 | 6/2000 |
| WO | W000/042991 A1 | 7/2000 |
| WO | W000/062829A 1 | 10/2000 |
| WO | W000/066191 | 11/2000 |
| WO | W001/002033A 1 | 1/2001 |
| WO | W001/022902 A2 | 4/2001 |
| WO | W001/059160A 1 | 8/2001 |
| WO | W001/064030A 1 | 9/2001 |
| WO | W001/070436 A1 | 9/2001 |
| WO | W001/091822A 1 | 12/2001 |
| WO | W002/009647 A2 | 2/2002 |
| WO | W002/030480A 1 | 4/2002 |
| WO | W002/064182 A3 | 8/2002 |
| WO | W003/030787 A1 | 4/2003 |
| WO | W003/092760A 1 | 11/2003 |
| WO | W004/060554A 1 | 7/2004 |
| WO | W004/101013 A1 | 11/2004 |
| WO | W005/077013 A2 | 8/2005 |
| WO | W005/077304A 1 | 8/2005 |
| WO | W005/097006 A2 | 10/2005 |
| WO | W006/018531 A2 | 2/2006 |
| WO | W006/019634A 1 | 2/2006 |
| WO | W006/030054A 1 | 3/2006 |
| WO | W006/034365 A2 | 3/2006 |
| WO | WO 2006/060416 | 6/2006 |
| WO | WO 2012/162552 | 11/2012 |

OTHER PUBLICATIONS

Ariga et al., "Immobilization of Microorganisms with PVA Hardened by Iterative Freezing and Thawing," Journal of Fermentation Technology, 65(6): pp. 651-658 (1987).

Boyan et al., "Effect of Titanium Surface Characteristics on Chondrocytes and Osteoblasts in Vitro," Cells and Materials, vol. 5, No. 4, pp. 323-335 (1995).

Boyan et al., "Osteoblast-Mediated Mineral Deposition in Culture is Dependent on Surface Microtopography," Calcif. Tissue Int., 71:519-529 (2002).

Bray et al., Poly(vinyl alcohol) Hydrogels for Synthetic Articular Cartilage Material, M. Biomed. Mater. Res., vol. 7, pp. 431-443.

Brunette, "The Effects of Implant Surface Topography on the Behavior of Cells," Int. J. Oral Maxillofac Implants, 3:231-240 (1988).

Chen et al., "Boundary layer infusion of heparin prevents thrombosis and reduces neointimal hyperplasia in venous polytetrafluoroethylene grafts without system anticoagulation," J. Vascular Surqery, 22:237-247 (1995).

Chu et al., "Polyvinyl Alcohol Cryogel: An Ideal Phantom Material for MR Studies of Arterial Elasticity," Magnetic Resonance in Medicine, v. 37, pp. 314-319 (1997).

Hickey et al., "Mesh size and diffusive characteristics of semicrystalline poly(vinyl alcohol) membranes prepared by freezing/thawing techniques," Journal of Membrane Science, 107(3), pp. 229-237 (1995).

Hoffman et al., "Interactions of Blood and Blood Components at Hydrogel Interfaces," Ann. New York Acad. Sci., 283:372-382 (1977).

Hunt, Knee Simulation, Creep, and Friction Tests of Poly(Vinyl Alcohol) Hydrogels Manufactured Using Injection Molding and Solution Casting, Thesis for M.S., University of Notre Dame (Jul. 2006).

Katta et al., "Friction and wear behavior of poly(vinyl alcohol)/poly(vinyl pyrrolidone) hydrogels for articular cartilage replacement," Journal of Biomedical Materials Research, vol. 83A, pp. 471-479 (2007).

Kieswetter et al., "The Role of Implant Surface Characteristics in the Healing of Bone," Crit. Rev. Oral Biol. Med., 7(4):329-345 (1996).

Kobayashi et al., "Characterization of a polyvinyl alcohol-hydrogel artificial articular cartilage prepared by injection molding," J. Biomater. Sci. Polymer Edn., 15(6): 741-751 (2003).

Kobayashi et al., "Development of an artificial meniscus using polyvinyl alcohol-hydrogel for early return to, and continuance of, athletic life in sportspersons with severe meniscus injury. I: mechanical evaluation." The Knee, 10 (2003); 47-51.

Kohavi et al., "Markers of primary mineralization are correlated with bone-bonding ability of titanium or stainless steel in vivo," Clin. Oral. Impl. Res., 6:1-13 (1995).

Koutsopoulos et al., "Calcification of porcine and human cardiac valves: testing of various inhibitors for antimineralization," J. Mater. Sci. Mater. Med., 9:421-424 (1998).

Kwak, BK, et al., "Chitin-based Embolic Materials in the Renal Artery of Rabbits: Pathologic Evaluation of an Absorbable Particulate Agent", Radiology, 236:151-158 (2005).

Landolt et al., "Electrochemical micromachining, polishing and surface structuring of metals: fundamental aspects and new developments", Elsevier Science Ltd., pp. 3185-3201 (2003).

Lazzeri et al., "Physico-chemical and mechanical characterization of hydrogels of poly(vinyl alcohol) and hyaluronic acid," J. Mater. Sci. In Med., 5:862-867 (1994).

(56) References Cited

OTHER PUBLICATIONS

Liao et al., "Response of rat osteoblast-like cells to microstructured model surfaces in vitro," Biomaterials, 24, pp. 649-654 (2003).
Lozinsky et al., "Study of cryostructurization of polymer systems. VII. Structure formation under freezing of poly(vinyl alcohol) acqueous solutions," Colloid & Polymer Science, vol. 264, pp. 19-24 (1986).
Lozinsky et al., "Study of Cryostructuration of Polymer Systems. XII. Poly(vinyl alcohol) Cryogels: Influence of Low-Molecular Electrolytes," Journal of Applied Polymer Science, vol. 61, pp. 1991-1998 (1996).
Lozinsky et al., "Study of Cryostructuration of Polymer Systems. XI. The Formation of PVA Cryogels by Freezing-Thawing the Polymer Aqueous Solutions Containing Additives of Some Polyols," Journal of ADDlied Polymer Science, vol. 58, DD. 171-177 (1995).
Lozinsky et al., "Poly(vinyl alcohol) cryogels employed as matrices for cell immobilization. 2. Entrapped cells resemble porous fillers in their effects on the properties of PVA-cryogel carrier," Enzyme and Microbial Technoloav, vol. 20, No. 3, DD. 182-190 (1997).
Lozinsky et al., "Poly(vinyl alcohol) cryogels employed as matrices for cell immobilization. 3. Overview of recent research and developments," Enzyme and Microbial Technology, vol. 23, No. 3-4, DD. 227-242 (1998).
Lusta et al., "Immobilization of fungus *Aspergillus* sp. by a novel cryogel technique for production of extracellular hydrolytic enzymes", Process Biochemistry, vol. 35, pp. 1177-1182 (2000).
Ma et al., "Friction Properties of novel PVP/PVA blend hydrogels as artificial cartilage," Journal of Biomedical Materials Research, vol. 93A, pp. 1016-1019 (2010).
Martin et al., "Effect of titanium surface roughness on proliferation, differentiation, and protein synthesis of human osteoblast-like cells (MG63)," Journal of Biomedical Materials Research, vol. 29, DD. 389-401 (1995).
Nagura et al., "Structure of poly(vinyl alcohol) hydrogel prepared by repeated freezing and melting," Polymer, 30:762-765 (1989).
Nakashima et al., "Study on Wear Reduction Mechanisms of Artificial Cartilage by Synergistic Protein Boundary Film Formation," Japan Soc'y of Mech. Eng'r Int'l J., Series C, vol. 48, No. 4, pp. 555-561 (2005).
Oka et al., "Development of an Artificial Articular Cartilage", Clinical Materials, vol. 6, pp. 361-381 (1990).
Ong et al., "Osteoblast Responses to BMP-2-Treated Titanium In Vitro," The International Journal of Oral & Maxillofacial Implants, vol. 12, No. 5, pp. 649-654 (1997).
Peppas et al., "Reinforced uncrosslinked poly(vinyl alcohol) gels produced by cyclic freezing-thawing processes: a short review," Journal of Controlled Release, 16(3): 305-310 (1991).
Peppas et al., "Structure of Hydrogels by Freezing-Thawing Cyclic Processing," Bulletin of the American Physical Society, 36:582 (1991).
Peppas et al., "Controlled release from poly(vinyl alcohol) gels prepared by freezing-thawing processes," Journal of Controlled Release, vol. 18, pp. 95-100 (1992).
Peppas et al., "Ultrapure poly(vinyl alcohol) hydrogels with mucoadhesive drug delivery characteristics," European Journal of Pharmaceutics and Biopharmaceutics, 43(1): 51-58 (1997).
Ratner et al., Biomaterials Science an Introduction to Materials in Medicine, Academic Press, pp. 52, 53, & 62 (1996).
Ricciardi et al., "Structure and Properties of Poly(vinyl alcohol) Hydrogels Obtained by Freeze/Thaw Techniques," Macromol. Symp., 222: 49-63 (2005).
Schwartz et al., "Underlying Mechanisms at the Bone-Biomaterial Interface," Journal of Cellular Biochemistry, 56:340-347 (1994).
Singh et al., "Polymeric Hydrogels: Preparation and Biomedical Applications," J. Sci. Ind. Res., 39:162-171 (1980).
Stauffer et al., "Poly(vinyl alcohol) hydrogels prepared by freezing-thawing cyclic processing," Polymer 33(1818):3932-3936 (1992).
Stewart et al., "Protein release from PVA gels prepared by freezing and thawing techniques," Proc. Int. Symp. Controlled Release Bioact. Mater., 26[1], 1004-1005 (1999).
Szczesna-Antezak et al., "*Bacillus subtilis* cells immobilised in PVA-cryogels," Biomolecular Engineering, vol. 17, pp. 55-63 (2001).
The American Heritage® Science Dictionary [online], Houghton Mifflin Company, 2002 [retrieved on Jun. 3, 2008]. Retrieved from the internet: <URL: http://dictionary.reference.com/browse/pore>.
Watase et al., "Rheological and DSC Changes in Poly(vinyl alcohol) Gels Induced by Immersion in Water," Journal of Polymer Science, Polym. Phys. Ed, 23(9): 1803-1811 (1985).
Watase et al., "Thermal and rheological properties of poly(vinyl alcohol) hydrogels prepared by repeated cycles of freezing and thawing," Makromol. Chem., v. 189, pp. 871-880 (1988).
Willcox et al., "Microstructure of Poly(vinyl alcohol) Hydrogels Produced by Freeze/Thaw Cycling," Journal of Polymer Sciences: Part B: Polymer Physics, vol. 37, pp. 3438-3454 (1999).
WordNet® 3.0 [online], Princeton University, 2006 [retrieved on Aug. 6, 2008]. Retrieved from the Internet: <URL: http://dictionary.reference.com/browse/mesh>.
Yamaura et al., "Properties of Gels Obtained by Freezing/Thawing of Poly(vinyl Alcohol)/Water/Dimethyl Sulfoxide Solutions," J. Appl. Polymer Sci., 37:2709-2718 (1989).
Yokoyama et al., "Morphology and structure of highly elastic poly(vinyl alcohol) hydrogel prepared by repeated freezing-and-melting", Colloid & Polymer Science, vol. 264, No. 7, pp. 595-601 (1986).
Zheng-Qiu et al., "The development of artificial articular cartilage—PVA-hydrogel," Bio-Medical Materials and Engineering, vol. 8, pp. 75-81 (1998).

* cited by examiner

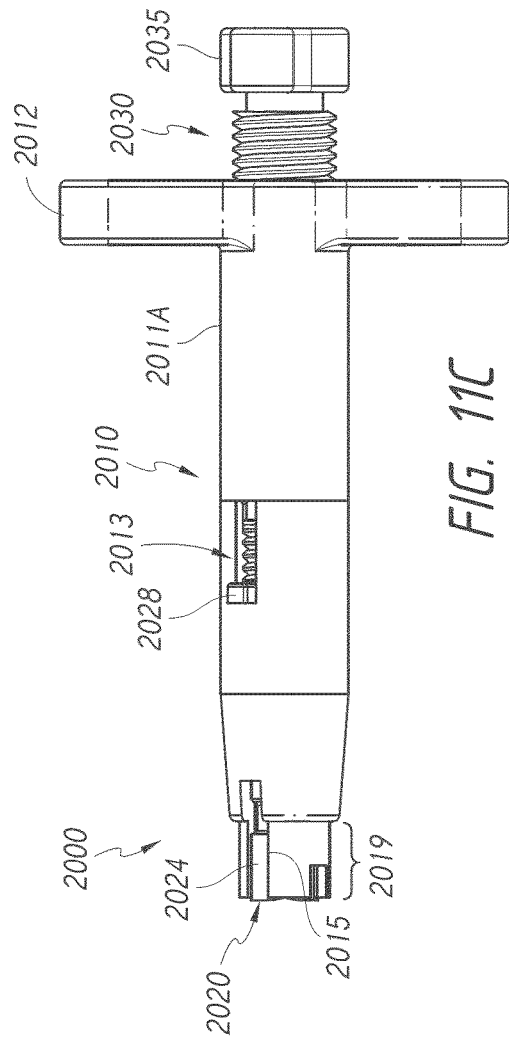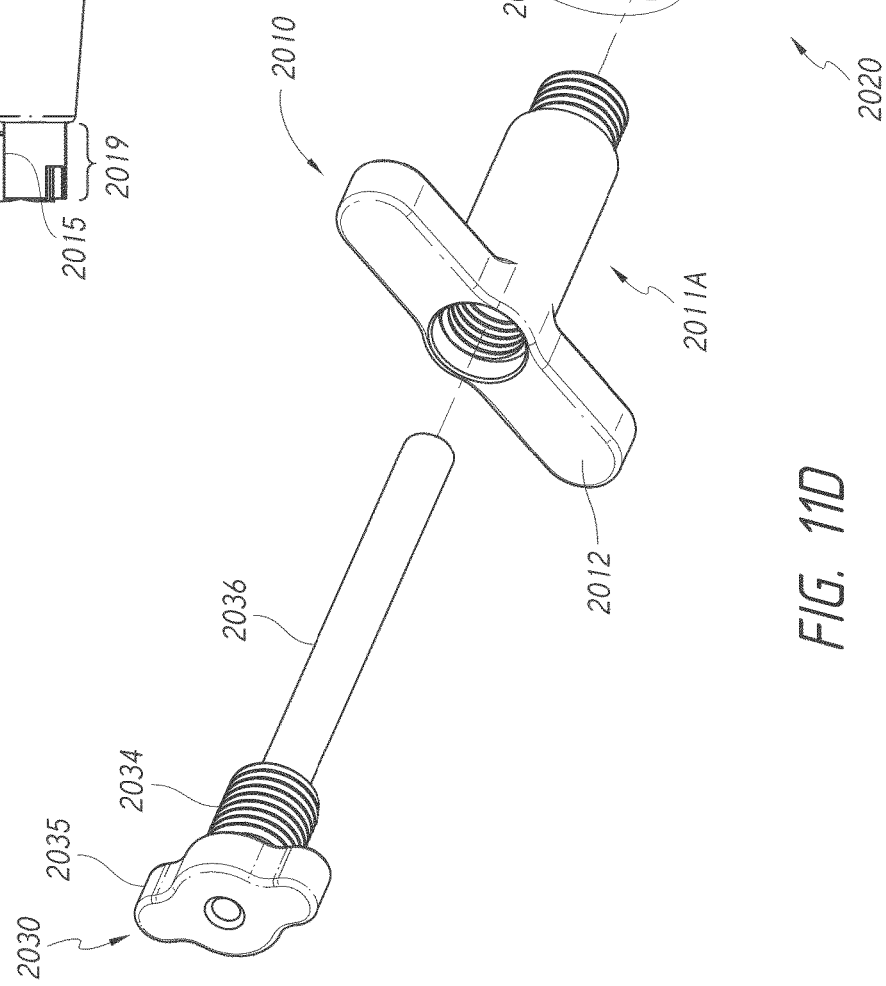
FIG. 11C
FIG. 11D

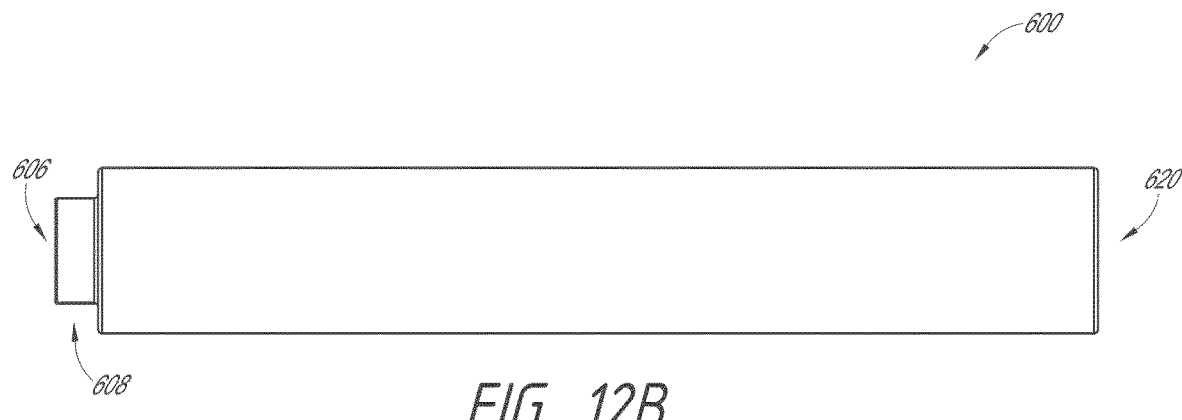
FIG. 12B
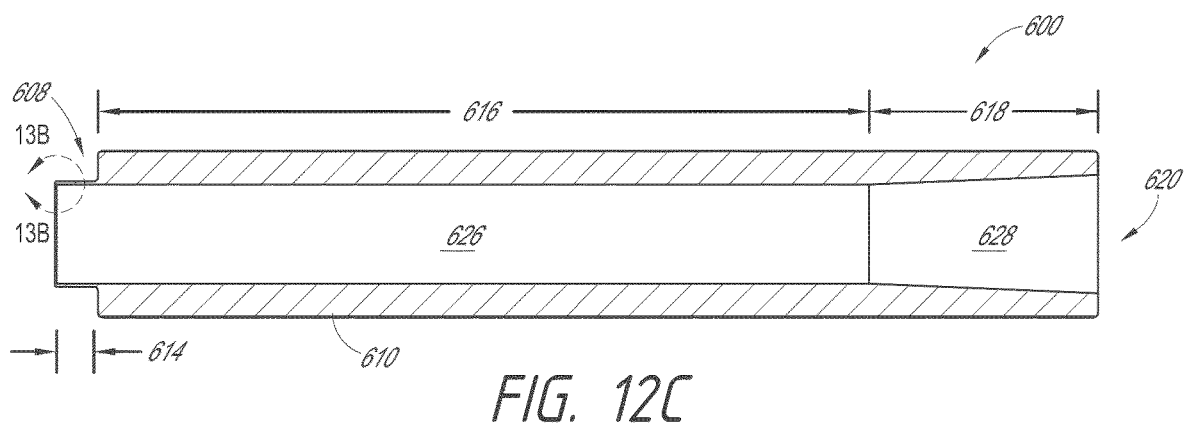
FIG. 12C
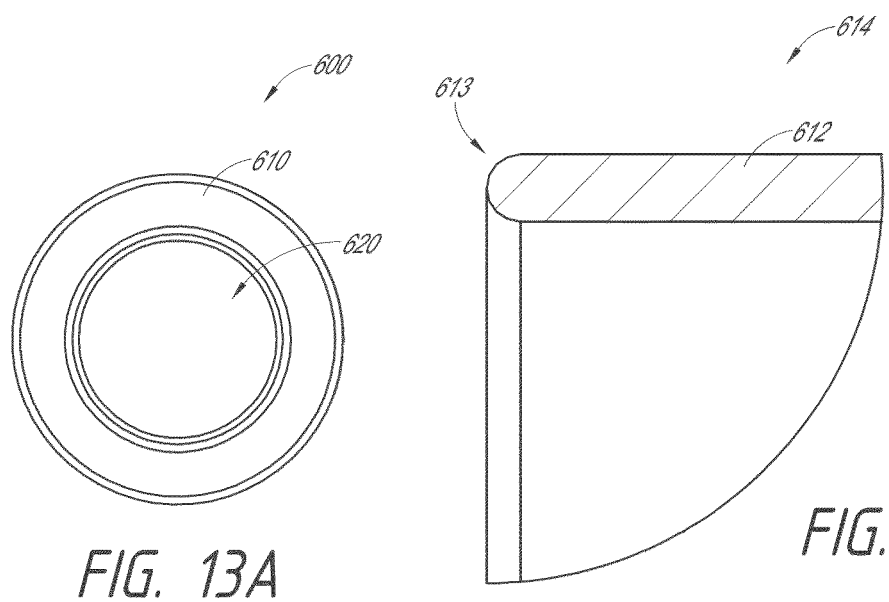
FIG. 13A
FIG. 13B

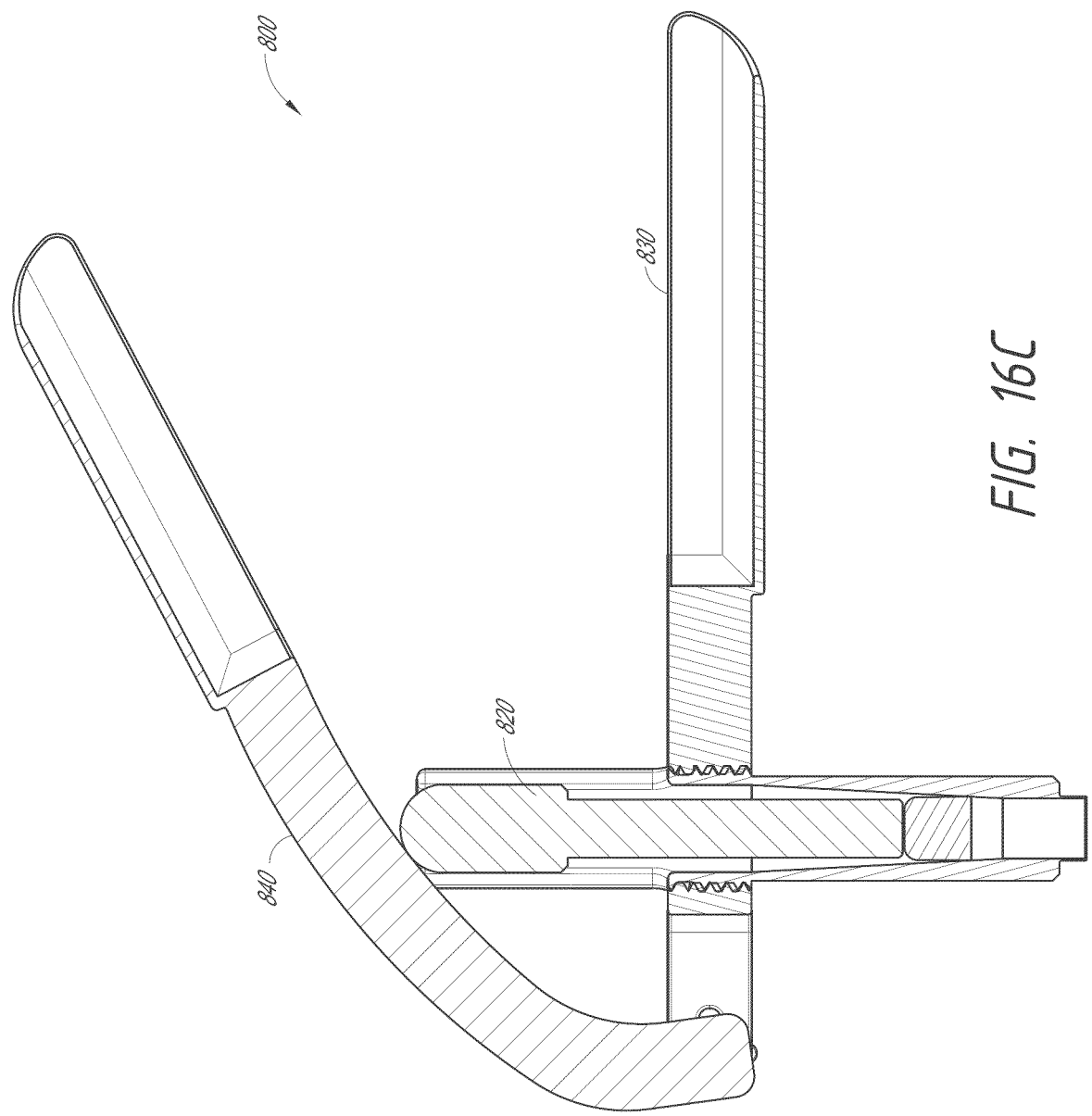

TOOLING FOR CREATING TAPERED OPENING IN TISSUE AND RELATED METHODS

CROSS-REFERENCE TO RELATED APPLICATIONS

This application is a divisional application of U.S. patent application Ser. No. 15/098,265, filed Apr. 13, 2016, which claims priority benefit of U.S. Provisional Application No. 62/147,548, filed Apr. 14, 2015, the contents of which are incorporated by reference herein and made a part of the present application. In addition, U.S. patent application Ser. No. 13/480,272, filed on May 24, 2012 and issued on Oc. 13, 2015 as U.S. Pat. No. 9,155,543, is hereby incorporated by reference herein in its entirety and made a part of the present application.

BACKGROUND

Field

This application relates generally to anatomical implants, and more specifically, to hydrogel joint implants and various tools, devices, systems and methods related thereto.

Description of Related Art

Implants are often used to replace deteriorated or otherwise damaged cartilage within a joint. Such devices can be used to treat osteoarthritis, rheumatoid arthritis, other inflammatory diseases, generalized joint pain and/or other joint diseases. To ensure proper function and long term effectiveness, such implants should be properly secured within a patient's bone or other implant site.

SUMMARY

According to some embodiments, a tool for creating a wedge (e.g., reverse tapered) opening within tissue comprises an outer member comprising a distal end, the distal end comprising a tapered portion configured to be inserted within a cylinder-shaped opening created within tissue, a cutting member coupled to the outer member, the cutting member comprising at least one cutter configured to be radially expanded, and an inner member configured to be moved within an interior of the cutting member when moved relative to the outer member, wherein radial expansion of the at least one cutter is configured to occur when the inner member is moved within the interior of the cutting member, wherein the at least one cutter is configured to be radially expanded at an angle relative to a longitudinal axis of the tool so as to create the wedge opening within tissue when the tool is expanded and rotated relative to said tissue.

According to some embodiments, the tool is configured to be rotated manually to create the wedge opening, wherein the at least one cutter comprises a sloped inner surface, such that when the inner member is advanced within an interior of the cutting member, the inner member engages and urges the at least one cutter radially outwardly, and wherein the at least one cutter is configured to radially retract once the inner member is retracted from an interior of the cutting member.

According to some embodiments, the inner member is configured to engage and move relative to the outer member. In one embodiment, the inner portion comprises a threaded portion configured to engage a corresponding threaded portion of the outer member. In some embodiments, engagement of the inner portion relative to the outer member is configured to move the inner portion relative to the outer member, in a longitudinal or axial direction of the tool. In some embodiments, the tool is configured to be rotated manually to create the wedge opening.

According to some embodiments, the at least one cutter is resiliently biased radially inwardly, and wherein advancement of the inner member within an interior of the cutting member urges the at least one cutter radially outwardly. In some embodiments, the at least one cutter comprises two cutters that are oriented opposite of each other. In some embodiments, the distal end of the outer member comprises a tapered portion sized, shaped and configured to fit within a cylindrical opening of tissue. In one embodiment, the tapered portion of the outer member comprises a cylindrical shape.

According to some embodiments, the cutting member is secured to the outer member using a press-fit connection, another mechanical connection and/or the like. In some embodiments, the outer member comprises a first outer member portion and at least a second outer member portion, wherein the first outer member portion is configured to couple and secure to the second outer member portion prior to use. In some arrangements, the first outer member portion is configured to couple to the second outer member portion using a threaded connection. In one embodiment, the cutting member is configured to be secured relative to the outer member when the first outer member portion is coupled to the second outer member portion. In some configurations, the cutting member comprises at least one protruding member, wherein the at least one protruding member is configured to move within at least one corresponding slot of at least one of the first outer member portion and the second outer member portion when the first outer member portion is coupled to the second outer member portion.

According to some embodiments, the tool is configured to be reusable. In other embodiments, the tool is configured to be disposable. In some embodiments, the tool is at least partially reusable and at least partially disposable. In one embodiment, the tool is configured to be sterilized between uses.

According to some embodiments, the at least one cutter comprises a sloped inner surface, such that when the inner member is advanced within an interior of the cutting member, the inner member engages and urges the at least one cutter radially outwardly. In some embodiments, the at least one cutter is configured to radially retract once the inner member is retracted from an interior of the cutting member.

According to some embodiments, the tool comprises a metallic material (e.g., stainless steel). In some embodiments, the tool comprises a polymeric material. In some embodiments, the tool is cannulated to permit the passage of a guide pin or other device through an axial opening through the tool.

According to some embodiments, a kit for treating tissue of a subject comprises a tool according to any embodiments disclosed herein, and an implant (e.g., hydrogel implant) configured to be inserted and secured within the wedge opening created by the tool. In some embodiments, the kit further comprise an introducer, wherein the introducer is configured to deliver an implant within the wedge opening in an at least partially compressed and release the implant into an expanded shape, wherein the implant, once implanted and in the expanded shape, is configured to securely remain within the wedge opening after implantation. In some embodiments, the kit further comprises a separate tool configured to create the cylinder-shaped opening. In some embodiments, the separate tool comprises a mechanically-operated tool comprising a drill bit. In some arrangements, the kit further comprises a mechanically-assisted tool to help move the implant within the wedge opening.

According to some embodiments, a method of treating a joint of a patient comprises creating a cylindrical recess in a bone located at or near a targeted joint, wherein the cylindrical recess comprises a surface opening along an outer surface of the bone, a bottom opening along the distal end of the recess and side walls generally extending between the surface opening and the bottom opening, wherein the side walls are generally perpendicular to the longitudinal axis of the cylindrical recess, creating a wedge recess in the bone using a tool by removing additional tissue from the side walls of the cylindrical recess, wherein, once the wedge recess is created, a diameter or other cross-sectional dimension of the bottom opening is larger than a diameter or other cross-sectional dimension of the surface opening, wherein the tool comprises a cutting portion, the cutting portion comprising at least one cutter that is radially expanded by advancing an inner member within the cutting portion, wherein the wedge recess is created by manually rotating the tool so that the cutting portion rotates relative to the bone, at least partially withdrawing the inner member of the tool from the cutting portion to radially retract the at least one cutter of the cutting portion, at least partially radially compressing an implant having a wedge shape, the implant comprising a first end and a second end and body extending between the first end and the second end, said second end being generally opposite of said first end, wherein when the implant is in a radially uncompressed state, a diameter or other cross-sectional dimension of the first end is smaller than a diameter or other cross-sectional dimension of the second end, while the implant is in a radially compressed state, inserting the implant within the wedge recess, wherein the second end of the implant is inserted first within the wedge recess, wherein the second end of the implant is adjacent the bottom opening of the wedge recess, and wherein the first end of the implant is adjacent the surface opening of the wedge recess when the implant is properly positioned within the wedge recess, and releasing the implant from a radially compressed state to a less compressed state, when the implant is properly positioned within the wedge recess, wherein, when the implant is in a less compressed state, the diameter or other cross-sectional dimension of the second end of the implant is larger than the diameter or other cross-sectional dimension of the surface opening of the wedge recess.

According to some embodiments, wherein, when the implant is in a radially uncompressed state, the body of the implant imparts a radial force at least partially along the side walls of the wedge recess, thereby helping to secure the implant within the wedge recess, wherein creating a cylindrical recess comprises using a drill bit, wherein the at least one cutter is angled relative to a longitudinal axis of the tool when the at least one cutter is radially expanded, wherein the at least one cutter comprises at least two cutters, and wherein the implant is radially compressed and inserted within the wedge recess using an introducer.

According to some embodiments, wherein, when the implant is in a radially uncompressed state, the body of the implant imparts a radial force at least partially along the side walls of the wedge recess, thereby helping to secure the implant within the wedge recess. In one embodiment, creating a cylindrical recess comprises using a drill bit. In several arrangements, wherein the at least one cutter is angled relative to a longitudinal axis of the tool when the at least one cutter is radially expanded. In some embodiments, the at least one cutter comprises at least two cutters (e.g., 2, 3, 4, 5, more than 5 cutters, etc.).

According to some embodiments, the drill bit is cannulated, and wherein said drill bit is positioned over a guide pin to place a working end of the drill bit near a targeted location of the recess. In some embodiments, the implant is radially compressed and inserted within the wedge recess using an introducer. In one embodiment, an interior of the introducer is tapered to radially compress an implant as the implant is advanced through the introducer. In some arrangements, a distal end of the introducer is sized and configured to fit at least partially within the recess. In some embodiments, the implant is urged through an interior of the introducer using a plunger or other pusher member. In one embodiment, the implant is urged through an interior of the introducer using a mechanically-assisted device. In one configuration, the mechanically-assisted device comprises a handle and a clamp coupled to said handle, wherein moving the clamp relative to the handle urges a plunger within an introducer to radially compress the joint implant and insert the joint implant within the recess. In some embodiments, the clamp is rotatably coupled to the handle.

According to some embodiments, a ratio of the diameter or other cross-sectional dimension of the bottom opening of the wedge recess to the diameter or other cross-sectional dimension of the surface opening of the wedge recess is approximately between 1.05 and 1.3. In one embodiment, a ratio of the diameter or other cross-sectional dimension of the bottom opening of the wedge recess to the diameter or other cross-sectional dimension of the surface opening of the wedge recess is at least 1.1. In some embodiments, the diameter or other cross-sectional dimension of the bottom opening of the wedge recess is approximately 5% to 25% larger than the diameter or other cross-sectional dimension of the surface opening of the wedge recess. In some embodiments, the tool is cannulated such that the tool is delivered to a targeted anatomical site over a guide pin.

According to some embodiments, a method of treating a joint of a patient comprises creating a cylindrical recess in a bone located at or near a targeted joint, wherein the cylindrical recess comprises a surface opening along an outer surface of the bone, a bottom opening along the distal end of the recess and side walls generally extending between the surface opening and the bottom opening, wherein the side walls are generally perpendicular to the longitudinal axis of the cylindrical recess, creating a wedge recess in a bone using a tool by removing additional tissue from the side walls of the cylindrical recess, wherein, once the reverse tapered recess is created, a diameter or other cross-sectional dimension of the bottom opening is larger than a diameter or other cross-sectional dimension of the surface opening, wherein the tool comprises a cutting portion, the cutting portion comprising at least one cutter that is radially expanded by advancing an inner member within an outer member of the tool, wherein the reverse tapered recess is created by rotating the tool, removing the tool from the recess after at least partially withdrawing the inner member of the tool from the outer member in order to radially retract the at least one cutter, at least partially radially compressing an implant having a wedge shape, the implant comprising a first end and a second end and body extending between the first end and the second end, said second end being generally opposite of said first end, wherein when the implant is in a radially uncompressed state, a diameter or other cross-sectional dimension of the first end is smaller than a diameter or other cross-sectional dimension of the second end, while the implant is in a radially compressed state, inserting the implant within the wedge recess, wherein the second end of the implant is inserted first within the wedge recess, wherein the second end of the implant is adjacent the bottom opening of the wedge recess, and wherein the first end of the implant is adjacent the surface opening of the wedge recess when the implant is properly positioned within the wedge recess, and releasing the implant from a radially compressed state to a less compressed state, when the implant is properly positioned within the wedge recess;

wherein, when the implant is in a less compressed state, the diameter or other cross-sectional dimension of the second end of the implant is larger than the diameter or other cross-sectional dimension of the surface opening of the wedge recess, wherein, when the implant is in a radially uncompressed state, the body of the implant imparts a radial force at least partially along the side walls of the wedge recess, thereby securing the implant within the wedge recess.

According to some embodiments, creating a cylindrical recess comprises using a drill bit. In some embodiments, the at least one cutter is angled relative to a longitudinal axis of the tool when radially expanded. In one embodiment, creating a wedge recess comprises manually rotating the tool once the at least one cutter is radially expanded. In some embodiments, creating a wedge recess comprises rotating the tool with the assistance of another device (e.g., mechanically-assisted, electromechanically-assisted, pneumatically-assisted device, etc.).

According to some embodiments, the at least one cutter comprises at least two cutters. In some embodiments, the drill bit is cannulated, and wherein said drill bit is positioned over a guiding device (e.g., guide pin) to place a working end of the drill bit near a targeted location of the recess. In some embodiments, the implant is radially compressed and inserted within the wedge recess using an introducer. In some embodiments, an interior of the introducer is tapered to radially compress an implant as said implant is advanced through the introducer. In some embodiments, the interior of the introducer is tapered (e.g., from larger to smaller diameter or cross-sectional dimension) from the proximal end to the distal end. In some embodiments, the interior of the introducer is tapered (e.g., from larger to smaller diameter or cross-sectional dimension) from the distal end to the proximal end.

According to some embodiments, a distal end of the introducer is sized and configured to fit at least partially within the recess. In one embodiment, the implant is urged through an interior of the introducer using a plunger or other pusher member. In some embodiments, the implant is urged through an interior of the introducer using a mechanically-assisted device. In some embodiments, the mechanically-assisted device comprises a handle and a clamp coupled to said handle, wherein moving the clamp relative to the handle urges a plunger within an introducer to radially compress the joint implant and insert the joint implant within the recess. In one embodiment, the clamp is rotatably coupled to the handle.

According to some embodiments, a ratio of the diameter or other cross-sectional dimension of the bottom opening of the wedge recess to the diameter or other cross-sectional dimension of the surface opening of the wedge recess is approximately between 1.05 and 1.3. In some embodiments, a ratio of the diameter or other cross-sectional dimension of the bottom opening of the wedge recess to the diameter or other cross-sectional dimension of the surface opening of the wedge recess is at least 1.1. In some embodiments, the diameter or other cross-sectional dimension of the bottom opening of the wedge recess is approximately 5% to 25% larger than the diameter or other cross-sectional dimension of the surface opening of the wedge recess. In some embodiments, the tool is cannulated such that the tool is delivered to a targeted anatomical site over a guide pin or other guide tool or device.

According to some embodiments, a tool for creating a reverse tapered opening within tissue comprises an outer member comprising a distal end, the distal end comprising a tapered portion configured to be inserted within a cylindered opening created within tissue, a cutting member positioned along a distal end of the outer member, the cutting member comprising at least one cutter configured to be radially expanded and an inner member configured to engage at least a portion of the outer member and configured to be moved within an interior of the outer member, wherein a distal end of the inner member is configured to be moved within an interior of the cutting member, wherein radial expansion of the at least one cutter is configured to occur when the inner member is moved within the interior of the cutting member, wherein the at least one cutter is configured to be radially expanded at an angle relative to a longitudinal axis of the tool so as to create a reverse tapered opening within tissue when the tool is expanded and rotated.

According to some embodiments, the inner portion comprises a threaded portion configured to engage a corresponding threaded portion of the outer member. In some embodiments, wherein engaging the threaded portion of the inner portion relative to the corresponding threaded portion of the outer member selectively moves the inner portion relative to the outer member, in a longitudinal or axial direction of the tool. In one embodiment, the at least one cutter comprises two cutters that are oriented opposite of each other. In some embodiments, the at least one cutter comprises two or more (e.g., 3, 4, 5, 6, more than 6, etc.) cutters.

According to some embodiments, the distal end of the outer member comprises a tapered portion sized, shaped and configured to fit within a cylindrical opening or recess. In some embodiments, the cutting member is secured to a distal end of the outer member using at least one of a press-fit connection and a mechanical connection. In some embodiments, the at least one cutter comprises a sloped inner surface, such that when the inner member is advanced within an interior of the cutting member, the inner member engages and urges the at least one cutter radially outwardly. In one embodiment, the tool comprises a metallic material (e.g., stainless steel, other metal and/or alloy, etc.). In some embodiments, the tool comprises a polymeric material. In some embodiments, the at least one cutter is configured to radially retract once the inner member is retracted from an interior of the cutting member.

According to some embodiments, a method of creating for creating a reverse tapered opening within tissue comprises creating a cylindrical opening within a targeted anatomical site of a subject using a first device, and removing additional tissue from the sidewalls of the cylindrical opening using a cutting member of a tool to create a reverse tapered opening within the targeted anatomical site using a second device, wherein the tool comprises an inner member that is at least partially advanced relative to an outer member to radially expand a cutting portion, the cutting portion comprising at least one cutter, wherein, once the reverse tapered opening is created, a diameter or other cross-sectional dimension of a bottom surface of the opening is larger than a diameter or other cross-sectional dimension of a top surface of the opening. In some embodiments, the method additionally comprises removing the tool from the opening.

According to some embodiments, a ratio of the diameter or other cross-sectional dimension of the bottom surface of the opening to the diameter or other cross-sectional dimension of the top surface of the opening is approximately between 1.05 and 1.3. In some embodiments, a ratio of the diameter or other cross-sectional dimension of the bottom surface of the opening to the diameter or other cross-sectional dimension of the top surface of the opening is at least 1.1.

According to some embodiments, the first tool and the second tool are cannulated. In some embodiments, the first tool and the second tool are positioned and aligned relative to the targeted anatomical location using a guide pin or other guiding device. In one embodiment, the first tool comprises a drill bit. In some embodiments, the drill bit is configured to be rotated using a motorized device. In some embodiments, the drill bit is configured to be rotated using a manually-operated device.

According to some embodiments, the at least one cutter comprises at least two cutters (e.g., 2, 3, 4, 5, 6, more than 6 cutters, etc.). In some embodiments, the at least one cutter is configured to be radially expanded at an angle relative to a longitudinal axis of the second tool. In some embodiments, the at least one cutter is configured to be radially expanded when an inner member of the second device is moved at least partially within an interior of the cutting member. In some embodiments, the inner member of the second device is moved within the interior of the cutting member by moving the inner member relative to an outer member of the second device.

According to some embodiments, the inner member is moved relative to the outer member using a threaded connection between the inner and outer members. In some embodiments, the step of removing additional tissue from the sidewalls of the cylindrical opening to create a reverse tapered opening comprises rotating the second device once the cutting member has been radially expanded. In some embodiments, the method further comprises removing the second device once the reverse tapered opening has been created. In one embodiment, the step of removing the second device comprises radially retracting the cutting member and retracting the second device from the opening.

According to some embodiments, the second device is configured to be manually rotated. In some embodiments, the second device is configured to be rotated with the assistance of a motorized device. In one embodiment, the method further includes securing an implant within the reverse tapered opening. In some embodiments, the implant is secured within the reverse tapered opening using an introducer. In some embodiments, the introducer comprises a tapered interior surface for radially compressing an implant that is advanced therethrough. In one embodiment, the tapered interior portion of the introducer is located along the proximal end of the introducer. In one embodiment, the tapered interior portion of the introducer is located along the distal end of the introducer.

BRIEF DESCRIPTION OF THE DRAWINGS

These and other features, aspects and advantages of the present application are described with reference to drawings of certain embodiments, which are intended to illustrate, but not to limit, the various inventions disclosed herein. It is to be understood that the attached drawings are for the purpose of illustrating concepts and embodiments of the present application and may not be to scale.

FIG. 11C illustrates a side view of the tissue removal tool embodiment of FIGS. 11A and 11B;

FIG. 11D illustrates an exploded perspective view of the tissue removal tool embodiment of FIGS. 11A and 11B;

FIG. 12B illustrates a side view of the introducer of FIG. 12A;

FIG. 12C illustrates a longitudinal cross-sectional view of the introducer of FIG. 12A;

FIG. 13A illustrates a distal end view of the introducer of FIG. 12A;

FIG. 13B illustrates a detailed view along the neck portion of the introducer depicted in FIG. 12A;

FIG. 16C illustrates a cross-sectional view of the delivery tool of FIG. 16A;

DETAILED DESCRIPTION

Figure 1:
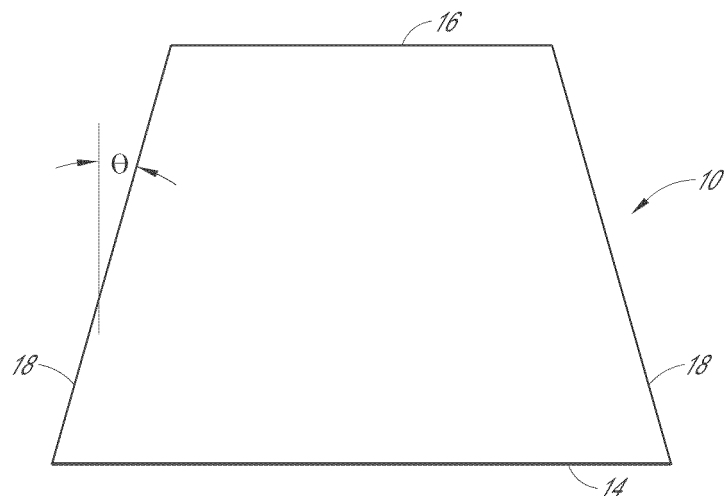
FIG. 1 schematically illustrates a side view of a tapered implant according to one embodiment.

The discussion and the figures illustrated and referenced herein describe various embodiments of a tool for creating a reverse tapered or wedge shaped opening or recess within bone or other tissue of a subject. The tool can be used to safely and efficiently create a wedge shaped opening by radially deploying one or more cutters of a cutting portion located at the distal end of the tool. In some embodiments, the tool is positioned within a cylindrical opening prior to deploying the cutters. In some embodiments, the tool includes an inner member that is configured to engage an outer member and is configured to be moved within an interior of the outer member to selectively radially expand the cutters. Once the cutters are radially expanded, the tool can be rotated so the cutters can remove adjacent tissue to create the wedge shaped recess or opening. In some embodiments, the tool can be rotated manually by the user (e.g., without the use of a drill or other motorized device). In some embodiments, the tool is configured to create a wedge shaped opening with walls that are angled (e.g. relative to the longitudinal axis of the opening) with a similar angle as an implant that will be subsequently secured within the opening. An introducer can be used to position an wedge shaped implant within the opening created by the tool In several embodiments, a system or kit comprising one or more tools, one or more introducers and/or one or more implants is provided.

A number of the devices, systems and associated treatment methods disclosed herein are particularly well suited to replace deteriorated or otherwise damaged cartilage within a joint. Accordingly, such embodiments can be used to treat osteoarthritis, rheumatoid arthritis, other inflammatory diseases, generalized joint pain and/or other joint diseases. However, the various devices, systems, methods and other features of the embodiments disclosed herein may be utilized or applied to other types of apparatuses, systems, procedures and/or methods, including arrangements that have non-medical benefits or applications.

According to several embodiments, implants are configured to remain within the patient's joint on a long-term basis (e.g., for most or all of the life of the patient), and as such, are configured, in some embodiments, to replace native cartilage. Thus, in some embodiments, the implants are configured to be substantially non-biodegradable and/or non-erodable. In some embodiments, for example, an implant is configured to remain within the patient's joint or other portion of the anatomy for a minimum of 10 to 100 years or more (e.g., about 20, 25, 30, 35, 40, 45, 50, 55, 60, 65, 70, 75, 80, 85, 90, 95, 100 years, durations between the foregoing values, etc.) without losing its structural and/or physical properties and/or without losing its ability to function as a cartilage replacement component or device. Accordingly, such embodiments can be used to treat osteoarthritis, rheumatoid arthritis, other inflammatory diseases, generalized joint pain and/or other joint diseases. However, the various devices, systems, methods and other features of the embodiments disclosed herein may be utilized or applied to other types of apparatuses, systems, procedures and/or methods, including arrangements that have non-medical benefits or applications. Implants may be provided with or without an accompanying tool. Implants, which in some embodiments are provided with one or more tools described herein, are also disclosed in US Publ. No 2013/0006368, filed on May 24, 2012 as U.S. application Ser. No. 13/480,272 and published on Jan. 3, 2013, which is hereby incorporated by reference in its entirety.

FIG. 1 schematically illustrates one embodiment of an implant 10 intended for placement within or near a joint of a patient (e.g., toe, finger, ankle, knee, hip, shoulder, etc.). As shown, the implant 10 can include a generally tapered overall shape, wherein its base surface 14 is larger than the opposite, top surface 16. As discussed in greater detail below, the smaller, top surface 16 can comprise the articulation surface (e.g., a surface that is at least partially exposed to a joint), whereas the larger bottom or base surface 14 is securely retained within a corresponding opening specially created in the anatomy (e.g., through bone, cartilage, other native tissue, etc.). As a result of such a design, the sides 18 of the implant 10 can comprise a taper angle θ (e.g., relative to generally vertical sides), thereby giving the implant a generally truncated cone or frustum-like shape. As discussed in greater detail herein, such a reverse-taper, wedge or truncated cone shape can help ensure proper securement of the implant 10 within a patient's anatomy.

Figure 2:
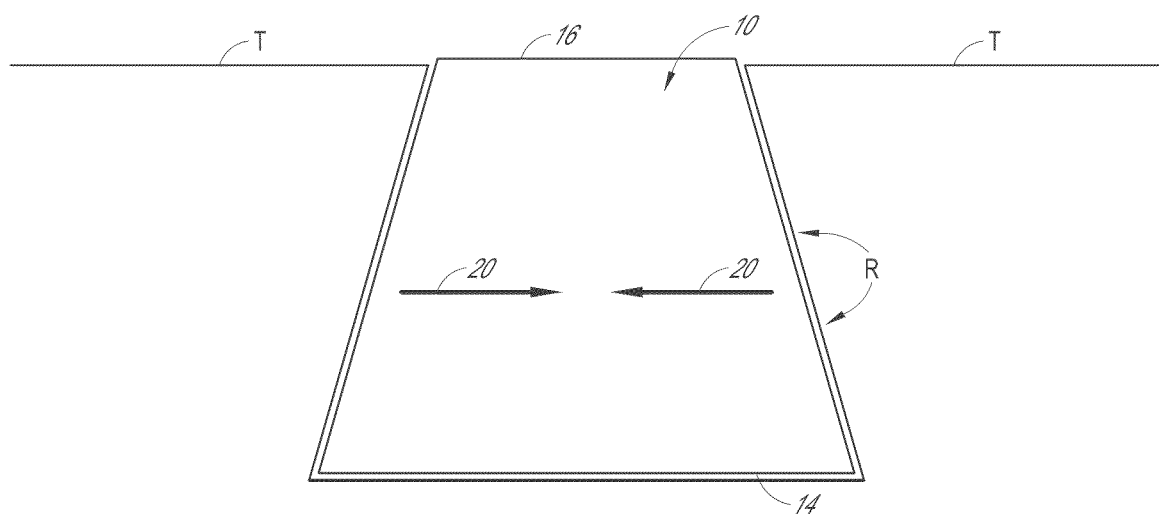
FIG. 2 schematically illustrates a side view of the implant of FIG. 1 positioned within a corresponding implant site, according to one embodiment.

FIG. 2 schematically illustrates an implant 10 similar to the one depicted in FIG. 1 snugly positioned within a corresponding recessed area R of a patient's tissue T (e.g., bone, cartilage, etc.). In some embodiments, such a recessed area R is formed at or near the patient's joint so that the implant 10 can be used to replace and/or augment damaged cartilage (e.g., on a long-term or permanent basis, as discussed above). Alternatively, however, the implant 10 can be positioned generally away from a joint or other articulation surface. Thus, any of the implant embodiments disclosed herein, or equivalents thereof, can be used in a human or animal anatomy for a variety of different indications or other purposes, such as, for example, joint therapy, reconstructive surgery, tissue augmentation, cosmetic surgery and/or the like. For any of the embodiments disclosed herein, or equivalents thereof, the implant 10 can be load bearing or non-load bearing, as desired or required. In some embodiments, once implanted within the anatomy, the implant 10 is configured to be non-biodegradable for at least the expected useful life of the implant 10. In some embodiments, the implant 10 is adapted to generally retain its general structure, shape, structure, size, strength, compressibility, function and/or other properties during the life of the patient into which the implant is inserted. For example, the implant 10 can be configured to generally maintain its original physical, chemical, biocompatibility and/or characteristics for at least about 100 years. In some embodiments, the implant retains the same or substantially the same water content, resiliency, durability, strength, coefficient of friction and/or any other properties for the period of time that it is positioned within the anatomy of the patient. In other embodiments, the implant 10 is configured to generally maintain its original physical, chemical, biocompatibility and/or characteristics for less or more than about 100 years (e.g., about 50 years, 60 years, 70 years, 80 years, 90 years, 110 years, 120 years, 130 years, 150 years, 200 years, more than about 200 years, less than about 50 years, etc.), as desired or required. In some embodiments, the implant 10 is configured to resist or substantially resist biodegradation or mass reduction during such target time period.

With continued reference to FIG. 2, during delivery of the implant 10 within the recess, the implant 10 can be compressed inwardly (e.g., as schematically depicted by the arrows 20). At least some methods of delivering such implants within an appropriately sized and shaped recess are discussed in greater detail herein. In some embodiments, once the implant 10 has been properly positioned within the recess R, the implant 10 is permitted to expand outwardly, thereby filling in or otherwise encompassing all or substantially all of the volume of the recess R. In some embodiments, the diameter or other cross-sectional dimension of the base 14 of the implant 10 is greater than the corresponding diameter or other cross-sectional dimension of the recess R. This helps prevent the implant 10 from moving out of the recess after implantation. The reverse tapered shape of the implant 10 and the recess R into which it is placed can help ensure that implant 10 remains securely within the recess R following implantation. In some embodiments, the outwardly directed forces of the implant 10 in the direction of the adjacent interior surfaces of the recess R assist in maintaining the implant 10 within the recess R during use (e.g., after implantation).

According to some embodiments, the base (or bottom) 14 and/or the top 16 of the implant 10 is generally circular. Alternatively, the shape of the ends 14, 16 can be different than circular, such as, for example, oval, square, other rectangular, other polygonal, irregular and/or the like. Further, once securely implanted in a patient's anatomy (e.g., within a recess R), the top 16 of the implant 10 can be generally flush with the adjacent tissue surface. However, in other embodiments, the top 16 of the implant 10 extends above the adjacent tissue T (e.g., as illustrated in FIG. 2) or below the adjacent tissue T following implantation. For example, in one embodiment, the top 16 of the implant is slightly "proud" or raised relative to the adjacent tissue (e.g., cartilage) in order to reestablish a desired contour of the damaged joint surface. In some embodiments, such a raised or otherwise protruding configuration can assist in creating a smoother transition between the exposed surface of the implant 10 and adjacent native cartilaginous surfaces of a joint.

The top and/or bottom surfaces 16, 14 of the implant 10 can be generally flat or planar. In other embodiments, the surface 16, 14 can be non-planar (e.g., curved, domed, convex, concave, fluted, ridged, etc.), as desired or required. The shape of the top and/or bottom surfaces can be selected based on a patient's anatomy, the location within the patient's anatomy in which the implant will be placed and/or one or more other factors or considerations. For example, the implant can be configured to generally or specifically match the slopes, contours and/or other features of the patient's existing cartilaginous and/or bone tissue, the recess and/or the like. Accordingly, the function of a rehabilitated joint or other targeted anatomical region being treated can be improved.

Figure 3A:
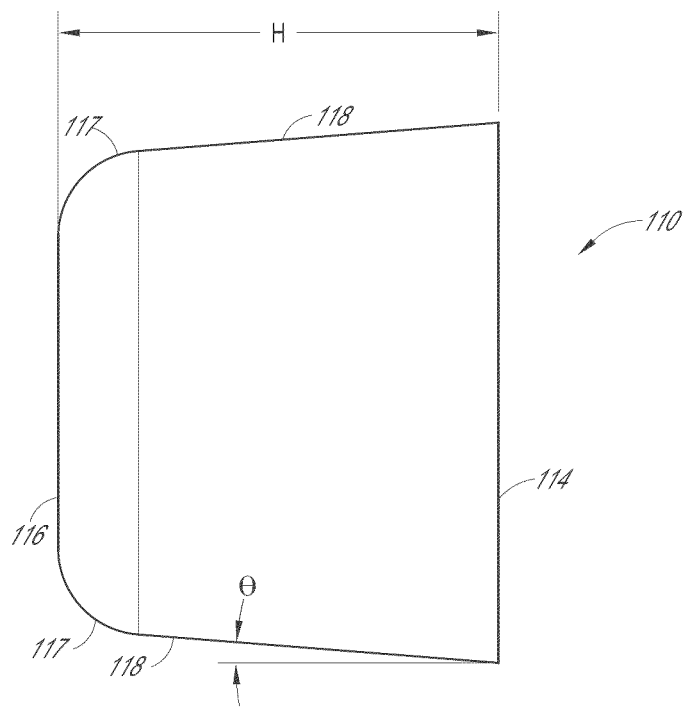
FIG. 3A illustrates a side view of a tapered implant according to one embodiment.
Figure 3B:
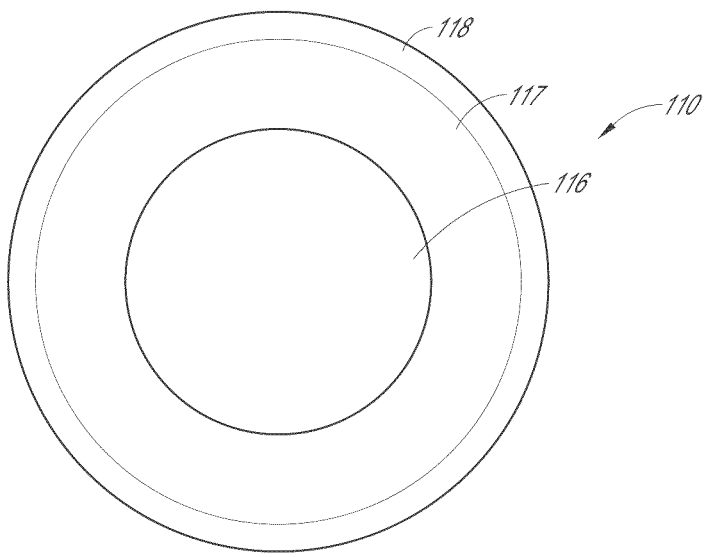
FIG. 3B illustrates a top view of the tapered implant of FIG. 3A.

Another embodiment of a tapered implant 110 configured to replace or augment damaged cartilage within a patient is illustrated in FIGS. 3A and 3B. As shown, the implant 110 can comprise a bottom or base surface 114 and a top surface 116, which is at least partially exposed to adjacent anatomical tissues (e.g., other cartilaginous surfaces, bone, other portions that function as an articulating surface of a joint, etc.) after implantation. As with the implant of FIGS. 1 and 2, the depicted embodiment includes a base 114 that is generally wider or otherwise larger than the top surface 116. For example, the diameter or other comparable cross-sectional dimension of the base can be larger than that of the top. Accordingly, the implant 110 can include generally sloped sides 118 that terminate in a top surface 116 of small diameter (or other cross sectional dimension) than that of the base or bottom surface 114. The sloped surfaces can be generally flat or curved, as desired or required. Further, as shown in FIG. 3A, the transition between the sides 118 and the top 116 can be rounded or otherwise smooth. However, the transition from the side surfaces 118 to the top 116 of the implant 110 can be more or less smooth than illustrated in FIG. 3A. In other words, in some embodiments, the radius of the curved corners is larger or smaller than disclosed herein. For example, as schematically illustrated in FIG. 1, an implant can comprise generally sharp transitions between the top surface and the sides.

As discussed herein with reference to FIGS. 1 and 2, the top, bottom and/or side surfaces of the implant 110 can be generally planar (e.g., flat) or non-planar (e.g., curved, concave, convex, undulating, fluted, etc.), as desired or required. Further, although not illustrated in FIG. 3A, the recess or other opening in which the implant 110 will be positioned can include a similar reverse-tapered shape (e.g., having a wider or large base and a smaller top) to help ensure that the implant 110 remains securely in place following implantation. Additional details regarding reverse tapered openings within a patient's anatomy (e.g., bone), including details related to tools and methods that help create such openings, are provided below.

With continued reference to FIGS. 3A and 3B, an implant 110 can include a generally circular or oval cross-sectional shape. Thus, in some embodiments, the implant 110 is generally shaped like a frustum, truncated cone, cylinder and/or the like. However, the overall shape of any of the implants disclosed herein can vary depending on the specific application or use. For example, the shape of the base (or bottom), top and/or any other cross-sectional area of an implant can be generally rectangular (e.g., square), other polygonal, irregular and/or the like.

Regardless of its exact size and shape, the base portion can be larger or wider than the top of the implant in order to help ensure that the implant remains securely positioned within a targeted portion of a patient's anatomy (e.g., a joint) following implantation. For example, in some embodiments, the dimension (or area) of the base or bottom of the implant is approximately 10% to 15% (e.g., about 10%, 11%, 12%, 13%, 14%, 15%, ranges between such values, etc.) longer, wider or otherwise larger than the top of the implant. Thus, in embodiments having generally circular bottom and top surfaces, such as, for example, the implant 110 illustrated in FIGS. 3A and 3B, the diameter of the base or bottom 114 is approximately 10% to 15% (e.g., about 10%, 11%, 12%, 13%, 14%, 15%, ranges between such values, etc.) larger than the diameter of the top 116. In other embodiments, the base 114 can be more than about 15% larger or less than about 10% larger than the top 116, as desired or required. For example, in some embodiments, the diameter (or other cross-sectional dimension) of the base 114 is larger than the diameter (or other cross-sectional diameter) of the top 116 by approximately 1%, 2%, 3%, 4%, 5%, 6%, 7%, 8%, 9%, less than 1%, other values between the foregoing percentages and/or the like. Alternatively, the diameter (or other cross-sectional dimension) of the base 114 is larger than the diameter (or other cross-sectional diameter) of the top 116 by approximately 16%, 17%, 18%, 19%, 20%, 25%, 30%, 35%, 40%, 50%, 60%, more than 60% and/or the like. According to some embodiments, for any of the implant arrangements disclosed herein, the ratio of the diameter (or other cross-sectional dimension) of the base 114 to the diameter (or other cross-sectional dimension) of the top 116 of the implant is between about 1 and about 1.3 (e.g., approximately or more than 1.05, 1.06, 1.07, 1.08, 1.09, 1.1, 1.11, 1.12, 1.13, 1.14, 1.15, 1.16, 1.17, 1.18, 1.19, 1.2, 1.21, 1.22, 1.23, 1.24, 1.25, 1.26, 1.27, 1.28, 1.29, 1.3, values between the foregoing ratios, etc.). In other embodiments, the ratio is between about 1 and 1.05 (e.g., approximately or greater than 1.01, 1.02, 1.03, 1.04, 1.05), or greater than about 1.3 (e.g., approximately or more than 1.3, 1.35, 1.4, 1.45, 1.5, 1.55, 1.6, greater than 1.6, etc.), as desired or required.

As discussed above with reference to the embodiments illustrated in FIGS. 1-3B, an implant having a wedge or reverse tapered design (e.g., an implant having a larger base than top) can help prevent or reduce the likelihood of unintended ejection or other escape from the implant site after implantation. Thus, in some embodiments, the push-out force (e.g., the force necessary to eject or otherwise remove the implant from the implant site) is advantageously increased for wedge shaped implants relative to implants that do not include a wedge or reverse taper design (e.g., cylindrical implants, right angle implants, implants having generally vertical sides, etc.). As a result, the likelihood of maintaining such embodiments within a joint or other part of the anatomy after implantation is advantageously increased.

With continued reference to FIG. 2, the implant can be positioned within a recess or other opening formed within the patient's bone, cartilage or other tissue. As shown, in some embodiments, the implant 10 is sized, shaped and otherwise configured to fill all or most of the volume of the recess R once properly inserted therein. Further, according to some embodiments, the implant is radially oversized relative to the corresponding implant site (e.g., recess, opening, etc.) into which it will be placed. For example, an implant can be radially oversized by approximately 5% to 15% (e.g., about 5%, 6%, 7%, 8%, 9%, 10%, 11%, 12%, 13%, 14%, 15%, other percentages between such values, etc.) relative to the implant site. In alternative embodiments, an implant can be radially oversized by less than about 5% or more than about 15%, as desired or required. In such oversized embodiments, once implanted, the implant can exert a radial or other outwardly directed force on the corresponding recess. In some embodiments, such a configuration can help ensure that the implant remains securely within the recess after implantation. In yet other embodiments, the implant comprises a similar or identical size as the implant site or is generally radially undersized relative to the implant site.

As a result of the shape of the implant and the corresponding implant site (e.g., recess, other opening, etc.), it may be necessary to radially compress the implant (e.g., inwardly, as schematically illustrated by the arrows 20 in FIG. 2) in order to insert the implant within the implant site. Accordingly, one or more introducers or other delivery tools can be used to facilitate the placement of a tapered implant within an implant site. Additional inwardly-directed compressive forces on the tapered implant may be required for implants that are radially oversized relative to the target implant site, as discussed above. The degree to which an implant can be compressed (e.g., circumferentially, radially inwardly, etc.) may depend on one or more factors, properties, characteristics and/or other considerations, such as, for example, implant size, water content, ingredients and other components, strength, elasticity, surrounding temperature, method of manufacturing and/or the like.

According to some embodiments, radial compression of an implant can affect the implant's overall height, the shape or contours of its outer surfaces (e.g., top or articulating surface, base or bottom surface, sides, etc.) and/or one or more other properties or characteristics of the implant. By way of example, in some embodiments, radial compression of an implant causes the height of the implant to increase (e.g., relative to the height of the implant when it is not radially compressed). Consequently, careful consideration may need to be given to the design of the implant based on, among other things, the expected level of radial compression that may occur once the implant has been properly secured within the implant site. Therefore, the amount of radial compression, and thus its effect on the implant's diameter, height, other dimensions, shape and/or other properties, may need to be carefully determined prior to implantation. Otherwise, upon implantation, an implant may not properly align with adjacent cartilage or other tissue surfaces in a joint or other anatomical location.

According to some embodiments, any of the implant embodiments disclosed herein comprise polyvinyl alcohol (PVA) hydrogels. The implants can comprise one or more other materials, either in addition to or in lieu of PVA, such as, for example, other hydrogels, other polymeric materials, other additives and/or the like. In some embodiments, the PVA content of a hydrogel is approximately 40% by weight. However, the PVA content of an implant can be less or more than about 40% by weight (e.g., approximately 10%, 15%, 20%, 25%, 30%, 32%, 34%, 36%, 37%, 38%, 39%, 41%, 42%, 43%, 44%, 46%, 48%, 50%, 55%, 60%, 65%, 70% by weight, less than about 10% by weight, more than about 70% weight, values between the foregoing ranges, etc.), as desired or required.

Further, the implants can comprise water, saline, other liquids, combinations thereof and/or the like. In some embodiments, the use of saline within a hydrogel implant may be preferred over water, because, under certain circumstances, saline can help maintain osmotic balance with surrounding anatomical tissues following implantation. The exact composition of an implant (e.g., PVA or other hydrogel materials, water, saline or other liquids, other additives, etc.) can be selected so as to provide the resulting implant with the desired or required strength, load bearing capacity, compressibility, flexibility, longevity, durability, resilience, coefficient of friction and/or other properties and characteristics.

In several embodiments, the implants disclosed herein are configured for drug delivery and/or are seeded with growth factors and/or cells. In some embodiments, the implants comprise one or more of the following: chondrocytes, growth factors, bone morphogenetic proteins, collagen, hyaluronic acid, nucleic acids, and stem cells. Such factors and/or any other materials included in the implant and selectively delivered to the implant site can help facilitate and promote the long-term fixation of the implant within the joint or other target area of the anatomy.

In some embodiments, the implants disclosed herein are configured for anchoring during implantation. The implant can comprise one or more anchor sites (which may comprise non-hydrogel portions or tabs) to facilitate anchoring (e.g., suturing, stapling, etc.). In one embodiment, the implant is pre-coupled to one or more anchors. Such anchors can comprise removable and/or permanent fixtures. In some embodiments, the anchors are resorbable or otherwise dissolvable after implantation (e.g., following a particular time period, such as, for instance, 1-30 days, 2-30 weeks, 6-12 months, 1-5 years, greater than 5 years, less than 1 day, etc.). In one embodiment, the implant comprises at least one abrasive surface. In one embodiment, the implant comprises one or more adhesive components. In other embodiments, the tapered shape of the implant permits secure implantation without the need for any anchoring or other fixation. In some embodiments, for any of the implants disclosed herein, one or more implant surfaces can be configured to promote bone adhesion by one or more coatings, substances and/or the like and/or by using an appropriate surface texture along the surface(s). For example, the implant surface can be roughened, can include pores (e.g., superficial pores) and/or any other feature, as desired or required.

In some embodiments, the implants disclosed herein are supported or reinforced by a rigid support frame, such as a ceramic or metallic frame. In some embodiments, the implants disclosed herein are supported or reinforced by a flexible or rigid mesh structure. In other embodiments, the implants do not contain any support or reinforcement structure.

Any of the implant embodiments disclosed herein, or equivalents thereof, can be manufactured using freeze/thaw cycling and/or any other production method. For example, a hydrogel formulation comprising water, saline, PVA (and/or other hydrogel materials), other polymeric materials, other additives and/or the like can be heated and/or otherwise treated as part of a freeze/thaw manufacturing process. In one embodiment, a hydrogel solution comprising saline and about 40% PVA by weight is heated to approximately 121° C. under elevated pressure conditions (e.g., to affect dissolution of the polymer). For example, such a solution can be autoclaved in order to facilitate complete or substantially complete dissolution of the PVA in the saline, water and/or other liquid. Next, the temperature and/or pressure of the solution can be lowered to permit entrapped air and/or other gases to escape. In one embodiment, after the autoclaving or similar step, the solution is generally maintained at a temperature of approximately 95° C. and atmospheric pressure for a predetermined time period.

Figure 4:
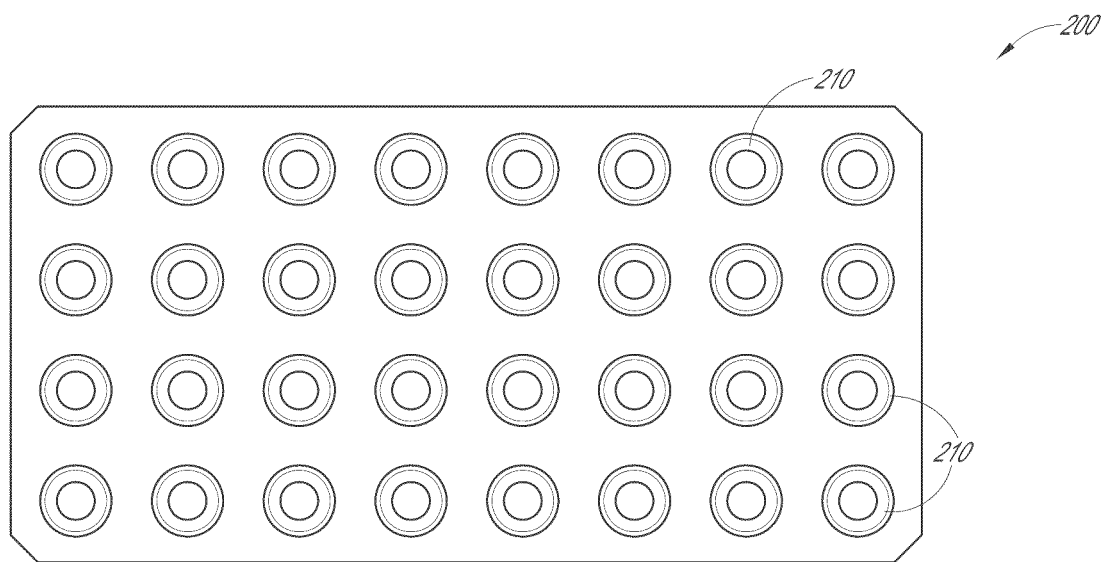
FIG. 4 illustrates a top view of an open mold assembly for making tapered implants, according to one embodiment.
Figure 5:
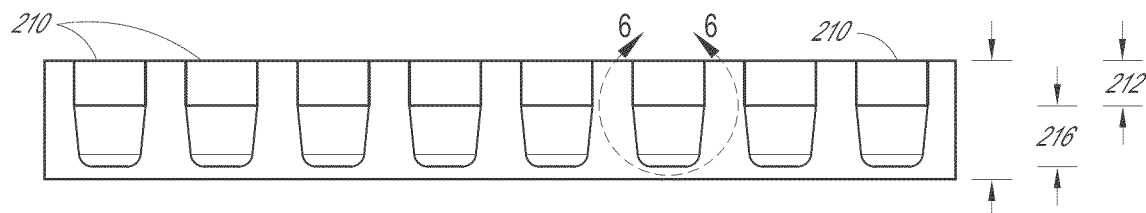
FIGS. 5 and 6 illustrate side views of the mold assembly of FIG. 4.
Figure 6:
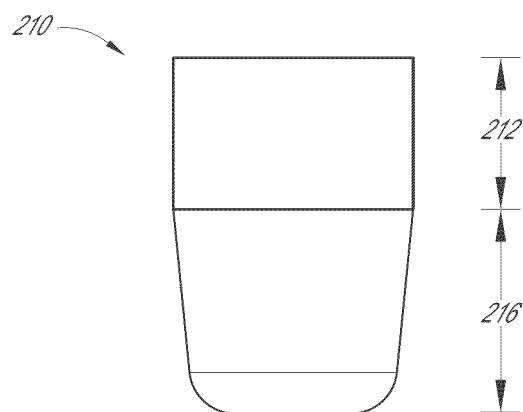

The solution can then be transferred (e.g., pumped, poured, etc.) into open molds where, once set, will form the desired shape of the implants. One embodiment of such an open mold assembly 200 is illustrated in FIGS. 4-6. As shown, the open mold assembly 200 can include a plurality of individual mold cavities 210, each of which is configured to receive a hydrogel solution. With specific reference to the cross sectional views of FIGS. 5 and 6, in some embodiments, the hydrogel solution is configured to fill only a lower portion 216 mold's assembly cavities 210. Alternatively, the cavities can be filled with the desired hydrogel solution to a level that is above the lower portion 216. Accordingly, under such circumstances, the resulting device that is formed therein will extend into the upper portion 212 of the cavity 210. As described in greater detail below, any part of the device that extends above the lower portion 216 can be removed in order to produce an implant having generally sloped or contoured side walls and a reverse tapered design, in accordance with various implant arrangements disclosed herein.

With continued reference to FIGS. 4-6, the cavities 210 of the mold assembly 200 can be shaped, sized and otherwise configured so that the implants formed therein comprise a wedge, truncated cone or reverse taper design. For example, in such designs, the base ends of the implants are generally larger than the corresponding, opposite top ends. Once the implants have been molded, they can be removed from the upper ends of the assembly 200. The molded items can be removed either after initial formation or after they undergo additional treatment (e.g., freeze/thaw cycling, other heat and/or pressure treatment, etc.). As noted above, depending on how much hydrogel solution is placed in the cavities, the molded implants removed from the cavities 210 of the assembly 200 may need to be cut, altered or otherwise processed. For example, in some embodiments, any portion of the implants formed by the generally cylindrical cavity section in the upper portion 212 of the cavities may need to be excised and discarded as part of a subsequent reshaping step. Accordingly, the remaining implants can generally resemble the shape of the implant embodiment of FIGS. 3A and 3B or any other implant having a generally reverse taper or wedge design.

Due in part to the remaining production steps, accommodation of any changes in size (e.g., expansion, contraction, etc.) that may occur or are likely to occur to the implants can be considered during manufacturing by properly sizing and otherwise designing the mold assembly 200. The amount of contraction or expansion of the implants can be based on one or more factors or conditions, such as, for example, the number of freeze/thaw cycles to which the implants are subjected, the temperature and/or pressure ranges associated with the remaining steps and/or the like.

Alternatively, the implants can be formed, at least in part, using an injection molding process and/or any other molding or casting procedure. In such injection or transfer molding techniques, once the hydrogel or other implant solution has been prepared, it can be loaded into an injection cylinder or other container of a molding press. The solution can then be forcibly transferred into a closed mold assembly using a pneumatic or hydraulic ram or any other electromechanical device, system or method. In some embodiments, the hydrogel and/or other solution or implant component is injected into a corresponding closed mold assembly through a standard runner and gate system. Injection molding of implants can provide one or more benefits relative to open mold assemblies. For instance, the devices formed as part of the injection molding techniques typically do not require additional cutting, reshaping, resizing and/or processing, as they are essentially in their final shape immediately after the injection molding step has been completed.

Regardless of how the implants are molded or otherwise shaped or manufactured, they can be subsequently subjected to one or more freeze/thaw cycles, as desired or required. In some embodiments, for example, the implants, while in their respective mold cavities, are cooled using a total of four freeze/thaw cycles wherein the temperature is sequentially varied between approximately −20° C. and 20° C. In other embodiments, however, the number of freeze/thaw cycles, the temperature fluctuation and/or other details related to cooling the implants can be different than disclosed herein, in accordance with a specific production protocol or implant design.

Following freeze/thaw cycling, the implants can be removed from their respective mold cavities and placed in one or more saline and/or other fluid (e.g., other liquid) baths where they can be subjected to additional cooling and/or other treatment procedures (e.g., to further stabilize the physical properties of the implants). According to some embodiments, for instance, the implants undergo an additional eight freeze/thaw cycles while in saline. In other embodiments, such follow-up cooling procedures are either different (e.g., more or fewer freeze/thaw cycles, different type of bath, etc.) or altogether eliminated from the production process, as desired or required.

When the cooling (e.g., freeze/thaw cycling) and/or other treatment steps have been completed, the implants can be inspected to ensure that they do not include any manufacturing flaws or other defects. Further, at least some of the implants can be subjected to selective testing to ensure that they comprise the requisite physical and other characteristics, in accordance with the original design goals and target parameters for the implants. Further, it may be necessary to cut or otherwise process the implants in order to remove any excess portions. In some embodiments, the completed implants are packaged in hermetically sealed plastic trays (or other containers) comprising foil or other types of lids or covering members. A volume of saline and/or other liquid can be included within such trays or other containers to ensure proper hydration of the implants during storage and/or any other steps preceding actual use. In one embodiment, the implant trays or other containers are terminally sterilized using e-beam exposure between about 25 and 40 kGy. Additional details related to producing hydrogel implants can be found in U.S. Pat. Nos. 5,981,826 and 6,231,605, the entire ties of both of which are hereby incorporated by reference herein.

According to some embodiments the overall height (e.g., between the base or bottom surface and the top or articulating surface) of a tapered implant is approximately 10 mm. Further, the diameter or other cross-sectional dimension along or near the top surface of the implant can be about 10 mm. However, in other embodiments, the height, diameter and/or other dimensions of a wedge-type implant can vary, as desired or required. For example, implants adapted for use in larger joints (e.g., knee, shoulder, hip, etc.) can have a height and/or diameter larger than 10 mm (e.g., about 11 mm, 12 mm, 13 mm, 14 mm, 15 mm, 16 mm, 18 mm, 20 mm, greater than 20 mm, dimensions between the foregoing values, etc.). Likewise, implants configured for use in smaller joints (e.g., toes) can be smaller than 10 mm in height (e.g., about 2 mm, 4 mm, 6 mm, 8 mm) and/or 10 mm in top diameter (e.g., about 2 mm, 4 mm, 6 mm, 8 mm).

As discussed above with reference to FIGS. 1 and 2, in order to ensure that the implant securely remains within a joint or other anatomical location following implantation, the implant can be positioned within an implant site that also comprises a similar reverse taper, wedge or truncated cone shape. Accordingly, several embodiments of making such a tapered recess or other opening within bone tissue are described in greater detail below.

Figure 7A:
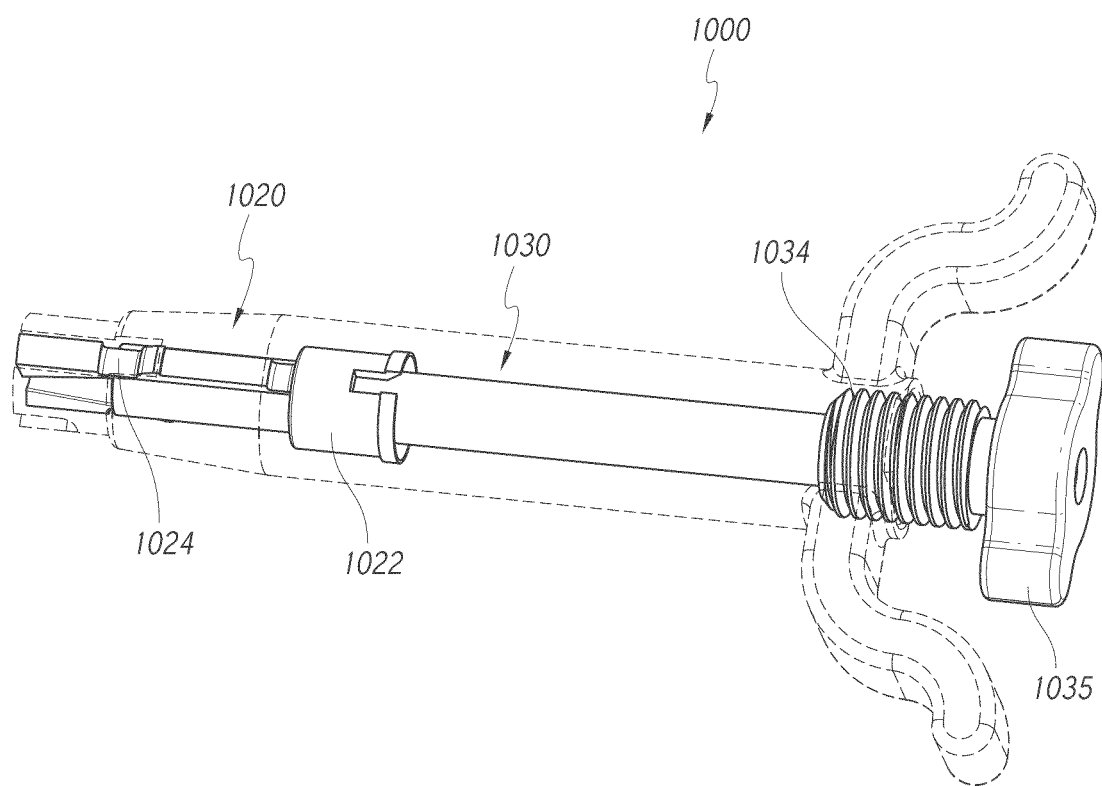
FIG. 7A illustrates a partial perspective view of one embodiment of a tissue removal tool used to create a reverse tapered opening within tissue.
Figure 7B:
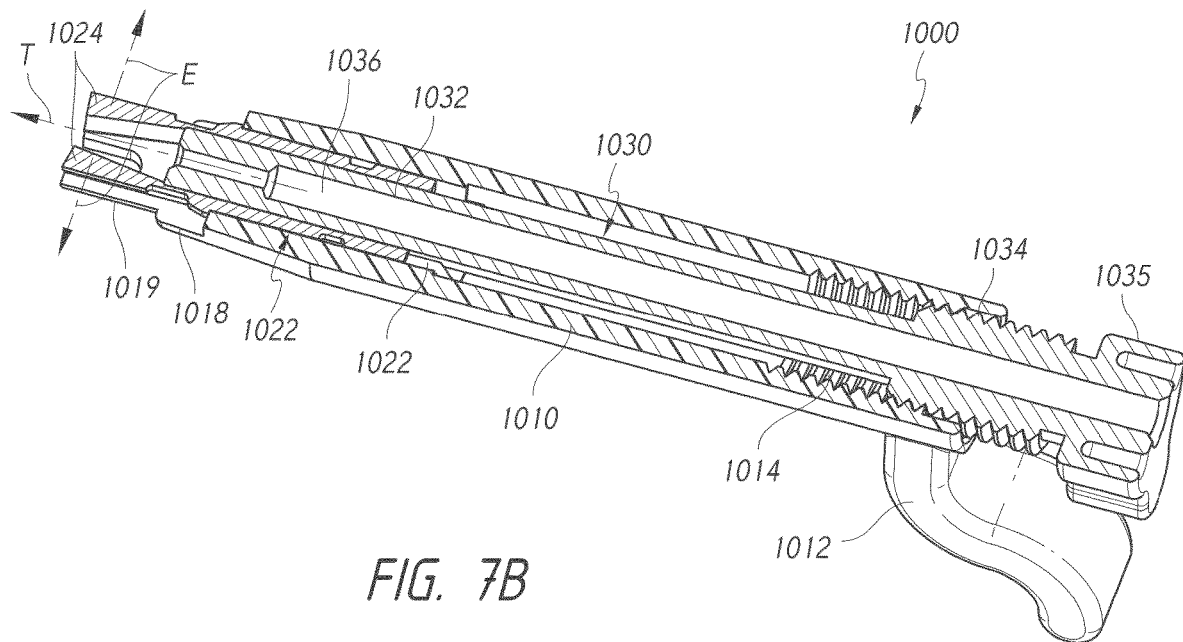
FIG. 7B illustrates a longitudinal cross-sectional view of the tissue removal tool of FIG. 7A.

FIG. 7A illustrates a partial perspective view of one embodiment of a tool 1000 that can be used to create a reverse tapered or wedge-shaped opening within bone or other tissue. In FIG. 7A, an outer tube or member is not shown for clarity. FIG. 7B illustrates a longitudinal cross-sectional view of the tool 1000. As shown in FIGS. 7A and 7B, the tool 1000 comprises an inner member 1030 that engages an outer member 1010. In the illustrated embodiment, the proximal end of the inner member 1030 comprises a threaded portion 1034 that is sized, shaped and otherwise configured to engage a corresponding threaded portion 1014 of the outer member 1010. Thus, as discussed in greater detail herein, the inner member 1030 can be predictably and securely positioned within and advanced relative to the outer member 1010 during use. In other embodiments, the inner member and the outer member include one or more other features that help couple and/or otherwise engage one another and/or that help selectively advance the inner member 1030 relative to the outer member 1010. For example, the outer and inner members 1010, 1030 can include protruding and corresponding recesses, other mechanical engagement features, one or more couplings, one or more alignment members or features and/or the like, either in lieu of or in addition to threaded portions or sections, as desired or required.

As discussed in greater detail herein, the use of a tool, such as the one illustrated in FIGS. 7A and 7B, can facilitate the creation of a reverse tapered or wedge opening within a targeted bone or other anatomical tissue of a subject. Such an opening can be used to receive a similarly shaped implant (e.g., a hydrogel implant, another cartilage-replacement implant, other synthetic materials, native tissue of a subject, etc.). As noted herein, the use of such openings within bone or other tissue can help ensure that an appropriately shaped implant placed therein will safely and securely remain in place post-implantation. For example, the shape of the opening and the implant will help ensure that the implant is mechanically maintained within the opening without the need for separate securement (e.g., fixation) of the implant to the subject's anatomy.

With continued reference to FIGS. 7A and 7B, the proximal end of the inner member 1030 can include a handle 1035 or other portion that can be grasped and easily manipulated by a surgeon or other user. For example, in some embodiments, in order to threadably engage the inner member 1030 to the outer member 1010, the proximal handle 1035 (and thus, the inner member 1030) is rotated relative the outer member 1030. As a result, the threaded portion 1034 of the inner member 1030 can engage the corresponding threaded pattern 1014 of the outer member, thereby securing the inner member to the outer member. As the handle 1035 is rotated in a first direction (e.g., clockwise) relative to the outer member 1010, the inner member 1030 can be longitudinally or axially advanced within the outer member 1010 (e.g., in a distal direction). Likewise, in order to longitudinally retract the inner member 1030 from the outer member 1010, the inner member 1030 can be rotated in a second, opposite direction (e.g., counterclockwise) relative to the outer member 1030. In some embodiments, the threaded patterns 1014, 1034 of the outer and inner members can be oriented in a different direction.

With continued reference to FIG. 7B, the outer member 1010 can further include a proximal handle 1012 that can be grasped and manipulated by a physician or other practitioner during use. As discussed in greater detail herein, the handle 1012 of the outer member 1010 can be used to rotate or otherwise move the entire tool 1000 relative to a subject's tissue (e.g., bone) once the inner member 1030 has been advanced deep enough within the outer member 1010. Such a movement helps excise or remove bone and/or tissue of the subject (e.g., to help create the wedge or reverse tapered shape).

In some embodiments, the inner member 1030 is cannulated or otherwise includes one or more openings (e.g., along its longitudinal or axial centerline). As shown in the longitudinal view of FIG. 7B, a central opening 1036 of the inner member 1030 can extend along the entire length of the inner member 1030, including the proximal handle 1035. Such an opening 1036 can permit the tool 1000 to be placed over a guide pin or other guiding tool to help assist with the accurate positioning of the tool, and thus the creation of a reverse-tapered or wedge opening, during use. In some embodiments, such an opening 1036 can be helpful in removing excised bone tissue that has been cut during a procedure. For example, in some embodiments, a rod or other device can be inserted within the opening 1036 to push bone material distally (e.g., out the distal end of the outer member and the entire tool). In other embodiments, a vacuum or suction force can be applied to the opening 1036 to selectively pull out excised bone and/or other tissue. Such procedure can be performed during, before or after a cutting procedure, as desired or required. In some embodiments, one or more liquids and/or other fluids (e.g., water, saline, medicaments, etc.) can be continuously or intermittently provided through the opening 1036 during use. Such fluids can assist in executing a particular protocol (e.g., to provide a desired degree of moisture or lubrication to facilitate the cutting process and/or the movement of the device during use, etc.).

As depicted in FIGS. 7A and 7B, a cutting portion or cutting member 1020 can be positioned along the distal end of the outer member 1010. In some embodiments, the cutting portion 1020 is secured to the outer member 1010 using one or more attachment devices or methods, such as, for example, a press-fit connection, adhesives, welds, screws, tabs and/or other mechanical fasteners and/or the like. However, in other embodiments, the cutting portion 1020 is a stand-alone component or member that is separate and distinct from the outer member 1010 and/or the inner member 1030. For example, in some embodiments, the cutting member 1020 is configured to be retained within an interior of the outer member 1010 using one or more features (e.g., proximal lip that abuts and stops relative to an adjacent lip or feature along an interior of the outer member 1010, a flange that abuts a corresponding feature of the inner member 1010, etc.). In some embodiments, the cutting portion 1020 comprises two oppositely-positioned cutters 1024 that are configured to be radially expanded during use. However, in other embodiments, the cutting portion 1020 can include more than 2 (e.g., 3, 4, 5, 6, more than 6, etc.) cutters 1024, as desired to required.

Figure 7C:
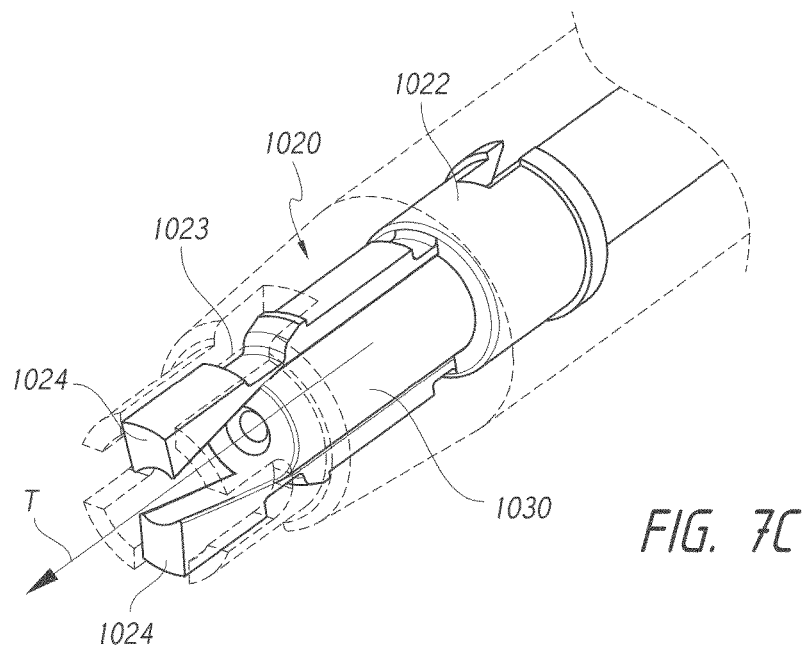
FIG. 7C illustrates a detailed perspective view of the distal end of the tissue removal tool of FIGS. 7A and 7C.
Figure 7D:
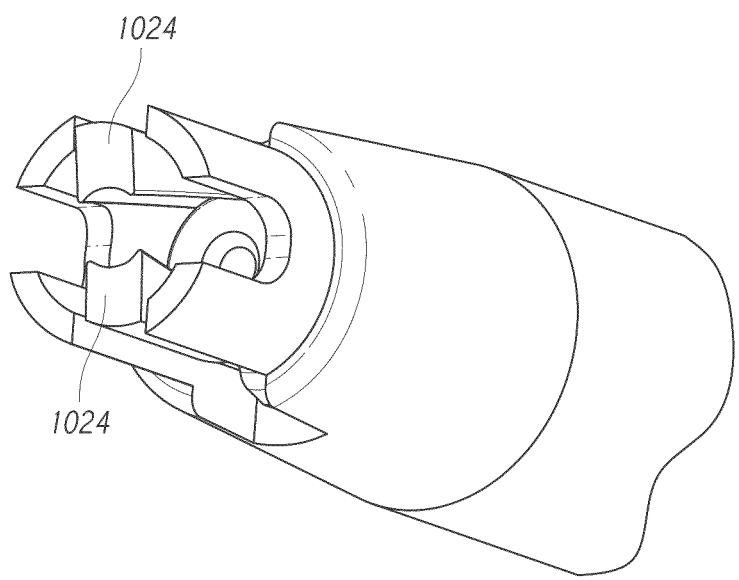
FIG. 7D illustrates a detailed perspective view of tissue removal tool of FIGS. 7A and 7B.

With reference to FIGS. 7B and 7C, each of the cutters 1024 comprises a sloped interior surface (e.g., with the thicker portion located along their distal end of each cutter 1024). As discussed in greater detail herein, such a design can be used to radially expand the cutters 1024 when the inner member 1030 is moved within the interior of the cutting portion 1020 (e.g., in a direction represented by arrow T in FIGS. 7B and 7C).

According to some embodiments, the various components of the tool 1000, including the inner and outer member 1030, 1010 and/or the cutting portion or member 1020 comprise one or more rigid and/or semi-rigid materials that are configured to withstand the forces, moments, chemicals and/or other substances, temperature fluctuations and/or other elements to which they may be exposed. For example, the components of the tool can comprise one or more metals (e.g., stainless steel, other surgical steel, other types of steel, etc.), alloys, plastics and/or the like. Such materials can permit the device to be autoclaved, sterilized or otherwise cleaned during a specific disinfection protocol, and thus, reused for multiple procedures. In some embodiments, the tool 1000 can include polymeric materials and/or other materials that make it more conducive for the tool 1000 to be disposable and/or replaceable after use.

According to some embodiments, the outer and inner members 1010, 1030 comprise, consist of or consist primarily of a polymeric material, such as, for example, medical grade polycarbonate, while the cutting portion 1020 comprises, consists of or consists primarily of a metal and/or alloy, such as, for example, stainless steel. In some embodiments, the outer member 1010 can comprise a two-part construction. For example, in some embodiments, the distal end of the outer member includes an insert comprising a metal and/or alloy (e.g., stainless steel), whereas the proximal portion of the outer member comprises a different material, such as, for example, a polymeric material (e.g., polycarbonate). Such a configuration can help create a lower cost outer member, and thus, tool. In some embodiments, the outer member 1010 and/or any other component of the tool 1000 can be disposable and/or reusable, as desired or required.

In other embodiments, the two or more portions of a multi-part construction for the outer member can comprise the same or similar materials. For example, the embodiment depicted in FIGS. 11A to 11G includes an outer member 2010 comprising a proximal portion 2011A and a distal portion 2011B. In some arrangements, each of the proximal and distal portions 2011A, 2011B of such an outer member 2010 can comprise stainless steel, another metal or alloy and/or any other material. In other configurations, however, the proximal portion 2011A comprises one or more different materials than the distal portion 2011B of the outer member 2010, as desired or required.

Figure 7E:
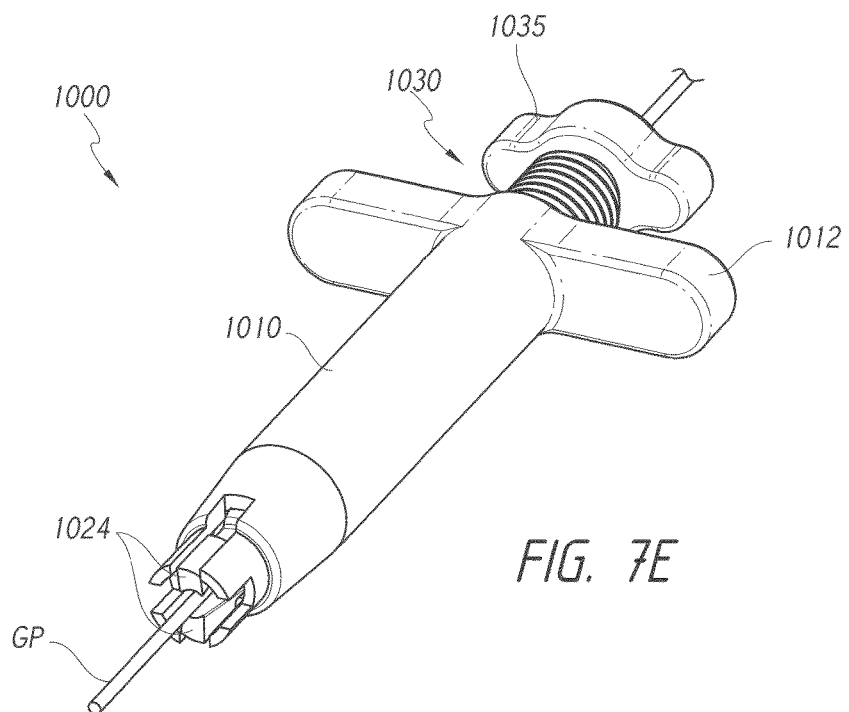
FIGS. 7E to 7G illustrate various views of the tissue removal tool of FIG. 7A.

FIGS. 7E to 10C provide additional views of one embodiment of the tool and its various components. For example, FIG. 7E illustrates a perspective view of the tool 1000 with the inner member 1030 positioned at least partially within the outer member 1010. As depicted in FIG. 7E and discussed in greater detail herein, the tool 1000 can be cannulated in order to permit the tool to be positioned over a guide pin or other guiding member GP. In some embodiments, as described herein, the inner member 1030 can be cannulated such that it includes a central lumen or opening 1036 (see, e.g., FIGS. 7B, 7G, 8C, 11E, etc.). As shown, the lumen or opening along the distal end 1038 of the inner member 1030 can be smaller (e.g., can include a smaller diameter or cross-sectional dimension) than a proximal portion of the lumen or opening 1036. However, in other arrangements, the lumen or opening along the distal end of the inner member can be the same size or larger than a proximal portion of the lumen of opening, as desired or required.

Figure 7F:
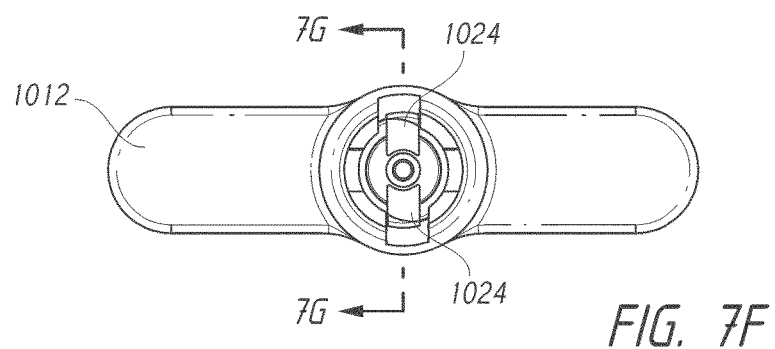
Figure 7G:
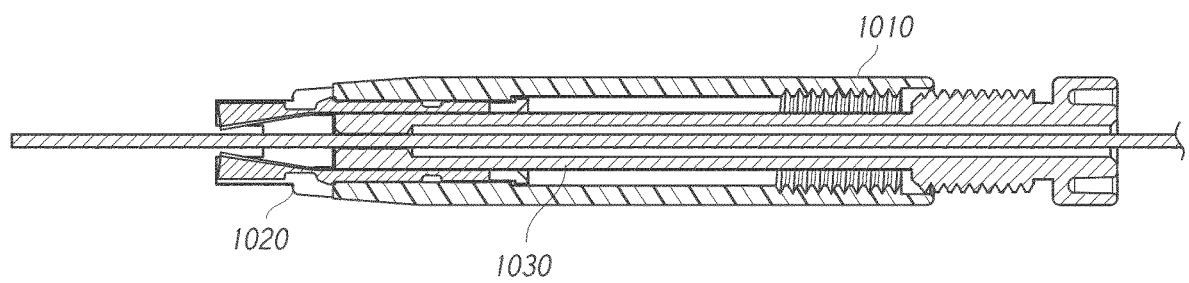

With continued reference to FIGS. 7E to 7F, the distal end of the outer member 1010 can be tapered. For example, as discussed in greater detail herein, such a tapered distal portion of the outer member 1010 can be sized, shaped and configured to fit within a cylindrical opening created within a targeted bone surface or other tissue. In some embodiments, a manually operated tool 1000, 2000 to create a desired wedge or reverse tapered shape within a target bone of subject, in accordance with the arrangements disclosed herein, can be configured to be used after a cylindrical opening or cavity has been created by a separate tool or device. As depicted in the perspective view of FIG. 7E, the distal end of the outer member can include one or more slots or openings through which the cutters 1024 can pass when the cutting portion 1020 is radially expanded (e.g., when the inner member 1030 is advanced sufficiently far enough within an interior of the outer member 1010). One or more additional slots or openings can also be provided along the distal end of the outer member (separate and aside from the slots or openings through which the cutters pass). Such additional slots or openings can assist in receiving excised bone and/or any other native tissue of the subject removed during a procedure.

Figure 8A:
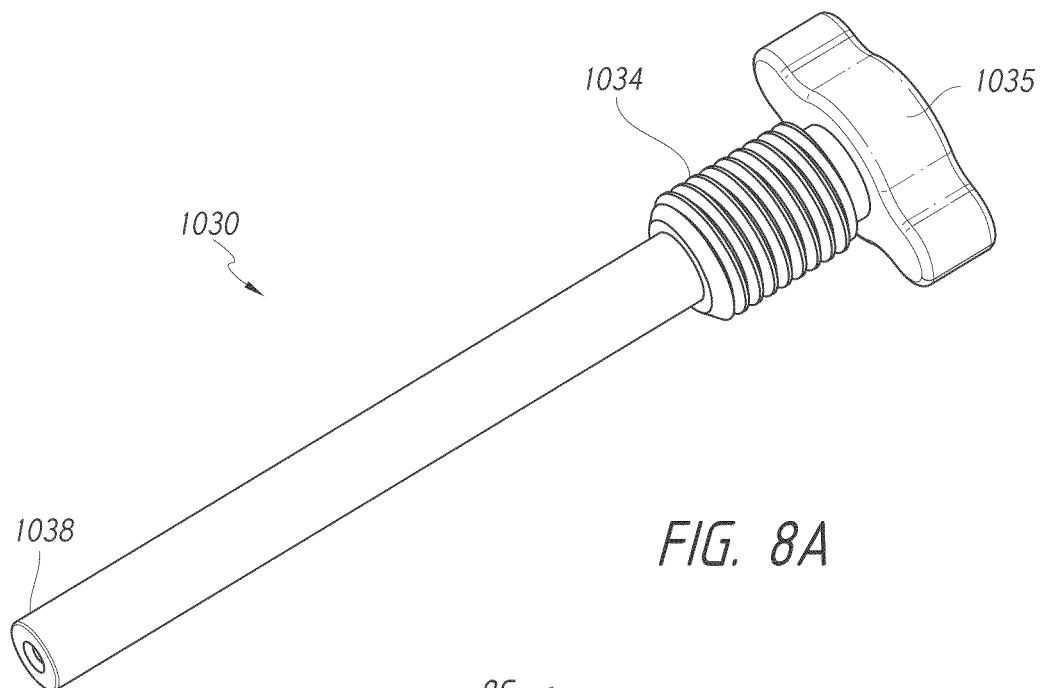
FIGS. 8A to 8C illustrate various views of the inner member of the tissue removal tool of FIG. 7A.
Figure 8B:
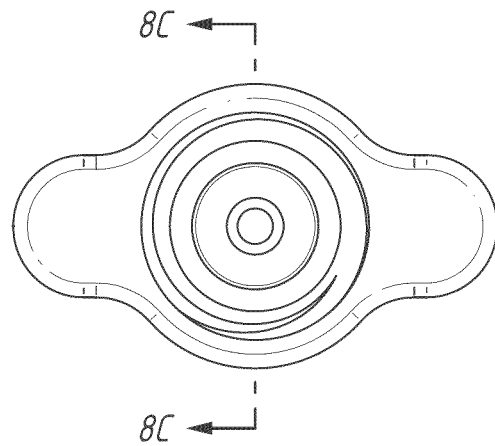
Figure 8C:
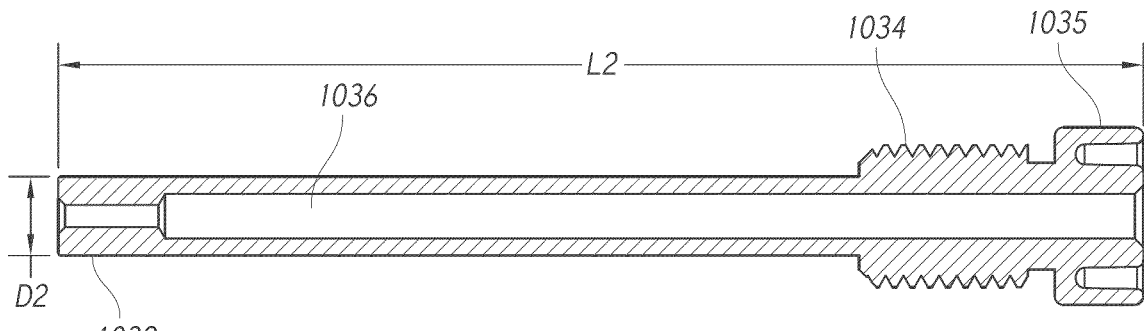

FIGS. 8A to 8C illustrate different views of one embodiment of an inner member 1030 configured for use with a bone or other tissue removal tool 1000. With reference to the longitudinal cross-section view of FIG. 8C, in some embodiments, the length L2 of the inner member 1030 can be between 4 and 6 inches (e.g., 4-4.2, 4.2-4.4, 4.4-4.6, 4.6-4.8, 4.8-5, 5-5.2, 5.2-5.4, 5.4-5.6, 5.6-5.8, 5.8-6 inches, lengths between the foregoing ranges, etc.). In one embodiment, the length L2 of the inner member 1030 is approximately 4.8 inches (122 mm). However, in other embodiments, the length L2 of the inner member 1030 can be less than 4 inches or greater than 6 inches, as desired or required. With continued reference to FIG. 8C, the outer diameter or cross-sectional dimension D2 along the distal end 1038 of the inner member 1030 (as well as the main shaft portion in the depicted embodiment) can be approximately 0.35 inches (8.9 mm). In some embodiments, the outer diameter or cross-sectional dimension D2 along the distal end 1038 of the inner member 1030 is between 0.2 and 0.5 inches (e.g., 0.2-0.25, 0.25-0.3, 0.3-0.35, 0.35-0.4, 0.4-0.45, 0.45-0.5 inches, dimensions between the foregoing ranges, etc.). In other embodiments, the outer diameter or cross-sectional dimension D2 can be less than 0.2 inches or greater than 0.5 inches, as desired or required for a particular tool or application.

Figure 9A:
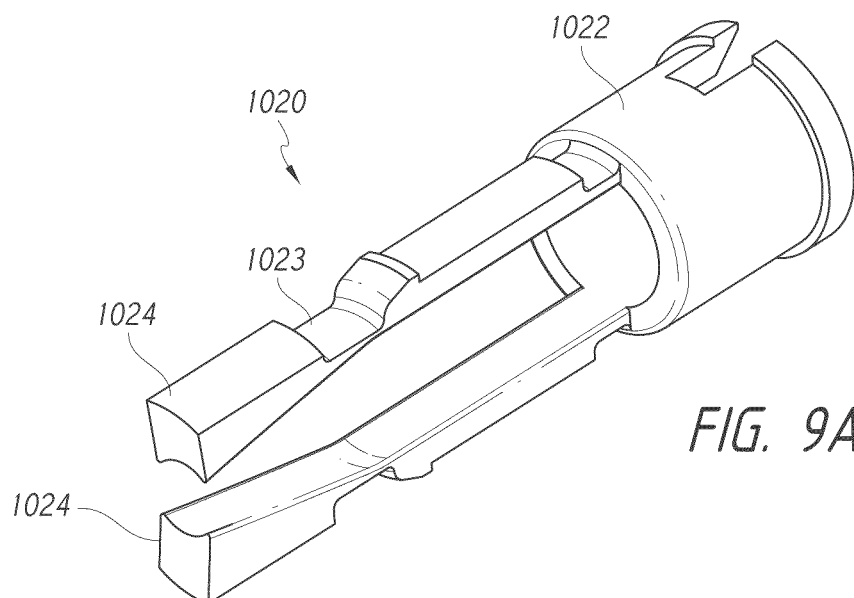
FIGS. 9A to 9C illustrate various views of the cutting portion of the tissue removal tool of FIG. 7A.
Figure 9B:
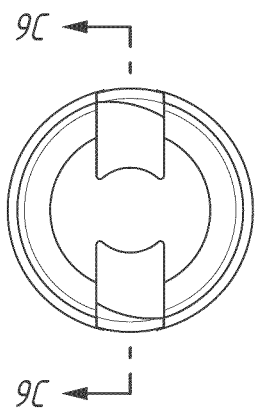
Figure 9C:
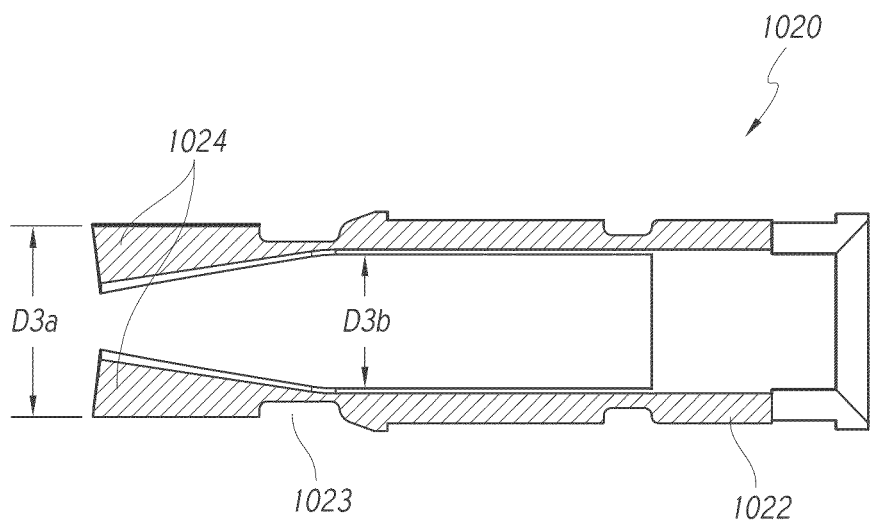

FIGS. 9A to 9C illustrate different views of one embodiment of a cutting portion 1020 configured for use with a tool 1000. As shown and discussed with reference to other figures herein, the cutting portion or cutting member 1020 can include a cylindrical proximal portion 1022 and one or more cutters 1024 that extend distally from the cylindrical portion 1022. In some embodiments, the cutting portion 1020 is sized, designed and otherwise configured to fit within and be secured to the outer member 1010 (see, e.g., FIGS. 7B and 7G). In some embodiments, the cutting portion 1020 is press fit within an interior of the outer member 1010; however, the cutting portion can be secured to the outer member and/or any other component or portion of the tool 1000 using one or more other attachment methods or devices (e.g., adhesives, welds, rivets, fasteners, etc.). In other embodiments, the cutting member 1020 is sized, shaped and otherwise configured to abut one or more surfaces or other portions along the distal end of the outer member 1010. Such a configuration can help maintain the longitudinal location of the cutting portion or member 1020 relative to the outer member 1010, and thus the tool 1000, during use.

With continued reference to FIGS. 9A to 9C, in some embodiments, the cutters 1024 include one or more recesses or other features 1023 along at least a portion of their length. Such recesses or features 1023 can be shaped, sized and otherwise configured to match corresponding features along an interior of the outer member 1010 (e.g. for securing the cutting portion 1020 to the outer member 1010 or otherwise limiting movement between the cutting portion and the outer member). Further, as discussed in greater detail herein, the cutters 1024 can be sloped or otherwise tapered along their interior. In some embodiments, this permits the cutters 1024 to be radially expanded when the inner member 1030 in advanced within an interior of the cutters 1024. The slope or taper along the interior surfaces of the cutters 1024 permits the radial expansion of the cutters to occur gradually. In some embodiments, the cutters 1024 normally assume a retracted shape. Thus, in such embodiments, once an inner member 1030 is withdrawn from an interior of the cutting portion 1020, the cutters 1024 re-assume a retracted orientation. Accordingly, in some embodiments, the cutters 1024 are resiliently biased (e.g., inwardly) and configured to be urged outwardly (e.g., by the passage of distal end of the interior member 1030 through an inner passage of the cutting member 1020) in order to flare out or otherwise expand the distal end of the tool. It is the rotation of the tool in such a flared out configuration that helps create the desired wedge or reverse tapered opening within a targeted bone or other tissue of a subject.

With reference to the longitudinal cross-sectional view of FIG. 9C, in some embodiments, the outer diameter or cross-sectional dimension D3a along the distal end of the cutting portion 1020 (e.g., when the cutters 1024 are radially retracted) is 0.3 to 0.7 inches (e.g., 0.3-0.35, 0.35-0.4, 0.4-0.45, 0.45-0.5, 0.5-0.55, 0.55-0.6, 0.6-0.65, 0.65-0.7 inches, dimensions between the foregoing, etc.). In one embodiment, the outer diameter or cross-sectional dimension D3a along the distal end of the cutting portion 1020 (e.g., when the cutters 1024 are radially retracted) is approximately 0.5 inches (approximately 12.7 mm). Further, in some embodiments, the inner diameter or cross-sectional dimension D3b along an interior of the proximal (e.g., cylindrical) end of the cutting portion 1020 is 0.2 to 0.7 inches (e.g., 0.2-0.25, 0.25-3, 0.3-0.35, 0.35-0.4, 0.4-0.45, 0.45-0.5, 0.5-0.55, 0.55-0.6, 0.6-0.65, 0.65-0.7 inches, dimensions between the foregoing, etc.). In one embodiment, the inner diameter or cross-sectional dimension D3b along an interior of the proximal (e.g., cylindrical) end of the cutting portion 1020 is approximately 0.35 inches (approximately 9 mm).

As discussed herein, when the inner member 1030 is advanced within the interior of the cutting portion or member 1020, the cutters 1024 of the cutting portion or member can be radially expanded. In some embodiments, the cutters 1024 are radially expanded such that their outer diameter or other cross-sectional dimension after full expansion is 30% to 70% (e.g., 30-35, 35-40, 40-45, 45-50, 50-55, 55-60, 60-65, 65-70%, percentages between the foregoing, etc.) greater than their outer diameter or other cross-sectional dimension D3a when retracted. Due to the sloped inner surfaces of the cutters 1024, once fully radially expanded, the cutters 1024 will be angled relative to the longitudinal axis of the tool and relative to the walls of the cylindrical opening. In some embodiments, the angle of the expanded cutters 1024 relative to the longitudinal axis of the cutting portion or member 1020 (and thus, the entire tool 1000) is between 0 and 45 degrees (e.g., 0-1, 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24, 24-25, 25-26, 26-27, 27-28, 28-29, 29-30, 30-31, 31-32, 32-33, 33-34, 34-35, 35-36, 36-37, 37-38, 38-39, 39-40, 40-41, 41-42, 42-43, 43-44, 44-45 degrees, angles between the foregoing, etc.). In other embodiments, such an angle is greater than 45 degrees (e.g., 45-50, 50-55, 55-60 degrees, angles between the foregoing ranges, more than 60 degrees, etc.), as desired or required. The angles of the expanded cutters relative to a longitudinal axis of the tool discussed above can apply to any wedge creation tool embodiments disclosed herein, including, without limitation, the tool 2000 illustrated in FIGS. 11A to 11G.

Figure 10A:
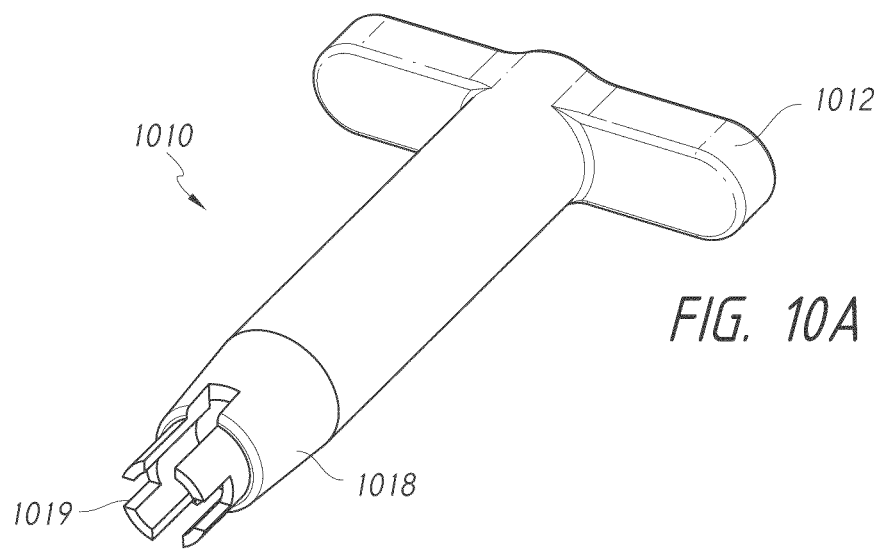
FIGS. 10A to 10C illustrate various views of the outer member of the tissue removal tool of FIG. 7A.
Figure 10B:
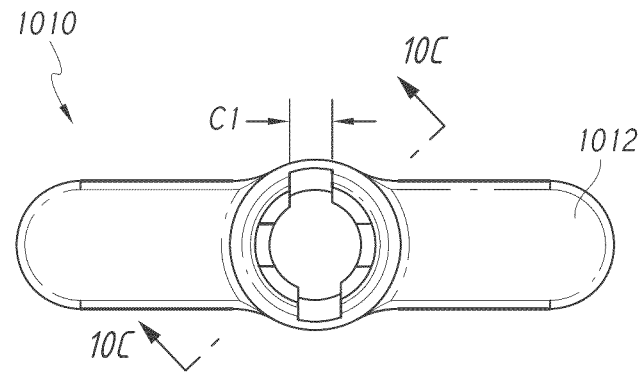
Figure 10C:
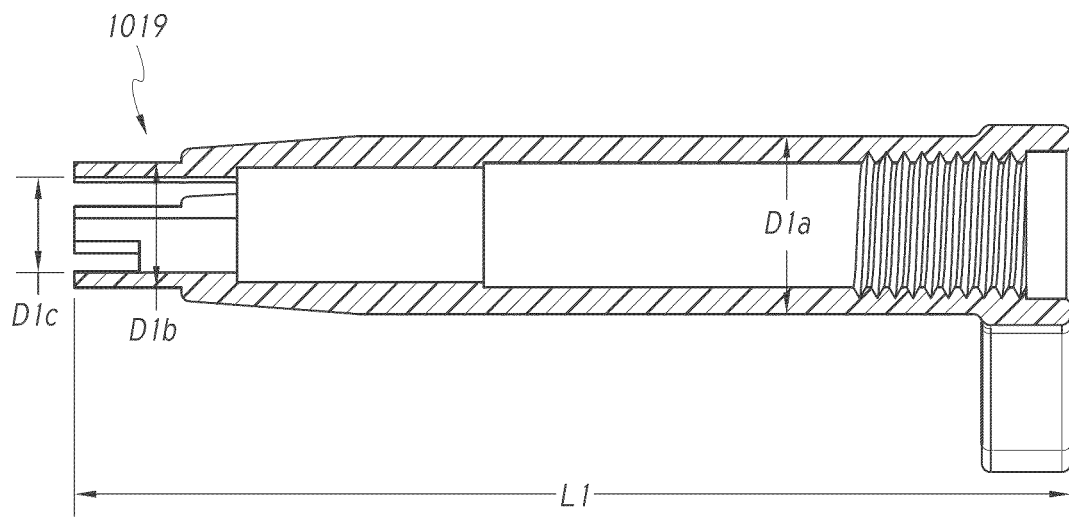

FIGS. 10A to 10C illustrate various views of an outer member 1010 configured for use with a bone or other tissue removal tool 1000. As discussed in greater detail herein, the distal end 1019 of the outer member 1010, and thus the tool 1000, can be tapered (e.g., can include a smaller outer diameter or other cross-sectional dimension) to permit the tool to be positioned within a cylindrical opening or recess of a targeted bone or other anatomical tissue. As noted, for example, the tool 1000 can be configured to be used after another tool has been used to create a cylindrical opening within the targeted bone of the subject. In some embodiments, the distal end 1019 of the outer member 1010 of the tool can include a cylindrical shape that is sized, shaped and otherwise configured to fit within the cylindrical opening created by a first tool (e.g., another manually operated device, a non-manual (e.g., electric, pneumatic, etc.) drill or other tool and/or the like. Thus, as shown in, e.g., FIGS. 7B, 10A and 10C, the distal end of the outer member 1010 can include a tapering feature. In some embodiments, as included in the depicted configuration, such a tapering feature comprises a step or other abrupt feature. However, in other embodiments, any taper included along the distal end of the inner portion 1010 can be gradual (e.g., the distal end of the outer member does not include a step or other abrupt feature), as desired or required.

With continued reference to FIGS. 10A to 10C, as discussed herein, the distal end of the outer member 1010 can include one or more slots or other openings through which the cutters 1024 of the cutting portion 1020 can pass as those cutters are radially expanded. As depicted in FIG. 10B, the size C1 of each opening along distal end of the outer member 1010 is 0.1 to 0.3 inches (e.g., 0.1-0.15, 0.15-0.2, 0.2-0.25, 0.25-0.3 inches, dimensions between the foregoing, etc.). In one embodiment the size C1 of each opening along distal end of the outer member is approximately 0.1 inches (4 mm). As shown in the longitudinal cross-sectional view of FIG. 10C, the length L1 of the outer member 1010 is between 4 and 6 inches (e.g., 4-4.2, 4.2-4.4, 4.4-4.6, 4.6-4.8, 4.8-5, 5-5.2, 5.2-5.4, 5.4-5.6, 5.6-5.8, 5.8-6 inches, lengths between the foregoing ranges, etc.). In one embodiment, the length L1 of the outer member 1010 is approximately 4.4 inches (112 mm). However, in other embodiments, the length L1 of the outer member 1010 can be less than 4 inches or greater than 6 inches, as desired or required.

With continued reference to FIG. 10C, the outer diameter or cross-sectional dimension D1a of the outer member 1010 (e.g., along a proximal end of the outer member) is 0.5 to 1 inches (e.g., 0.5-0.6, 0.6-0.7, 0.7-0.8, 0.8-0.9, 0.9-1 inches, dimensions between the foregoing, etc.). In one embodiment, the outer diameter or cross-sectional dimension D1a of the outer member 1010 (e.g., along a proximal end of the outer member) is approximately 0.8 inches (approximately 20 mm). As illustrated in FIG. 10C and discussed in greater detail herein, in some embodiments, the outer member 1010 is tapered, such that its outer diameter decreases along at least a portion of its distal end. Further, as shown in FIG. 10C, the distal most end 1019 of the outer member 1010 can include a step-like and/or other abrupt feature (e.g., where the diameter of the outer member changes quickly). As discussed herein, in some embodiments, the smaller diameter distal end of the outer member 1010 is sized, shaped and configured to fit within a cylindrical opening that is initially created in the targeted bone or other tissue where the reverse-tapered or wedge opening will be created.

According to some embodiments, the outer diameter or cross sectional dimension D1b of the distal most section 1019 of the outer member 1010 is 0.3 to 0.7 inches (e.g., 0.3-0.4, 0.4-0.5, 0.5-0.6, 0.6-0.7 inches, dimensions between the foregoing, etc.). In one embodiment, the outer diameter or cross sectional dimension D1b of the distal most section 1019 of the outer member 1010 is approximately 0.56 inches (approximately 14.3 mm). However, in other embodiments, the outer diameter or cross sectional dimension D1b of the distal most section 1019 of the outer member 1010 can be less than 0.3 inches or greater than 0.7 inches, as desired or required. In some embodiments, the inner diameter or cross sectional dimension D1c formed by distal most section 1019 of the outer member 1010 is 0.2 to 0.6 inches (e.g., 0.2-0.3, 0.3-0.4, 0.4-0.5, 0.5-0.6 inches, dimensions between the foregoing, etc.). In one embodiment, the inner diameter or cross sectional dimension D1c of the distal most section 1019 of the outer member 1010 is approximately 0.42 inches (approximately 10.7 mm). However, in other embodiments, the inner diameter or cross sectional dimension D1c of the distal most section 1019 of the outer member 1010 can be less than 0.2 inches or greater than 0.6 inches, as desired or required.

The various tool embodiments disclosed herein (e.g., with reference to FIGS. 7A to 11G) can be used to create a reverse-tapered or wedge shaped opening in any bone surface and/or other tissue of a subject. For example, in some embodiments, the tool 1000, 2000 can be used to create an opening in a bone adjacent a subject's knee, shoulder, foot, arm, wrist, hand and/or the like. As discussed in greater detail herein, the tool 1000, 2000 can be used to manually create a reverse-tapered or wedge shaped opening within a bone surface or other targeted tissue of a subject manually (e.g., without the use of a drill or other motorized tool). Thus, the creation of such wedge shaped openings can be made in a safer and more predictable manner by using the tool 1000, 2000 or variations thereof.

According to some embodiments, as a first step of the reverse-tapered or wedge shaped opening, a user creates a cylindrical opening within a targeted bone or other tissue surface of the subject. In order to create such a cylindrical opening, a motorized drill can be used. However, in other embodiments, the cylindrical opening can be created manually and/or using any other device or method. In some embodiments, a tool (e.g., motorized drill, hand or manually-operated drill, etc.) can be cannulated so that it can be predictably and accurately positioned relative to the targeted bone surface using a guide pin or other guiding tool. Thus, in some embodiments, after the targeted bone surface has been prepared for creation of the opening, a guide pin or other guiding device can be accurately positioned on such a targeted surface. A cannulated drill or other device can then be placed over the guide pin or other guiding device and operated so as to create the desired cylindrical opening within the bone or other surface.

According to some embodiments, a first step in creating a reverse tapered or wedge shaped opening within bone or other targeted tissue of a subject includes using a drill bit or other motorized or manual device to create a cylindrical recess or opening. In some arrangements, a bone drill can be used to selectively rotate or otherwise manipulate the drill bit. The bone drill can be either manually operated or power driven (e.g., mechanically, pneumatically, hydraulically, etc.). In some embodiments, such a drill bit can include a flange and one or more abrading members or cutters extending distally from the flange. Such a flange or other feature can ensure that the cylindrical opening is created with a specific depth, as the flange or other feature will prevent further movement of a drill or other device from advancing deeper into targeted bone tissue. In some embodiments, a drill bit can be cannulated, such that one or more passages or openings extend (e.g., longitudinally) through the device. For example, such a passage can generally extend from the proximal end of the drill bit to the distal end, terminating in an opening along a distal hub to which the cutters are secured. The inclusion of such passages or openings can help ensure that the drill bit is accurately positioned within a patient's joint or other portion of the anatomy before commencing a drilling procedure.

In some embodiments, as a drill bit is rotated (e.g., either manually or using one or more external driving sources, etc.), sharp edges formed along the distal and/or peripheral portions of its cutters can abrade and remove cartilage, bone and/or other tissue that they engage and contact. In some embodiments, the longitudinal distance between the distal face of the drill bit's flange member and the distal ends of the cutters can limit the depth of the recess or opening that is created within the patient's bone or other anatomical area. Likewise, the peripheral surfaces of the cutters can define a diameter or other cross-sectional dimension that effectively limits the diameter of the resulting recess or other openings in the patient's bone or other targeted tissue. Thus, the drill bit can be configured to create an implant site having specific dimensions (e.g., depth, diameter, etc.). Consequently, in some arrangements, drill bits of varying size and shape are available to the surgeon or other clinician in order to accurately create a specific desired implant site within the patient.

Once a cylindrical opening has been created to a desired depth, the drill or other device that was used to create the cylindrical opening can be removed. In some embodiments, the depth and diameter of the cylindrical opening is selected based on the size of implant that will be inserted therein. For example, the depth of the cylindrical opening (e.g., relative to the top surface of the bone or other tissue in which the opening is made) can be between 4 and 16 mm (e.g., 4, 5, 6, 7, 8, 9, 10, 11, 12, 13, 14, 15, 16 mm, depths between the foregoing, etc.). However, in other embodiments, the depth can be less than 4 mm (e.g., 0-1, 1-2, 2-3, 3-4 mm, depths between the foregoing, etc.) or greater than 16 mm (e.g., 16-18, 18-20 mm, greater than 20 mm, etc.), as desired or required. Likewise, the diameter or other cross-sectional of the opening can be between 4 and 16 mm (e.g., 4, 5, 6, 7, 8, 9, 10, 11, 12, 13, 14, 15, 16 mm, dimensions between the foregoing, etc.). However, in other embodiments, the diameter can be less than 4 mm (e.g., 0-1, 1-2, 2-3, 3-4 mm, dimensions between the foregoing, etc.) or greater than 16 mm (e.g., 16-18, 18-20 mm, greater than 20 mm, etc.), as desired or required.

Next, in some embodiments, a wedge-creation tool 1000, 2000, in accordance with one or more of the configurations disclosed herein, can be inserted within the cylindrical opening. For instance, in some arrangements, as illustrated in FIGS. 7A-10C, the distal portion of the outer member 1010 can be tapered so that such a tapered portion snugly fits within the cylindrical opening. Thus, in some embodiments, various combinations of depths and diameters of tools 1000 can be manufactured and selectively provided to a user, based, at least in part, on the possible reverse-tapered or wedge opening dimensions desired by such user. In some embodiments, once the distal tapered portion of the outer member 1010 can been properly secured within the cylindrical opening, the user can begin the process of creating the desired wedge shape within such opening. As noted above, in some embodiments, the tool 1000 can be cannulated so that the tool can be accurately and predictably delivered within the desired cylindrical opening over a guide pin or other guiding device.

With continued reference to FIG. 7B, once the distal end of the tool has been properly secured within a cylindrical opening, the user can rotate the proximal handle 1035 of the inner member 1030 to advance the inner member 1030 relative to (e.g., within) the outer member 1010. In some embodiments, the user advances the inner member 1030 fully within the outer member 1010 such that the handle 1035 can no longer be rotated. In some embodiments, as the inner member 1030 is advanced within the outer member 1010, the distal end of the inner member will move within an interior of the cutters 1024 of the cutting member 1020 (e.g., in a direction generally represented in FIGS. 7B and 7C by arrow T). As the distal member moved within the interior of the cutting member 1020, the cutters will be radially expanded by the inner member 1030 (e.g., in a direction generally represented in FIG. 7B by arrows E). As the cutters are forced radially outwardly, they will be forced through adjacent tissue (e.g. bone) along the walls of the cylindrical opening. Due to the sloped inner surfaces of the cutters 1024, once fully radially expanded, the cutters 1024 will be angled relative to the longitudinal axis of the tool and relative to the walls of the cylindrical opening. For example, in some embodiments, the angle of the expanded cutters 1024 relative to the longitudinal axis of the cutting portion or member 1020 (and thus, the entire tool 1000) is between 0 and 45 degrees (e.g., 0-1, 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24, 24-25, 25-26, 26-27, 27-28, 28-29, 29-30, 30-31, 31-32, 32-33, 33-34, 34-35, 35-36, 36-37, 37-38, 38-39, 39-40, 40-41, 41-42, 42-43, 43-44, 44-45 degrees, angles between the foregoing, etc.). In other embodiments, such an angle is greater than 45 degrees (e.g., 45-50, 50-55, 55-60 degrees, angles between the foregoing ranges, more than 60 degrees, etc.), as desired or required. The angles of the expanded cutters relative to a longitudinal axis of the tool discussed above can apply to any wedge creation tool embodiments disclosed herein, including, without limitation, the tool 2000 illustrated in FIGS. 11A to 11G.

In some embodiments, with the cutters 1024 radially expanded, the user can rotate the tool 1000 (e.g., using the handle 1012 of the outer member 1010). Accordingly, the entire tool 1000, including the outer member 1010, the inner member 1030 and the cutting member 1020, can begin to rotate in unison. As the tool 1000 is rotated, the radially expanded cutters 1024 will begin to cut and remove the adjacent tissue (e.g., bone). With sufficient rotation of the tool 1000, a reverse-tapered or wedge shaped opening can be created. In some embodiments, between 1 and 5 revolutions or rotations are required to create the opening. However, in other embodiments, depending on the specific protocol or procedure, the tool 1000 can be rotated less than 1 full revolution or more than 5 full revolutions. In some embodiments, as discussed in greater detail herein with reference to the tool illustrated FIGS. 11A to 11G, rotation of the tool (e.g., rotation of the outer member 1010) can be commenced prior to full expansion of the cutters 1024. In other words, the surgeon or other practitioner can begin to rotate the tool 1000 after partial radial expansion of the cutters 1024 (e.g., when the inner member 1030 has been only partially advanced within the cutting portion or member 1020 of the tool). In some embodiments, the practitioner rotates the tool 1000 at different increments of radial expansion of the cutters 1024. This can advantageously facilitate the cutting or excision of bone tissue as the volume or area of bone tissue that the cutters will need to remove will be reduced at each incremental cutting phase (e.g., when compared to attempting to cut through a larger area of tissue at once by fully extending the cutters 1024 in a single expansion step).

Once the desired reverse tapered or wedge shaped opening has been created (either via incremental radial expansion of the cutters or via a single full expansion step for the cutters), the practitioner or other user can terminate rotation of the tool 1000. In some embodiments, prior to removing the tool from the opening, the user can unthread the inner member 1030 relative to the outer member 1010, thereby causing the inner member to retract from the distal end of the inner member and the tool. As a result, the distal end of the inner member 1030 will move away from the interior of the cutting member 1020, and the cutters 1024 will be permitted to retract inwardly (e.g., as illustrated in FIG. 7B). Thus, the entire tool 1000 can be safely removed from the opening in a manner that will prevent further cutting by the cutters 1024. However, the tool 1000 provides a safety measure in that if the surgeon or other user accidentally removes the tool 1000 prior to retracting the inner member (e.g. when the cutters 1024 are at least partially expanded), only a portion of the anatomical area surrounding the opening will be affected. In other words, since, in some embodiments, the cutters 1024 only partially surround the distal end of the outer member 1010, retraction of at least partially expanded cutters 1024 will only damage the portions of the subject's anatomy through which the cutters 1024 will pass. Thus, the tool 1000 disclosed herein provides a safer manner of creating a wedge shaped opening.

The tool 1000 can be designed and otherwise configured to be manually rotated by the user (e.g., once the cutters 1024 have been radially expanded). This can further enhance the safety of the tool and the related method, as the manual rotation of the tool 1000 is less likely to cause undesirable damage to the targeted anatomical area during use. However, in other embodiments, the tool 1000 can be mechanically coupled to a motorized device (e.g., a drill, another mechanical device, etc.) to assist in the rotation of the tool 1000, and thus, the creation of the opening.

The configuration of the cutting portion or member 1020, 2020 of the embodiments disclosed herein, or variations thereof, can also provide additional benefits and advantages. In some embodiments, since the cutters 1024, 2024 only partially circumscribe or define a periphery of the distal cutting surface, accidental retraction of the tool while the cutters 1024, 2024 are radially expanded will reduce or minimize the damage caused to the native tissue of the subject being treated. For instance, if the practitioner inadvertently withdraws the tool 1000, 2000 while the cutters 1024, 2024 are radially expanded, the damage incurred to the subject's bone tissue will likely be limited to the regions through which the cutters 1024, 2024 pass. In other words, with respect to the cutting members 1020, 2020 disclosed herein, under such accidental circumstances, the cutters 1024, 2024 will move and cut through, and thus at least partially damage, the bone tissue along only two sides of the opening. This is in contrast to cutting tools that include circumferential cutters (e.g., cutters that extend along an entire periphery or nearly an entire periphery) of the device. Retraction of such tools having a larger cutter footprint will severely damage the entire bone region being treated and will likely render such a region incapable of implantation of an implant.

According to some embodiments, as noted herein, the wedge-creation tool 1000, 2000 can be configured to be reusable. In other words, the tool can be designed for sterilization and/or other cleaning procedures between uses or between patients. This can help reduce material costs and can provide one or more additional benefits and advantages. For example, reusing the tool can lower costs to the practitioner or other user or owner. In addition, reuse of the tool can help eliminate waste, thereby providing environmental benefits. However, in other embodiments, as discussed in greater detail herein, one or more components or portions of the tool 1000, 2000 can be disclosable, as desired or required. In fact, in one embodiment, the entire tool can be configured for disposal and replacement after a single use, as desired or required.

FIGS. 11A-11G illustrates various views of another embodiment of a wedge-creation tool 2000 that is similar to other configurations discussed above (e.g., the tool 1000 of FIGS. 7A-10C). As shown in the perspective views of FIGS. 11A and 11B, the tool 2000 can include an outer member 2010 having a two-part construction or design. For example, the outer member 2010 can comprise a proximal portion or section 2011A that is configured to removably couple to a distal portion or section 2011B. As best illustrated in the exploded perspective view of FIG. 11D, the proximal and distal portions or sections 2011A, 2011B of the outer member 2010 can be coupled to each other using a threaded connection. However, in other embodiments, any other type of connection feature or method can be used to removably attach the two portions or sections 2011A, 2011B of the outer member 2010 to one another, such as, for example, friction fit or press fit connections, a flanged connection, a snap fit connection, one or more other types of mechanical connections and/or the like. Further, in some embodiments, the outer member 2010 can include three or more different sections or portions, as desired or required.

Figure 11A:
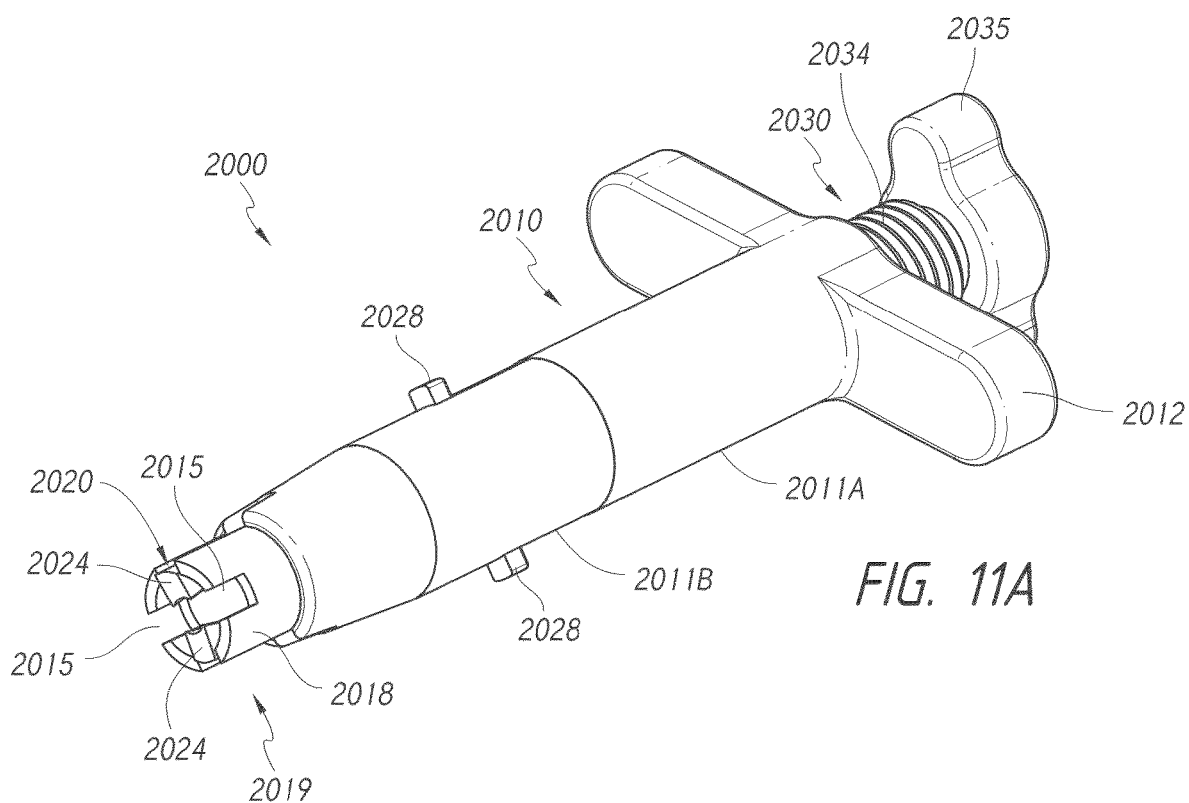
FIGS. 11A and 11B illustrate different perspective views of another embodiment of a tissue removal tool used to create a reverse tapered opening within tissue.
Figure 11B:
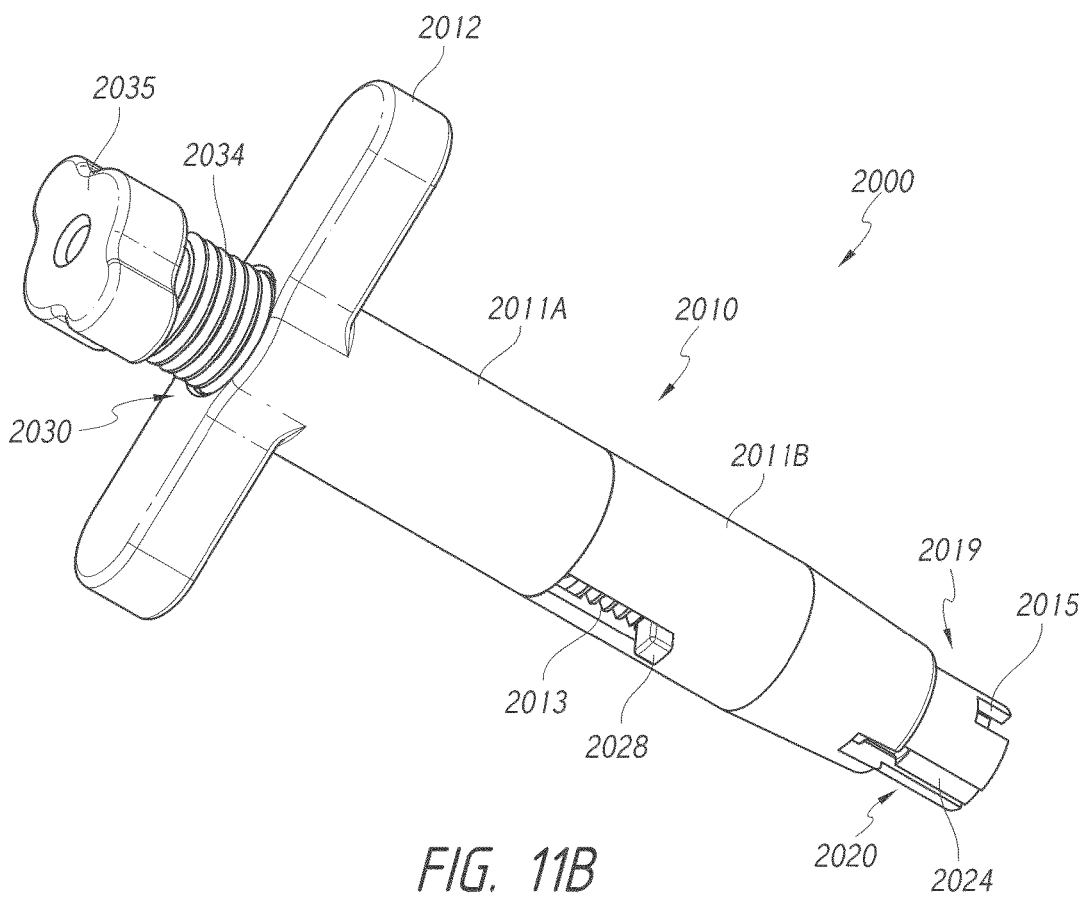
Figure 11E:
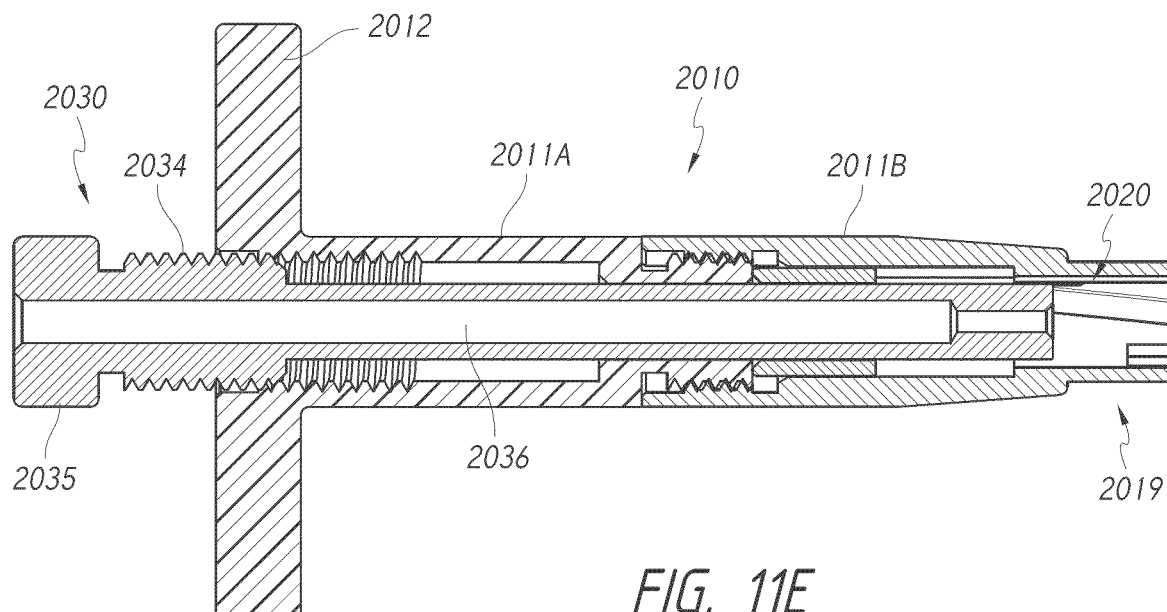
FIG. 11E illustrates a longitudinal cross-sectional view of the tissue removal tool embodiment of FIGS. 11A and 11B.
Figure 11G:
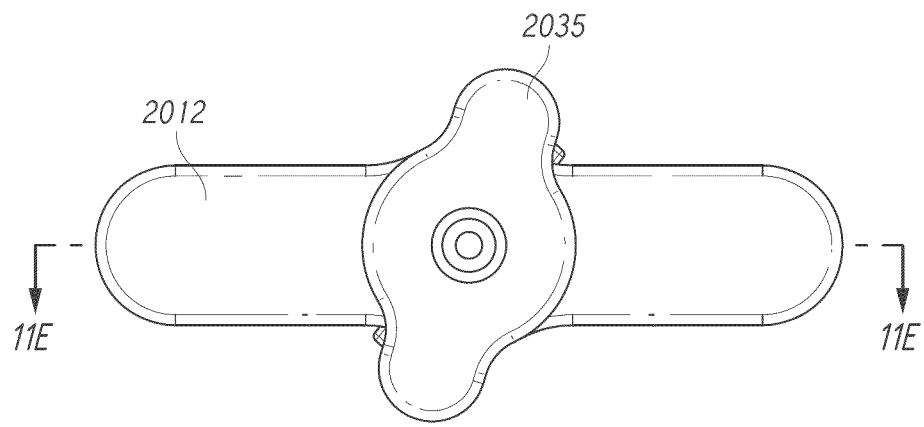
FIGS. 11F and 11G illustrate top and bottom views, respectively, of the tissue removal tool embodiment of FIGS. 11A and 11B.
Figure 11F:
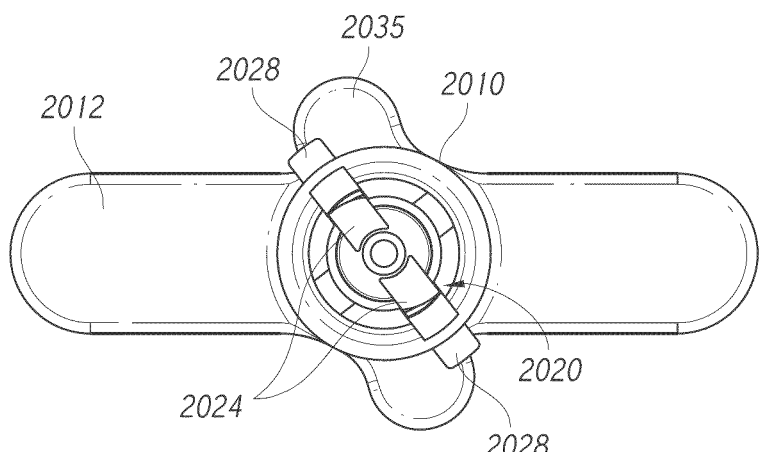
Figure 12A:
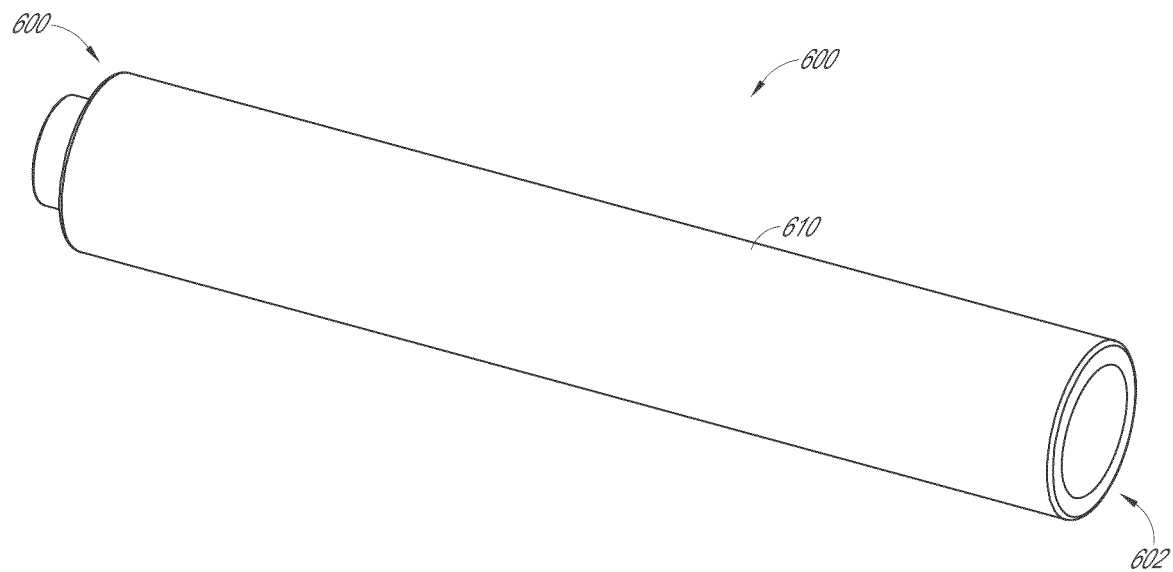
FIG. 12A illustrates a perspective view of an implant introducer according to one embodiment.

With continued reference to FIGS. 11A and 11B, the tool 2000 can include all or some of the features and components discussed herein in relation to the tool 1000 illustrated in FIGS. 7A to 10C. Such features and components include, without limitation, an inner member 2030 and a cutting member or portion 2020. In some embodiments, the inner member 2030 is sized, shaped and configured to threadably engage an interior of the outer member 2010. For instance, as shown in the exploded perspective view of FIG. 11D, the inner member 2030 includes a non-threaded distal shaft 2036 and a threaded portion 2034 that is proximal to the distal shaft 2036. The inner member 2030 can be positioned within a proximal opening of the outer member 2010 (e.g., the proximal portion 2011A of the outer member) and rotated relative to the outer member 2010 so that the threaded portion 2034 of the inner member 2030 engages a corresponding threaded portion along the proximal interior of the outer member 2010.

As discussed herein, once the tool 2000 is fully assembled with the cutting member or portion 2020 secured to the outer member 2010, the continued advancement (e.g., in the distal direction) of the inner member 2030 relative to the interior of the outer member 2010 will move the distal shaft 2036 of the inner member within an interior opening or region of the cutting member or portion 2020. This can cause the cutters 2024 of the cutting member or portion 2020 to radially expand (e.g., so as to create a wedge or reverse tapered shape). Once the cutters 2024 of the cutting member or portion 2020 have been partially or fully radially expanded, rotation of the entire tool 2000 (e.g., via manipulation of the proximal handle 2012 of the outer member 2010) can cause the cutters 2024 to remove bone and other native tissue of the subject along the targeted anatomical site (e.g., a joint) to transform a cylindrical opening or cavity into one that has a wedge shape.

The embodiment of FIGS. 11A-11G is different from the one illustrated in FIGS. 7A to 10C in regard to the manner in which the cutting member or portion 2020 is retained relative to the outer member 2010. As shown in FIG. 11D, the cutting member 2020 can include proximal tabs or other protrusions 2028 that extend laterally or radially outwardly. In the depicted arrangement, the cutting member 2020 comprises two proximal tabs or protrusions 2028; however, in other embodiments, fewer (e.g., 1) or more (e.g., 3, 4, 5, 6, more than 6) tabs or protrusions 2028 can be included in the cutting member 2020. Further, the location, orientation, shape, length and/or any other details of the tabs or other protrusions 2028 of the cutting member 2020 can vary, as desired or required.

With continued reference to FIG. 11D, in some embodiments, the distal portion or section 2011B of the outer member 2010 can include slots or openings 2013 that are shaped, sized and otherwise configured to receive the tabs or protrusions 2028 of the cutting member 2020. Thus, as part of the assembly of the tool 2000 (e.g., after a sterilization procedure and before use), the cutting member 2020 can be inserted within the distal portion 2011B of the outer member 2010 so that the tabs or protrusions 2028 of the cutting member 2020 align with and are able to slide relative to the slots or openings 2013 of the distal portion 2011B of the outer member 2010. After the cutting member 2020 has been properly positioned relative to and advanced within the distal portion 2011B of the outer member 2010, the proximal portion 2011A of the outer member can be threaded onto or otherwise coupled to the distal portion 2011B. This action can ensure that the cutting member or portion 2020 is properly and securely positioned relative to the outer member 2010. In addition, such a design advantageously permits the cutting member 2020 to be easily removed and reinserted relative to the outer member 2010 for cleaning, sterilization, replacement, etc.

As discussed herein, once the cutting member or portion 2020 has been secured relative to the outer member 2010 and the proximal end 2019 of the outer member 2010 has been positioned within a targeted cylindrical opening of the subject's bone or other targeted site, the practitioner can begin advancing the inner member 2030 within and relative to the outer member 2010. Eventually, once the inner member 2030 has been moved sufficiently far relative to the outer member 2010, the distal shaft 2036 of the inner member 2030 will move within the cutting member 2020. This causes the cutters 2024 of the cutting member 2020 to be urged outwardly. Given the sloped or curved nature of the interior surfaces of the cutters 2024, the cutters 2024 are expanded so as to create a wedge or reverse tapered shape. Accordingly, once the cutters 2024 have been expanded, the practitioner can rotate the entire tool 2000 (e.g., via manipulation of the proximal handle 2012 of the outer member 2010) to more the expanded cutters 2024 relative to adjacent bone and/or other tissue of the subject, thereby causing bone and/or other tissue to be excised and/or otherwise removed. As discussed herein, this can advantageously transform the targeted cylindrical opening or cavity into one that has the desired wedge or reverse tapered shape.

As discussed herein in reference to other embodiments, the wedge-creation tools 1000, 2000 can be configured to be used manually, without the assistance of any motorized or other power-assisted devices (e.g., electromechanical devices, pneumatic devices, etc.). This can help ensure that the wedge shape is created in a safe and predictable manner. Also, such embodiments can help avoid any inadvertent damage (e.g., irreversible damage) to a targeted bone or other portion of the anatomy being treated. For example, the use of motorized drills or other power-assisted (e.g., non-manual) tools to create such wedge-shaped openings can lead to extensive damage to the targeted bone, and thus, to the inability to properly treat such an area with an implant.

As discussed herein, when the inner member 2030 is advanced within the interior of the cutting portion or member 2020, the cutters 2024 of the cutting portion or member can be radially expanded. In some embodiments, the cutters 2024 are radially expanded such that their outer diameter or other cross-sectional dimension after full expansion is 30% to 70% (e.g., 30-35, 35-40, 40-45, 45-50, 50-55, 55-60, 60-65, 65-70%, percentages between the foregoing, etc.) greater than their outer diameter or other cross-sectional dimension when retracted. Due to the sloped inner surfaces of the cutters 2024, once fully radially expanded, the cutters 2024 will be angled relative to the longitudinal axis of the tool and relative to the walls of the cylindrical opening. In some embodiments, the angle of the expanded cutters 2024 relative to the longitudinal axis of the cutting portion or member 2020 (and thus, the entire tool 2000) is between 0 and 45 degrees (e.g., 0-1, 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, 20-21, 21-22, 22-23, 23-24, 24-25, 25-26, 26-27, 27-28, 28-29, 29-30, 30-31, 31-32, 32-33, 33-34, 34-35, 35-36, 36-37, 37-38, 38-39, 39-40, 40-41, 41-42, 42-43, 43-44, 44-45 degrees, angles between the foregoing, etc.). In other embodiments, such an angle is greater than 45 degrees (e.g., 45-50, 50-55, 55-60 degrees, angles between the foregoing ranges, more than 60 degrees, etc.), as desired or required.

As discussed, in some embodiments, with the cutters 2024 radially expanded, the user can rotate the tool 2000 (e.g., using the handle 2012 of the outer member 2010). Accordingly, the entire tool 2000, including the outer member 2010, the inner member 2030 and the cutting member 2020, can begin to rotate in unison. As the tool 2000 is rotated, the radially expanded cutters 2024 will begin to cut and remove the adjacent tissue (e.g., bone). With sufficient rotation of the tool 2000, a reverse-tapered or wedge shaped opening can be created. In some embodiments, between 1 and 5 revolutions or rotations are required to create the opening. However, in other embodiments, depending on the specific protocol or procedure, the tool 2000 can be rotated less than 1 full revolution or more than 5 full revolutions. In some embodiments, rotation of the tool (e.g., rotation of the outer member 2010) can be commenced prior to full radial expansion of the cutters 2024. In other words, the surgeon or other practitioner can begin to rotate the tool 2000 after partial radial expansion of the cutters 2024 (e.g., when the inner member 2030 has been only partially advanced within the cutting portion or member 2020 of the tool). In some embodiments, the practitioner rotates the tool 2000 at different increments of radial expansion of the cutters 2024. This can advantageously facilitate the cutting or excision of bone tissue as the volume or area of bone tissue that the cutters will need to remove will be reduced at each incremental cutting phase (e.g., when compared to attempting to cut through a larger area of tissue at once by fully extending the cutters 2024 in a single expansion step). In some embodiments, a practitioner can use 2, 3, 4, 5 or more than 5 increments (e.g., of varying radial expansion of the cutters 2024) during a single wedge-creation procedure.

With continued reference to FIGS. 11A-11G, the distal end 2019 of the outer member 2010 of the tool 2000 can have a tapered, cylindrical shape. The size and shape of the distal end 2019 can be selected to match (e.g., in diameter, depth, etc.) the cylindrical opening into which the distal end 2019 will be inserted. As shown, a step or similar feature having a abutment surface can be included proximally to the distal end along the exterior of the outer member 2010 to ensure that the tool 2000 cannot be advanced deeper into the targeted bone or other tissue being treated.

As shown, the distal end 2019 of the outer member 2010 can include openings through which the cutters 2024 of the cutting member or portion 2020 pass once radially expanded. However, the distal end 2019 of the outer member 2010 can also include additional recesses, openings or slots 2015 that are separate and aside from the openings configured to accommodate the expanded cutters. Such additional slots 2015 can facilitate the accommodation and/or removal of excised bone and/or other tissue during the course of a procedure.

In some embodiments, the inner member 2030 is cannulated or otherwise includes one or more openings (e.g., along its longitudinal or axial centerline). As shown in the longitudinal, cross-sectional view of FIG. 11E, a central opening 2036 of the inner member 2030 can extend along the entire length of the inner member 2030, including the proximal handle 2035. Such an opening 2036 can permit the tool 2000 to be placed over a guide pin or other guiding tool to help assist with the accurate positioning of the tool, and thus the creation of a reverse-tapered or wedge opening, during use.

In some embodiments, such an opening 2036 can also be helpful in removing excised bone tissue that has been cut during a procedure. For example, in some embodiments, a rod or other device can be inserted within the opening 2036 to push bone material distally (e.g., out the distal end of the outer member and the entire tool). In other embodiments, a vacuum or suction force can be applied to the opening 2036 to selectively pull out excised bone and/or other tissue. Such procedure can be performed during, before or after a cutting procedure, as desired or required. In some embodiments, one or more liquids and/or other fluids (e.g., water, saline, medicaments, etc.) can be continuously or intermittently provided through the opening 2036 during use so as to reach the bone site being treated. Such fluids can assist in executing a particular protocol (e.g., to provide a desired degree of moisture or lubrication to facilitate the cutting process and/or the movement of the device during use, etc.).

As discussed above, any of the tool embodiments disclosed herein can be made to be disposable (e.g., single-use) items or reusable items. In some embodiments, one or more of the components of the tool can be reusable (e.g., the inner and outer members), whereas one or more of the components of the tool can be disposable (e.g., the cutting member or portion), as desired or required. A reusable tool (or the reusable components of a hybrid tool) can comprise one or more metals or alloys (e.g., stainless steel), thermoplastics and/or the like. In some embodiments, such reusable components are configured to be sterilized between uses or subjects being treated. In some embodiments, the sterilization of reusable tools or components thereof includes exposure to one or more chemical solutions or materials, autoclaving (e.g., with the requisite time exposure and requisite temperature) and/or any other sterilization or cleaning technique.

Figure 14A:
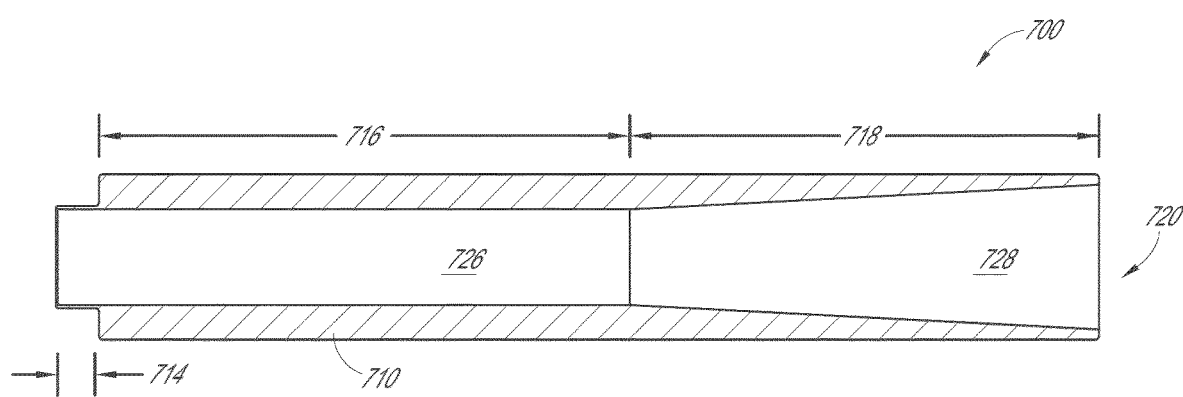
FIG. 14A illustrates a longitudinal cross-sectional view of another embodiment of an implant introducer.

Once a reverse taper implant site has been created in the targeted joint or other portion of the patient (and, where applicable, the guide pin or other member has been removed), a clinician can deliver the implant to the implant site using an introducer 600. As illustrated in FIGS. 12A-13B, an introducer 600 can include a generally cylindrical introducer tube 610 having an opening 620 through which the implant may be passed. In some embodiments, the distal end 606 of the introducer tube 610 can comprise a neck or other narrowed portion 608. As shown in FIG. 13B, the neck portion 608 can include a wall 612 having a rounded distal edge 613. In some embodiments, the neck portion 608 has a length (labeled 614 in FIG. 12C) of about 0.155 inches to about 0.170 inches. Further, as best illustrated in the longitudinal cross-sectional view of FIG. 12C, the internal diameter of the introducer tube 610 can vary along its length. For example, in the depicted embodiment, a proximal portion 618 of the introducer 600 comprises a flared shape, wherein the inside diameter of the opening 620 is progressively reduced in the proximal to distal direction. Further, as shown, the opening 620 can maintain a generally constant inner diameter along a second, more distal portion 616 of the introducer tube 610. In other embodiments, the inner diameter, length, other dimension and/or other details or properties of the introducer 600, including its flared interior portion 628, its generally cylindrical interior portion 626 of the introducer tube 610, its neck portion 608 and/or the like can be different than shown in FIGS. 12A-12C and 13A-13B and described herein. By way of example, the embodiment illustrated in FIG. 14A comprises a longer flared interior portion 728 (e.g., relative to the adjacent generally cylindrical portion 726) than the introducer 600 of FIG. 12C.

Figure 14B:
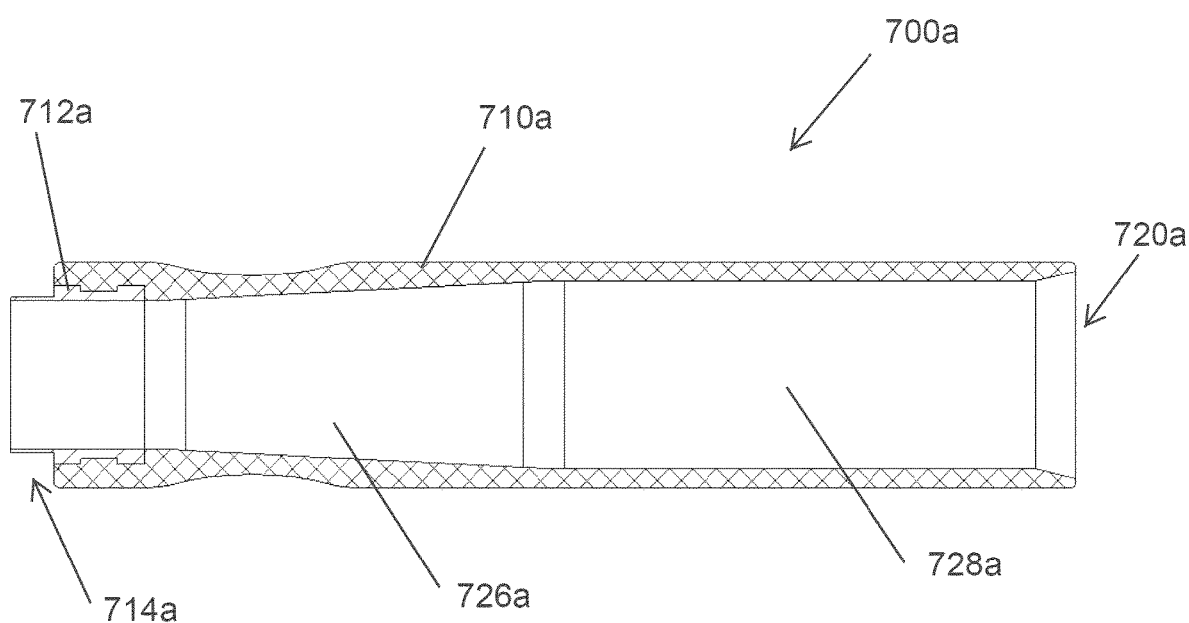
FIG. 14B illustrates a cross-sectional view of an introducer comprising a two-part construction according to one embodiment.

Another embodiment of an introducer 700a is illustrated in FIG. 14B. As shown, the introducer 700a can include the tapered interior surface along the distal end 726a (e.g., as opposed to the proximal end, as depicted in other arrangements herein). This can facilitate the insertion within and/or passage through the interior of the introducer 700a since the implant advanced therethrough will not be radially compressed until the distal portion 726a of the introducer. Thus, in some embodiments, the proximal portion 728a of the interior of the introducer 700a can be cylindrical (e.g., non-tapered), which the distal portion 726a of the interior of the introducer can be tapered (e.g., sloped, flared, etc.). Such a design can be incorporated into any of the embodiments of an introducer disclosed herein or equivalents thereof.

In some embodiments, as illustrated in FIG. 14B, the introducer can comprise a two-part or multi-part construction, as desired or required. For example, in some embodiments, the distal end of the introducer 700a includes an insert 712a comprising a metal and/or alloy (e.g., stainless steel), whereas the proximal portion 710a of the introducer comprises a different material, such as, for example, a polymeric material (e.g., polycarbonate). Such a configuration can help create a lower cost introducer 700a, and thus, implant insertion system or kit. Further, the stronger (e.g., more rigid) distal insert 712a can help maintain its shape to facilitate resisting the higher compressive forces (e.g., generated by the compressed implant passing therethrough) and/or to permit for a thinner wall distal end 714a of the introducer. In some embodiments, the introducer 700a and/or any other component or the implant delivery system can be disposable and/or reusable, as desired or required.

Figure 15A:
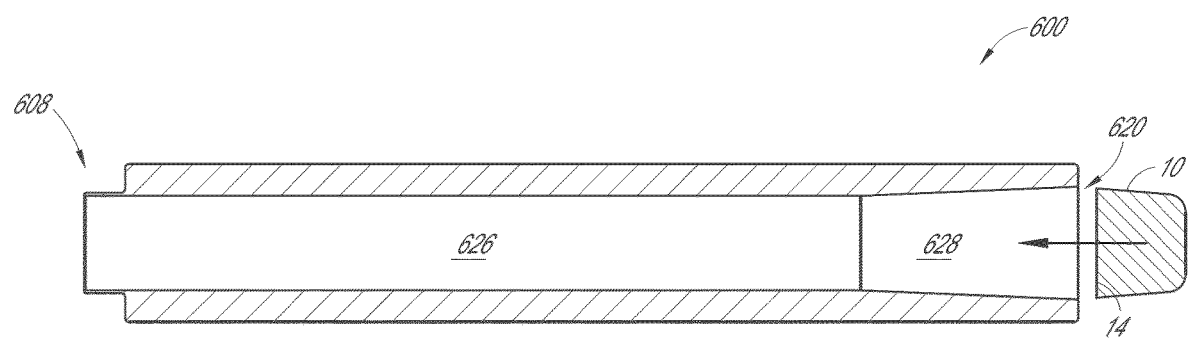
FIGS. 15A-15C illustrate time-sequential side views of an implant being inserted within an implant site using the introducer of FIG. 12A.
Figure 15B:
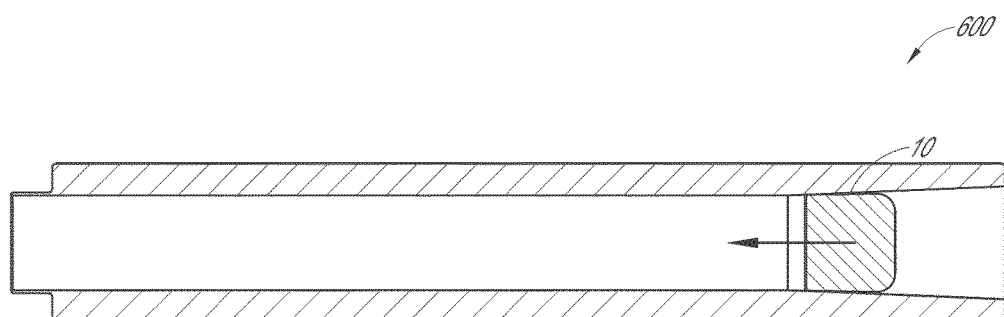
Figure 15C:
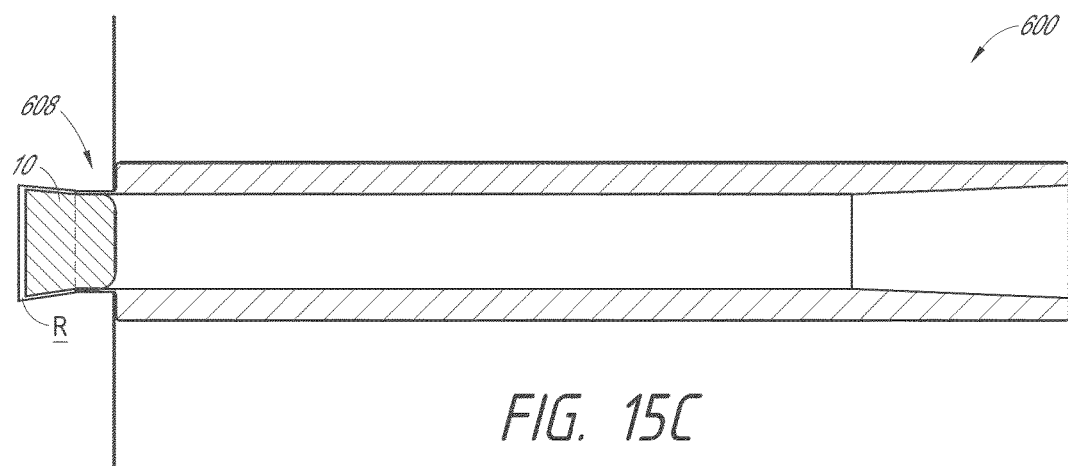

The neck portion 608 of the introducer tube 610 can be positioned at least partially within the opening or recess into which the implant will be secured. In some embodiments, the introducer can be sized, shaped and otherwise configured to that the neck portion 608 fits generally snugly within the implant site. With reference to FIGS. 15A-15C, an implant 10 can be placed within the opening 628 along the proximal end 602 of the introducer 600. As shown, in some embodiments, the implant 10 is advanced into the interior of the introducer 600 with its base or bottom 14 end first.

As the implant 10 is urged deeper (e.g., more distally) into the interior of the introducer 600, the implant 10 may become radially compressed by the adjacent interior walls. If sufficient force is applied to the implant 10, the implant 10 passes through the neck portion 608 of the introducer and into the implant site R. As illustrated in FIG. 15C, in such an arrangement, the implant's base end 14 will be located along the bottom of the implant site. According to some embodiments, a plunger or other pusher member (not shown) can be inserted within the interior of the introducer to help push the implant through the introducer and into the implant site. Such a plunger or pusher member can be operated manually and/or with the assistance of an external power-assist device (e.g., mechanically, pneumatically, hydraulically, etc.), as desired or required.

Figure 16A:
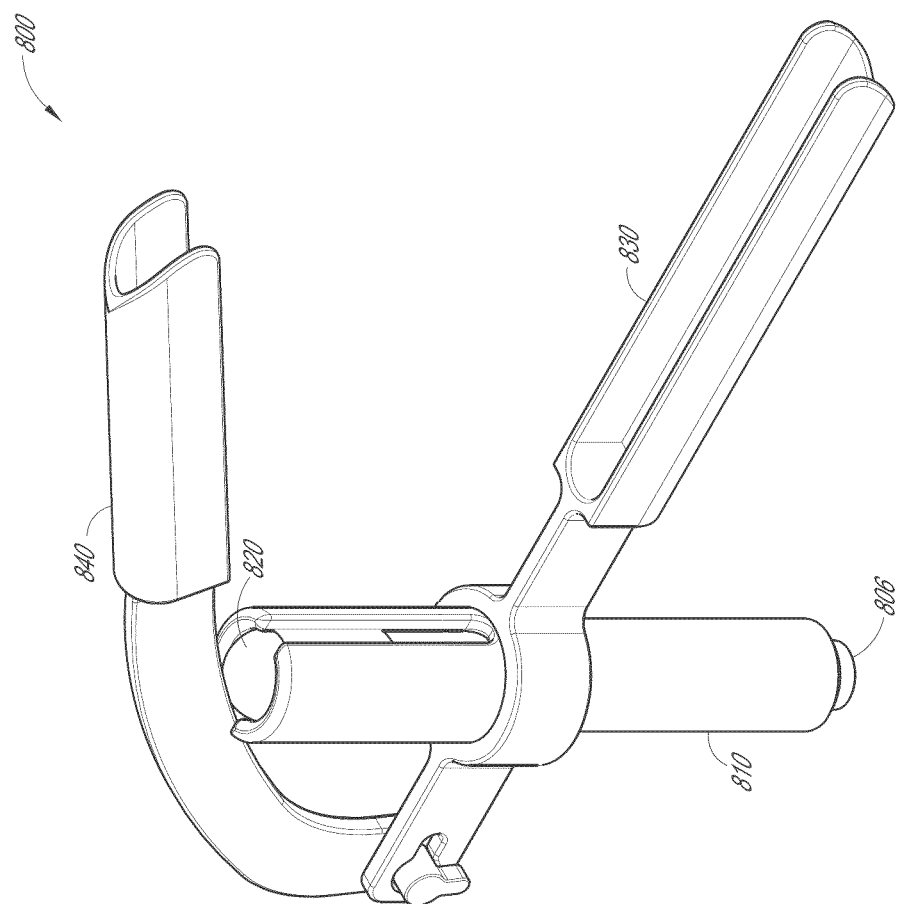
FIG. 16A illustrates a perspective view of an assembled implant delivery tool according to one embodiment.
Figure 16B:
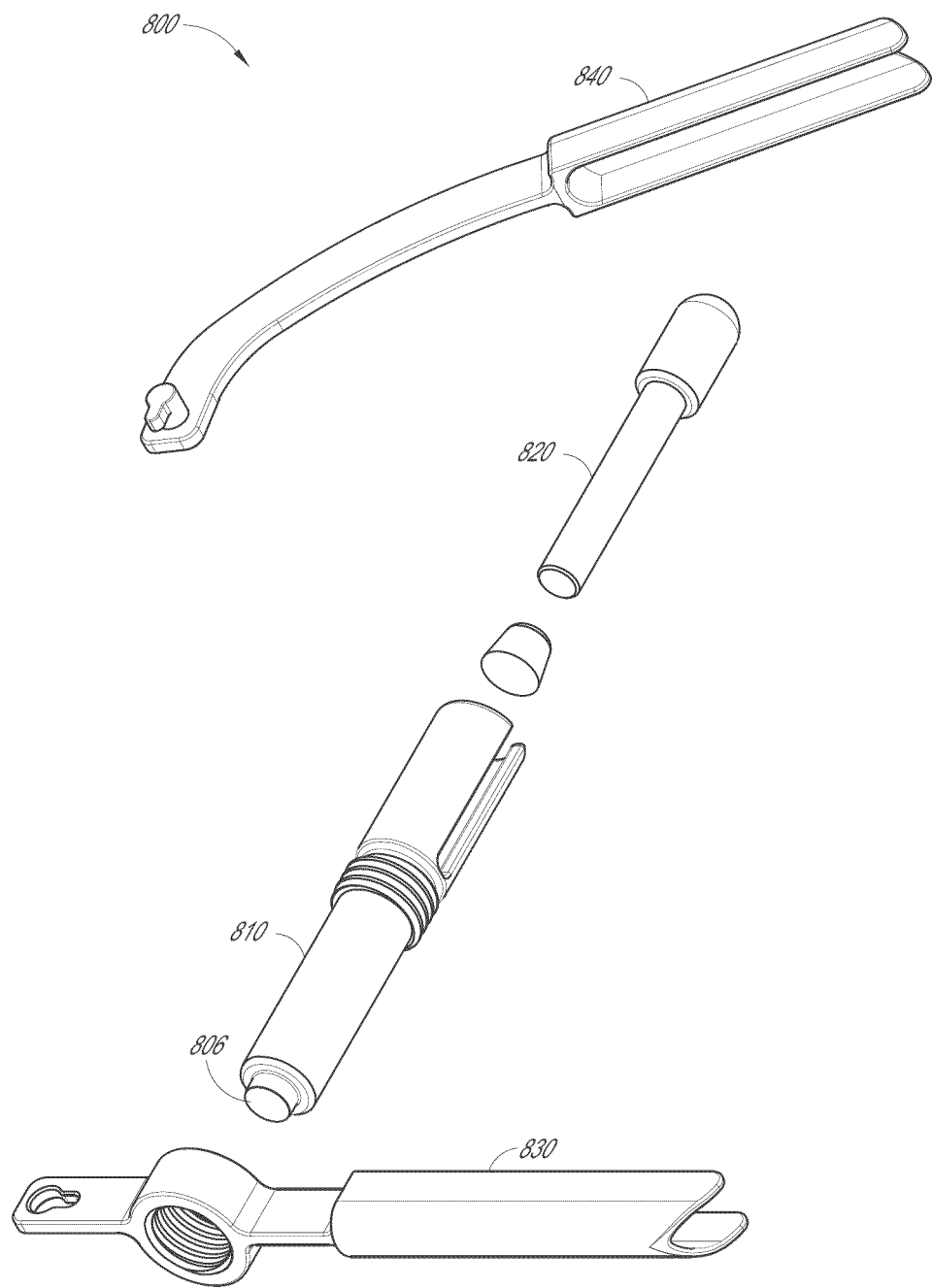
FIG. 16B illustrates an exploded view of the delivery tool of FIG. 16A.
Figure 16D:
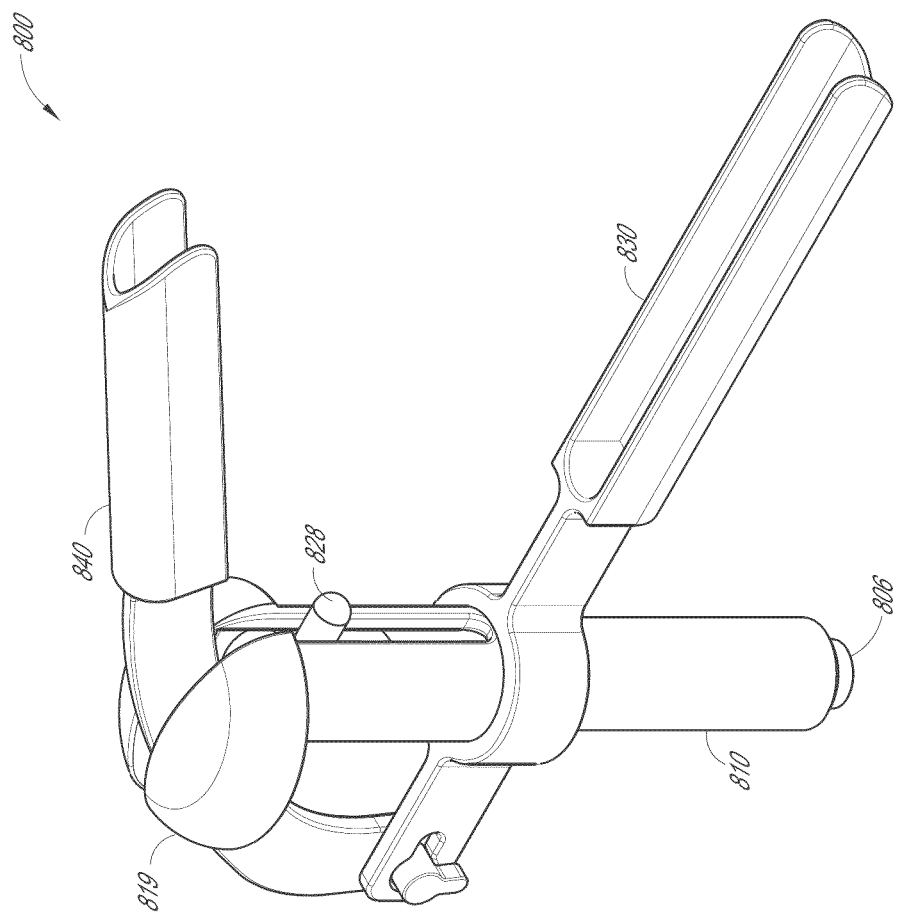
FIG. 16D illustrates a perspective view of an assembled implant delivery tool according to one embodiment.
Figure 16E:
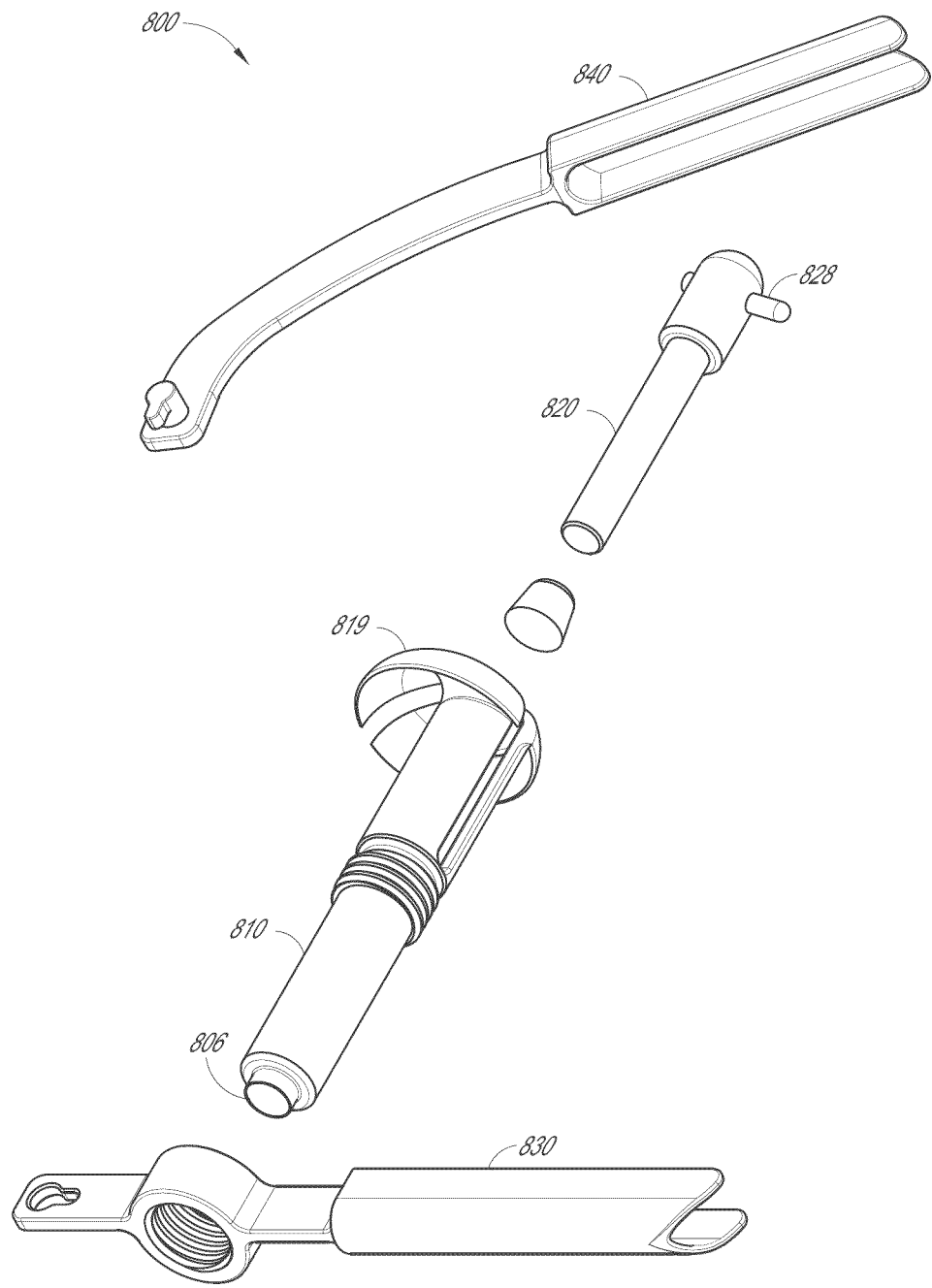
FIG. 16E illustrates an exploded view of the delivery tool of FIG. 16D.

According to some embodiments, once a reverse taper site has been created in the targeted joint or other portion of the patient (and, where applicable, the guide pin or other member has been removed), a clinician can deliver the implant to the implant site using a mechanically-assisted delivery tool or introducer 800. One embodiment of such a tool is illustrated in FIGS. 16A-16C. Another embodiment of such a tool is illustrated in FIGS. 16D-16E. As shown, the delivery tool or introducer 800 can comprise, among other things, an introducer tube 810, a plunger 820, a handle 830 and a clamp 840.

Such mechanically-assisted delivery devices can be helpful in advancing the implant through the interior of an introducer tube against a relatively large resistance of backpressure. Such a resistive force can be particularly high when the implant comprises a relatively large taper angle θ. Accordingly, in some embodiments, the use of such delivery tools makes the delivery of reverse taper implants into corresponding implant sites possible, while allowing the clinician to safely and accurately guide the implant into a targeted anatomical implant site. In several embodiments, the delivery tool is capable of overcoming resistive forces of about 5 to about 20 pounds. In some embodiments, the delivery tool exerts a force about 5 to about 25. In some embodiments, the delivery device is operated by or with the assistance of one or more motors. For example, in some embodiments, the clamp is moved (e.g., rotated) relative to the handle using (or with the assistance of) one or more stepper motors and/or any other type of motor or actuator. In some embodiments, delivery of an implant through the introducer tube 810 is accomplished with at least some assistance from air or pneumatic pressure. For example, air or other fluid can be injected into the interior of the introducer tube once the implant is inserted therein. The delivery of air can be incorporated into a plunger member 820 (e.g., via one or more interior lumens) so that the implant can be advanced through the introducer tube 810 into the implant site using mechanical force (e.g., by moving the plunger 820 through the tube 810) and/or by injecting air and/or other fluids into the interior of the tube 810. The fluid openings through the plunger 820 and/or any other fluid passages can be placed in fluid communication with a compressor or other fluid generating device. Advancement of the implant through the introducer tube 810 can be accomplished by applying a vacuum along or near the distal end of the tube 810 (e.g., through one or more vacuum ports along the introducer tube 810). Such vacuum ports or openings can be placed in fluid communication with a vacuum or other suction generating device.

According to some embodiments, the delivery tool comprises one or more depth stop features or components to ensure that the implant being delivered to a target implant site is properly delivered into the target implant site. In some embodiments, the depth stop features help protect the structural integrity of the implant as the implant is being inserted within the target anatomical implant site.

In some embodiments, the delivery device comprises and/or is operatively coupled to one or more pressure gauges or other pressure or force measuring devices, members or features. Such gauges or other measurement devices can help ensure that a maximum backpressure or force is not exceeded when operating the device. This can help protect the integrity of the implant (e.g., to ensure that the structural integrity, water composition and/or other properties of the implant are maintained), protect the delivery device, protect the user and/or the patient and/or provide one or more other advantages or benefits.

According to some embodiments, the introducer tube 810 of the delivery tool or device 800 comprises one or more viewing windows that permit the implant to be viewed as it is being advanced through the device 800 to the implant site. In some embodiments, the introducer tube 800 (and thus the longitudinal axis along which the implant is advanced through the delivery tool or device) is substantially perpendicular with the surface of the bone or other anatomical site into which the implant will be delivered and/or the handle 830 of the device 800.

According to some embodiments, at least a portion of the interior of the introducer tube 810 comprises and/or is otherwise coated or lined with one or more absorbable or lubricious layers, materials and/or other substances. Such materials can help preserve the moisture level of the implant as it is being advanced through the introducer tube 810. The interior surface of the introducer tube can comprise a low coefficient of friction to facilitate the delivery of an implant through the delivery device or tool 800. In some embodiments, the effective coefficient of friction along the interior of the introducer tube can be lowered polishing such surfaces. As noted herein, the introducer, including its interior surfaces, can comprise surgical grade stainless steel.

According to some embodiments, the delivery tool or device 800 is incorporated into the tool configured to create a reverse tapered implant site. For example, such a combination device can be coupled to a drill or other mechanical device to first create the implant site. Then, the combination device can take advantage of the mechanical output generated by the drill and/or other mechanical or motorized device to help urge the implant through the introducer tube of the combination device.

Figure 17A:
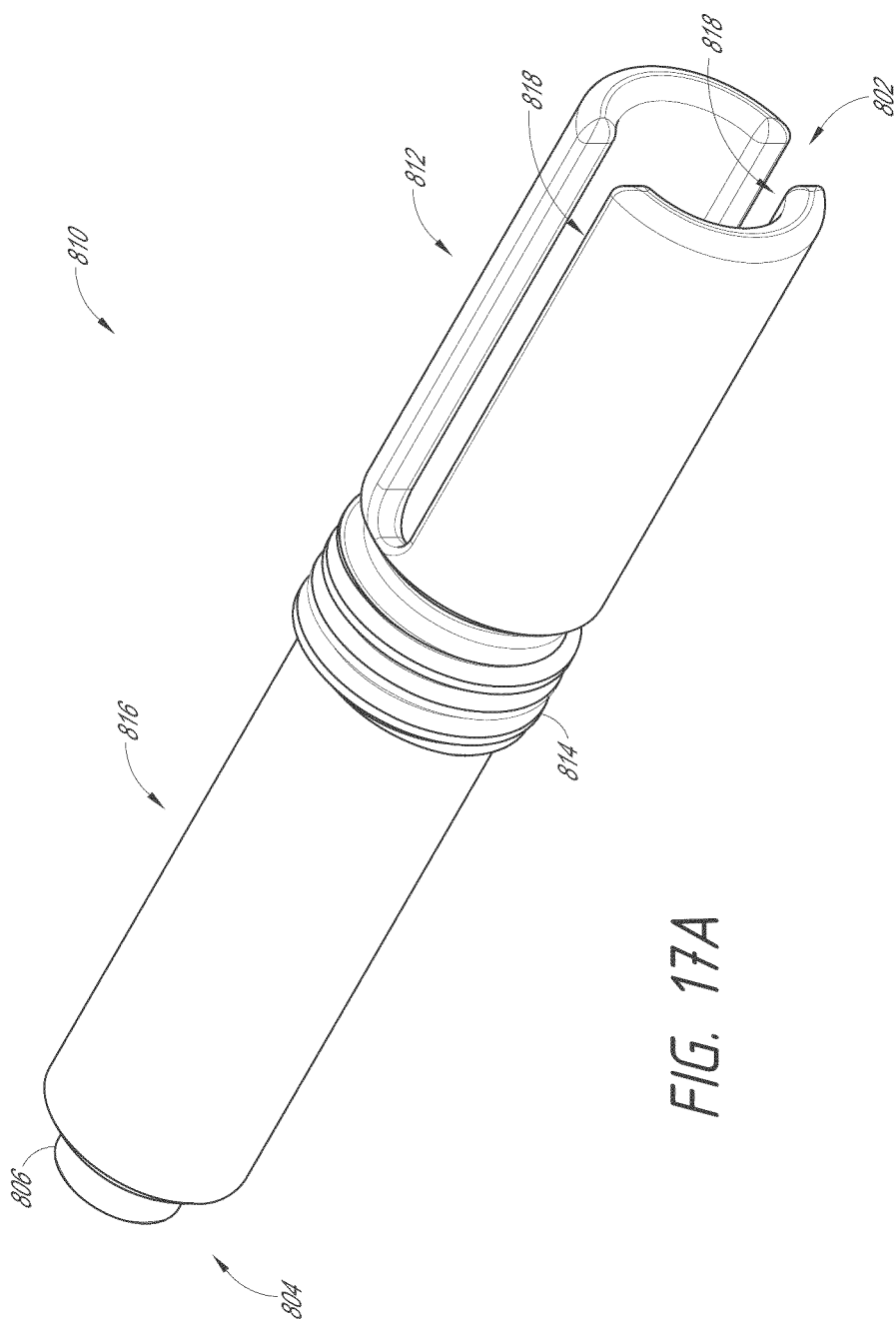
FIG. 17A illustrates a perspective view of an introducer.
Figure 17B:
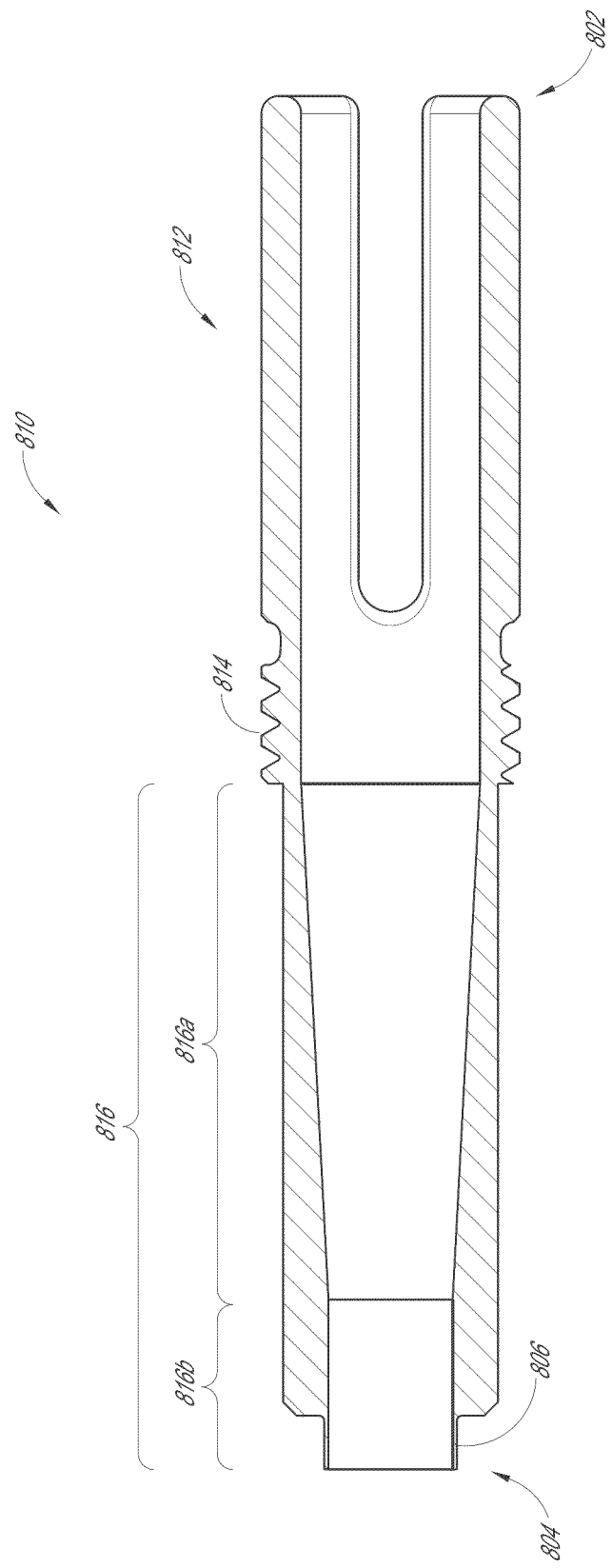
FIG. 17B illustrates a cross-sectional view of the introducer of FIG. 17A.

As illustrated in FIGS. 17A and 17B, the introducer tube 810 of the mechanically-assisted delivery tool 800 can be hollow and generally cylindrical in shape. However, in other embodiments, the shape, general structure and/or other characteristics of the tube 810 can be different than disclosed herein. In some embodiments, the introducer tube 810 comprises an externally threaded portion 814, a proximal portion 812 extending between a proximal end 802 and the externally threaded portion 814, and a distal portion 816 extending between the externally threaded portion 814 and a distal end 804. The distal end 804 of the introducer 810 can comprise a neck or other narrowed portion 806.

As best illustrated in the longitudinal cross-sectional view of FIG. 17B, the internal diameter of the introducer tube 810 can vary along at least a portion of the tube's length. For example, in the depicted embodiment, the proximal portion 812 of the introducer or introducer tube 810 has a generally constant, consistent or flat inner diameter. In addition, as shown, the distal portion 816 of the introducer tube 810 can comprise a generally tapered or sloped portion 816a, such that the inside diameter of the tube is progressively reduced in the proximal to distal direction. In some embodiments, the slope along the interior surface of the tube 810 can be generally linear. However, in other arrangements, the slope of the interior surface of the tube 810 is at least partially non-linear (e.g., curved, rounded, irregular, etc.), either in addition to or in lieu of any generally linear and/or constant portions, as desired or required for a particular application or use. Further, in some embodiments, as illustrated in the cross-sectional view of FIG. 17B, a portion 816b proximate the distal end 804 comprises a generally constant or flat (e.g., non-sloped) inner surface or diameter. Further, in other embodiments, the inner diameter or surface, length, other dimensions and/or other details or properties of the introducer tube 810, including any internal tapered or sloped portions 816a, any generally cylindrical (e.g., constant, flat, non-sloped, etc.) interior portions 816b, any neck portions 806 and/or the like can be different than shown in FIGS. 17A-17B and described herein.

According to some embodiments, the proximal portion 812 of the introducer tube 810 includes one or more slits or other openings 818. As shown, such a slit 818 can begin adjacent to or near the externally threaded portion 814 of the tube 810 and can extend to or near the proximal end 802 of the tube 810. In some embodiments, the proximal portion 812 of the introducer tube includes two (or more) slits 818 located opposite each other in the introducer 810 to form a channel through the proximal portion 812. In some embodiments, for example as shown in FIGS. 16D-16E, the proximal portion 812 of the introducer tube 810 comprises a flange 819 or other protruding or flared portion extending outwardly (e.g., radially outwardly in a continuous or intermittent manner) from or near the proximal end 802. In other embodiments, the flange or other protruding member 819 can be located along one or more other longitudinal locations of the tube 810, as desired or required. The flange 819 can be substantially or generally flat and/or can include any other shape (e.g., curved, fluted, etc.). The flange 819 can be integrally formed or attached to the proximal portion 812 of the tube 810. Alternatively, the flange 819 can be a separate member that can be selectively attached to or removed from the tube 810 and/or any other portion of the tool 800.

Figure 18:
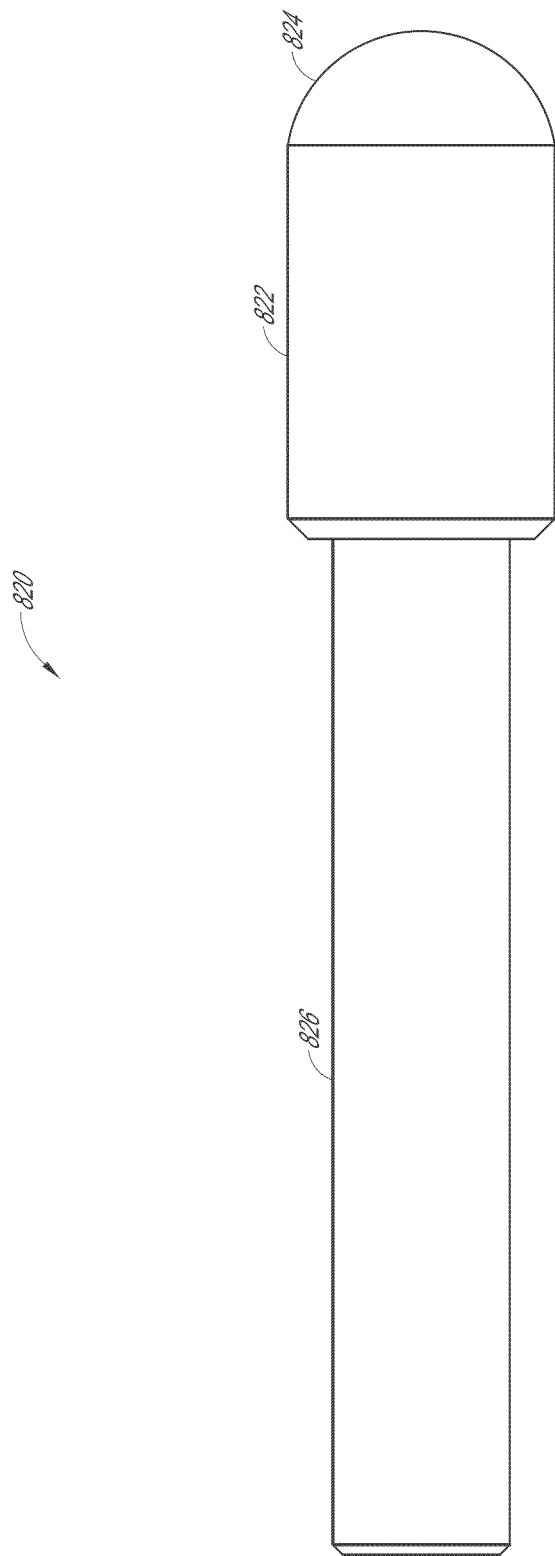
FIG. 18 illustrates a side view of a plunger.

With reference to FIG. 18, the plunger 820 of the tool 800 can be generally cylindrical in shape with an enlarged proximal head portion 822 that includes a domed proximal end 824. In some embodiments, in a properly assembled mechanically-assisted delivery tool 800, the plunger 820 is shaped, sized and otherwise configured to slide within the hollow interior passage of the introducer tube 810. Thus, as discussed in greater detail herein, by actuating the tool, a clinician or other user can selectively move the plunger within an interior portion of the introducer tube 810 in order to urge an implant (e.g., a tapered implant) through the distal end of the tube and into a targeted implant site of a patient.

With continued reference to FIG. 18, the main body 826 of the plunger 820 can have a diameter approximately the same as and/or slightly smaller than the inner diameter of the neck portion 806 and distal portion 816b of the introducer 810. In some embodiments, as illustrated in the embodiment of FIG. 16E, the head portion 822 of the plunger 820 includes a motion limiter or depth stop 828. The motion limiter 828 can comprise one or more knobs, protrusion members and/or other members or features that generally extend outwardly from the head portion 822 of the plunger. In some embodiments, such a motion limiter, depth stop member or feature and/or other protruding member 828 is configured to slide within the slit(s) 818 or other openings of the introducer tube 810. These features can help prevent or otherwise limit distal movement of the plunger 820 relative to the introducer tube (e.g., when the motion limiter or depth stop 828 contacts or abuts the base of the slit(s) 818). Further, such a feature can help prevent or limit rotation of the plunger relative to the tube 810 during use. In some embodiments, the head portion 822 of the plunger 820 comprises a diameter approximately the same as and/or slightly smaller than the inner diameter of the proximal portion 812 of the introducer tube 810. Accordingly, movement of the plunger 820 relative to the tube 810, beyond a particular point, will generally be prevented or limited when the head portion 822 contacts or abuts the narrowing inner diameter of the tapered portion 816a of the distal portion 816 of the introducer tube. Therefore, the corresponding abutting features of the plunger 820 and the introducer tube 810 can advantageously help limit the depth to which an implant (e.g., tapered implant) can be delivered relative to an implant site of a patient. In some embodiments, this can help improve the safety and efficacy of the implant, the related tools and the implant procedure.

Figure 19A:
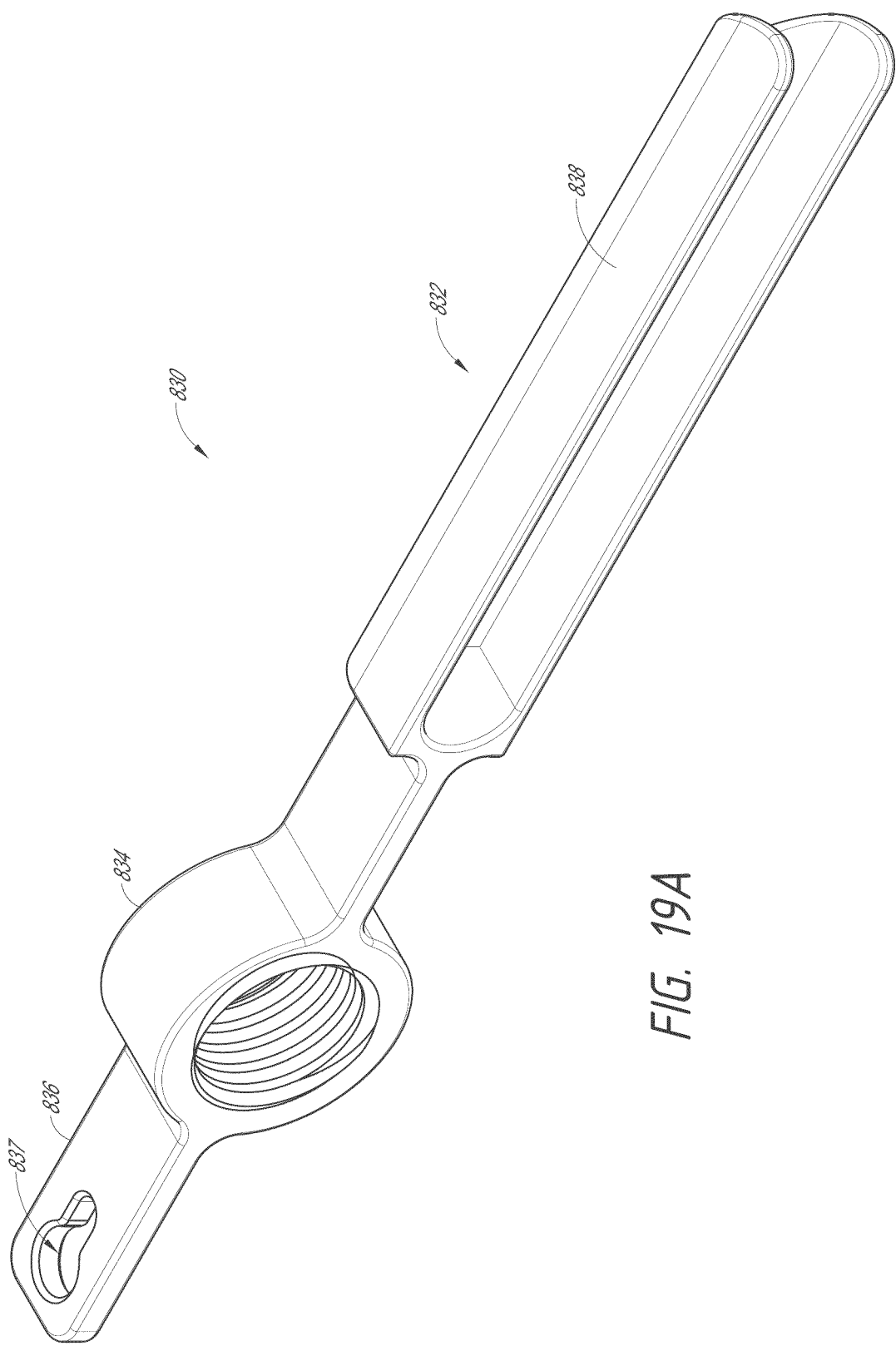
FIG. 19A illustrates a perspective view of a handle.

According to some embodiments, as illustrated in FIG. 19A, the handle 830 of the delivery tool 800 comprises a generally circular internally threaded nut portion or introducer tube receiving portion 834. As shown, the threaded nut portion or introducer tube receiving portion 834 can be interposed between an elongate proximal section 832 and an elongate distal section 836. In the depicted arrangement, the introducer tube receiving portion 834 is located closer to the distal section 836 of the handle 830. However, in other embodiments, the portion 834 can be located along any other portion of the handle 830, as desired or required. Further, the introducer tube receiving portion 834 can include one or more other engagement or connection features or devices (e.g., snap connections, press-fit or friction-fit connections, screws or other fasteners, adhesives, etc.), either in lieu of or in addition to a threaded connection.

With continued reference to the perspective view of the handle illustrated in FIG. 19A, the proximal portion or section 832 of the handle can be longer than the distal portion or section 836. In other words, as noted above, the introducer tube receiving portion 834 can be positioned closer to the distal end than the proximal end of the handle 830. However, in other embodiments, the introducer tube receiving portion 834 is located at or near between the distal and proximal ends of the handle, or at, near or closer to the proximal end of the handle, as desired or required.

Figure 19B:
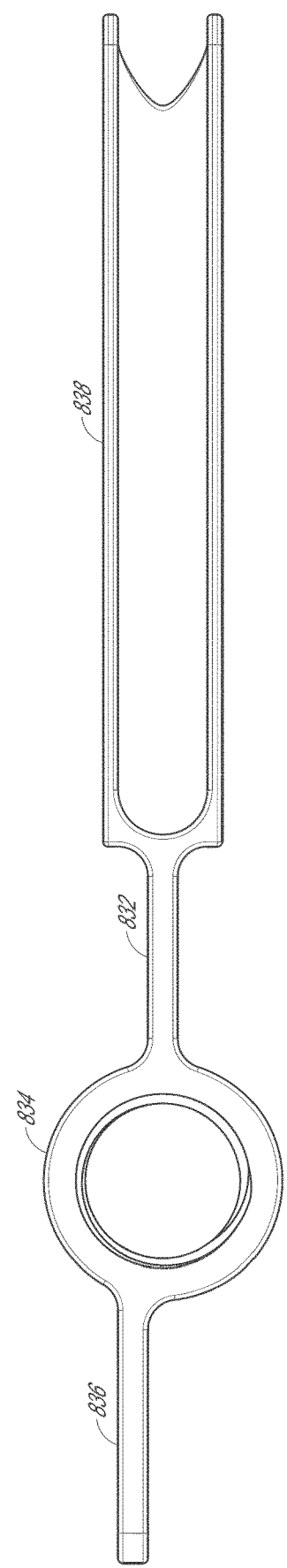
FIG. 19B illustrates a top view of the handle of FIG. 19A.

As shown in FIG. 19A, the proximal section 832 and distal section 836 can extend in generally opposite directions from the nut or introducer tube receiving portion 834. However, in some embodiments, a longitudinal axis of the distal section 836 is slightly offset from a longitudinal axis of the proximal section 832. Such a configuration can assist with the coupling of the clamp 840 as described herein. For example, in the illustrated embodiment (e.g., when viewed from the top as shown in FIG. 19B), a centerline or orientation of the distal section or portion 836 of the handle is generally offset with respect to the centerline or orientation of the proximal section 832. The introducer tube receiving portion 834 can be sized, shaped and otherwise configured so that the distal section 816 of the introducer tube 810 can pass through the opening of the introducer receiving portion 834. Further, the externally threaded portion 814 of the introducer tube 810 can operatively engage and mate with the internal threaded portion of the introducer tube receiving portion 834. As noted above, in other embodiments, the handle 830 can engage the introducer tube 810 using one or more other attachment methods, features or devices (e.g., fasteners, snap-fit or friction-fit connections, other mating connections or couplings, adhesives, etc.) either in addition to or in lieu of a threaded connection.

In some embodiments, the elongate proximal section or portion 832 of the handle comprises a grasping portion 838 configured to be selectively gripped and manipulated by a user during use. The grasping portion 838 can be contoured, shaped and/or otherwise configured to improve the user's grip on the handle 830. In the illustrated embodiment, the distal section or portion 836 of the handle comprises a generally rectangular cross-section. However, the distal portion and/or any other portion of the handle 830 can include any other shape (e.g., circular, oval, square, polygonal, etc.). When the nut portion of introducer receiving portion 834 is oriented horizontally, the distal section 836 of the handle comprises a generally vertical shape so that it is taller than it is deep.

According to some embodiments, the distal section 836 of the handle 830 comprises a keyhole 837 or other opening for coupling to the clamp 840 of the device. The keyhole 837 or other opening can be configured to allow the clamp 840 to be quickly and easily connected to and/or disconnected from the handle 830. In other arrangements, however, the clamp 840 can be permanently or substantially permanently attached to the handle 830. In other embodiments, the size, shape, orientation, and/or other details or properties of the handle 830 can be different than shown in FIGS. 19A-19B and described herein.

Figure 20A:
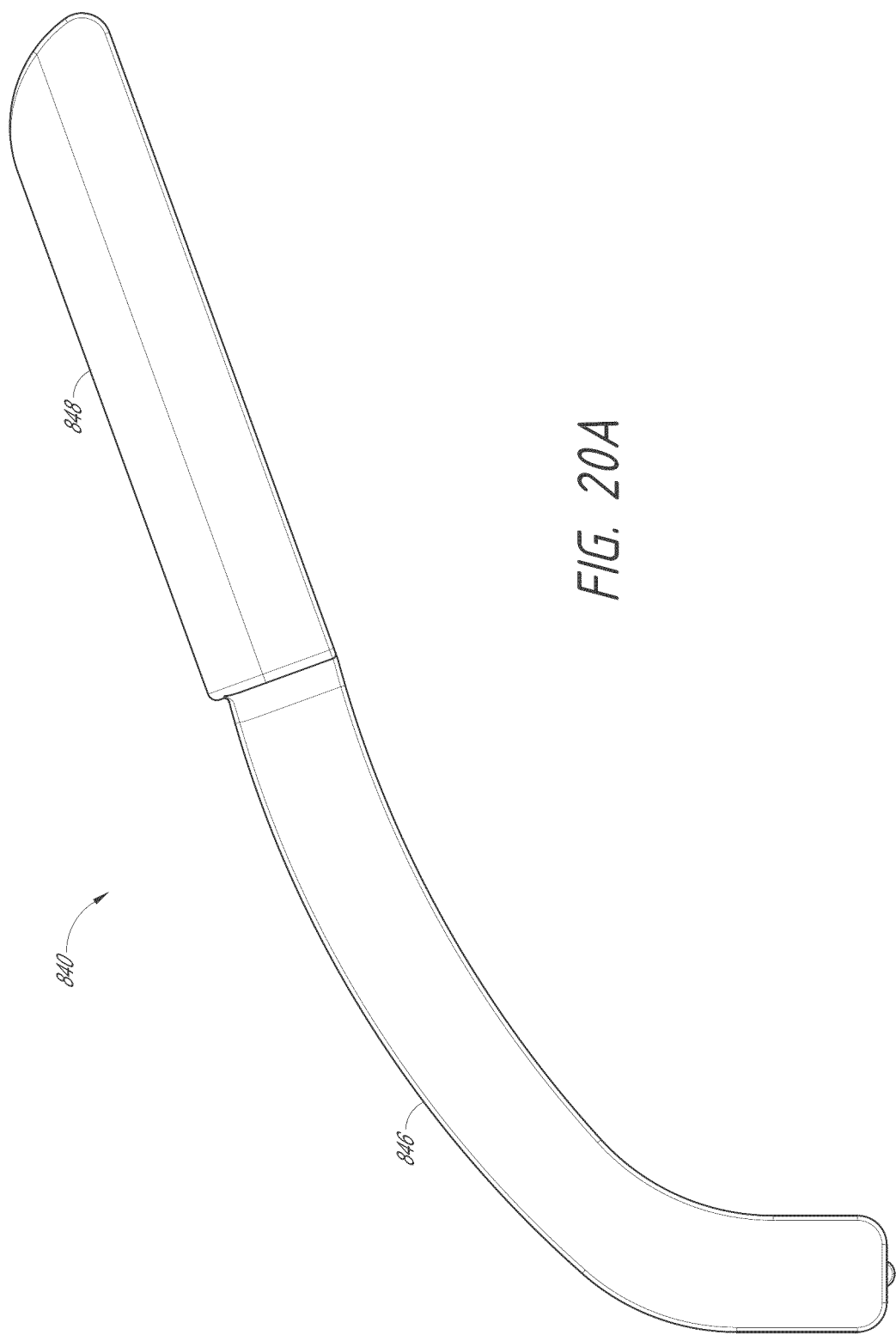
FIG. 20A illustrates a side view of a clamp.
Figure 20B:
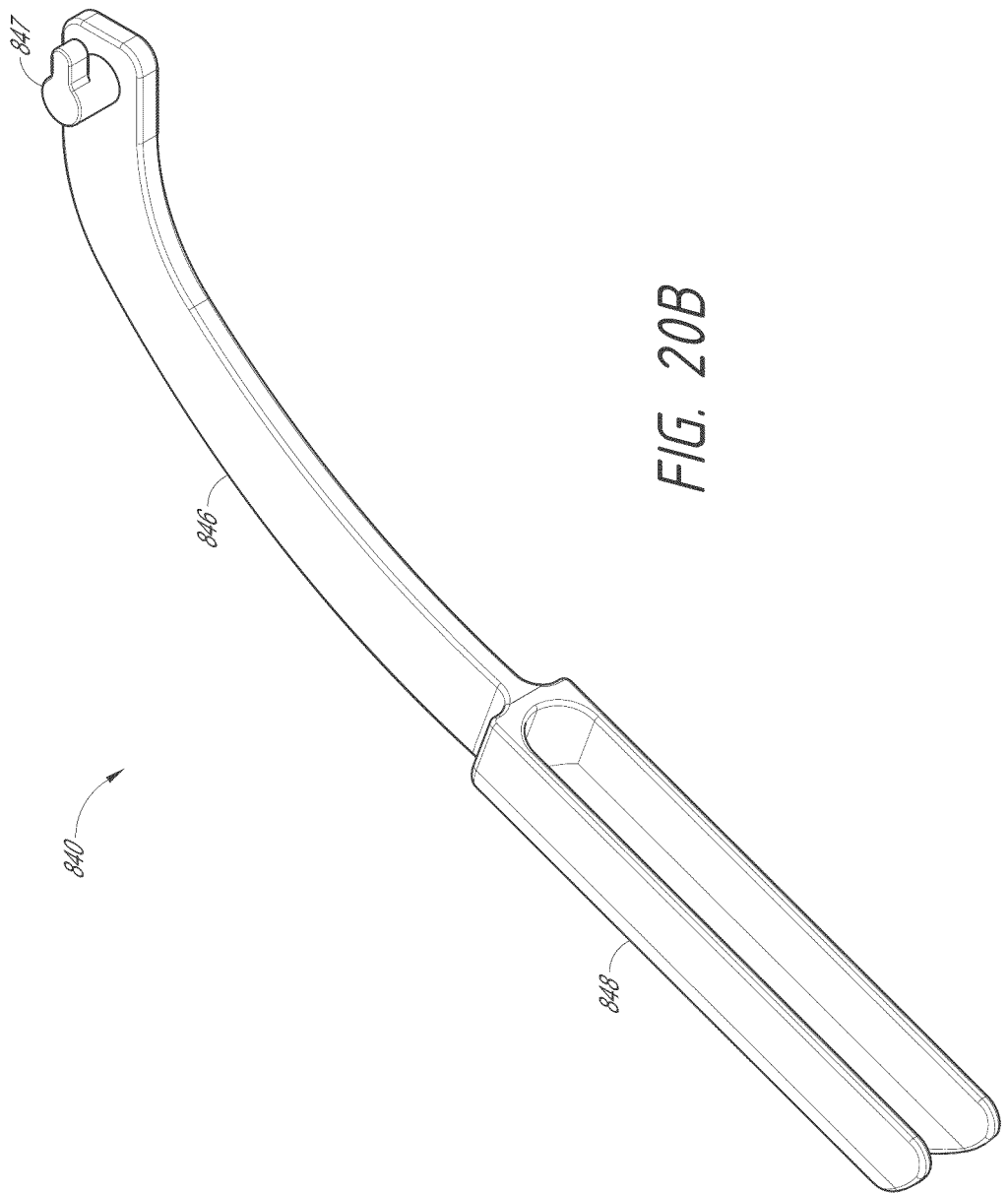
FIG. 20B illustrates another view of the clamp of FIG. 20A.

With reference to FIGS. 20A and 20B, the clamp 840 can comprise an elongate member having a slight curve. A proximal portion of the clamp 840 can include a handle or grasping portion 848 that a user can grip during use of the device. A distal portion 846 of the clamp 840 is generally sized, shaped and otherwise configured such that it can be moved within the slit 818 of the introducer tube 810. In some embodiments, as illustrated herein, the distal end of the clamp 840 comprises a key 847 for insertion within the keyhole or other opening 837 of the handle 830 in order to couple the clamp to the handle.

Therefore, the handle 830 and the clamp 840 can be connected to one another about a hinge or other rotatable point, thereby permitting the handle to be selectively rotated and/or otherwise moved relative to the clamp. As discussed in greater detail herein, such a relative rotation between the clamp and the handle can be used to provide the mechanical force necessary to move the plunger 820 within the introducer tube 810. This can advantageously urge an implant (e.g., tapered hydrogel implant) through the tube 810 and into a target recess of an implant site. Accordingly, the forces created by moving the clamp relative to the handle can help move an implant against relatively high back-forces (e.g., against relatively high friction and/or other resistive forces) within the introducer tube. Such movement of the implant can be particularly difficult for reverse tapered implants where at least a portion of such implants experiences generally high radially compressive forces while being moved through an interior lumen or other opening of the introducer tube 810.

According to some embodiments, to assemble the delivery device 800 in preparation for use, the user inserts the implant 10 (e.g., reverse tapered implant, other joint implant, etc.) into the introducer tube 810 via the proximal end 802. The plunger 820 can then be inserted into the proximal end 802 of the introducer tube 810 and used to distally advance the implant 10 within the introducer tube 810. Once the handle 830 is coupled to the introducer tube 810 (e.g., by threading the nut portion or introducer tube receiving portion 834 onto the externally threaded portion 814 of the introducer tube 810), the clamp 840 can be coupled to the handle 830 by inserting the key 847 (or other protruding portion or feature) of the clamp 840 into the keyhole 837 (or other opening) of the handle 830. When assembled, e.g., as illustrated in FIGS. 16A, 16C, 16D and 21A-21C, the clamp 840 is generally positioned and movable within the slit 818 of the introducer tube 810.

As discussed in greater detail herein, the clamp 840 can be rotatably attached to the handle 830 (e.g., at a hinge point), thereby allowing a user to selectively rotate or otherwise move the clamp relative to the handle (e.g., to move the clamp 840 toward or away from the handle 830 within the slit, groove or other opening of the introducer tube 810). In some embodiments, an offset between the distal section 836 and proximal section 832 of the handle 830 permits the distal portion 846 of the clamp 840 to be aligned with the slit 818 in the introducer tube so that the clamp can be selectively moved within the slit 818 when the clamp 840 and handle 830 are coupled to one another (e.g., via the key 847-keyhole 837 joint or a similar feature or mechanism). Therefore, in some embodiments, the delivery device 800 is configured for quick, easy and convenient assembly and disassembly for cleaning, sterilization, repair, maintenance and/or any other reason or purpose.

According to some embodiments, the various components of the mechanically-assisted delivery device 800 comprise one or more rigid and/or semi-rigid materials that are configured to withstand the forces, moments, chemicals and/or other substances, temperature fluctuations and/or other elements to which they may be exposed. For example, the components of the implant delivery device can comprise one or more metals (e.g., stainless steel, other surgical steel, other types of steel, etc.), alloys, plastics and/or the like. Such materials can permit the device to be autoclaved, sterilized or otherwise cleaned during a specific disinfection protocol. In addition, the structural and other physical characteristics of the device can permit the user to exert the necessary forces using the device to deliver implants of various sizes, shapes and/or configurations through the corresponding introducer tube and into a target implant site of a patient.

In use, the distal neck portion 806 of the introducer tube 810 can be positioned at least partially within the opening, recess or other implant site into which the implant 10 will be secured. In some embodiments, the introducer tube 810 is sized, shaped and otherwise configured to that the neck portion 806 fits generally snugly within the implant site. To deliver the implant 10 (e.g., reverse taper implant) through the device 800 and into the targeted implant site, the user can urge the clamp 840 toward the handle 830 of the device (e.g., so that the clamp rotates or otherwise moves relative to the handle). According to some embodiments, as the distal portion 846 of the clamp 840 moves downwardly through the slit, slot or other opening 818 of the introducer tube 810, a portion of the clamp 840 (e.g., the distal portion 846) contacts the plunger 820 (e.g., the domed proximal end 824), and urges the plunger 820 distally within the introducer tube 810.

Figure 21C:
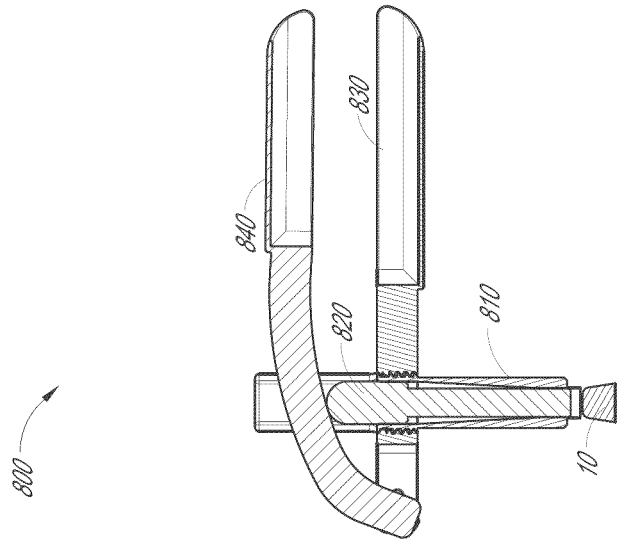
FIGS. 21A-21C illustrate sequential views of an implant being moved through and deployed from a delivery tool.
Figure 21B:
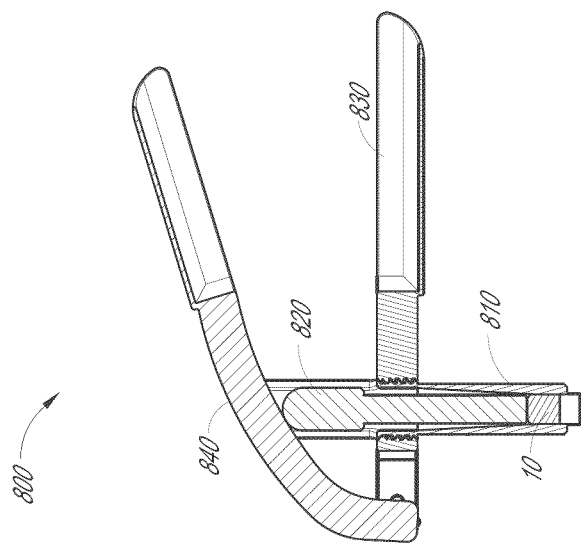
Figure 21A:
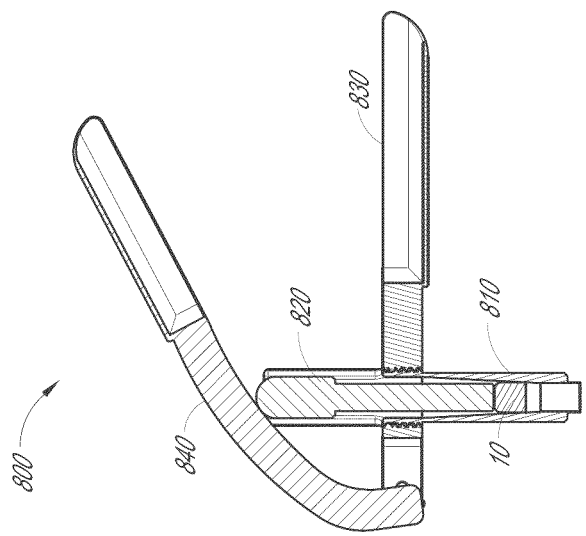

As illustrated in FIGS. 21A-21C, such a movement, in turn, urges the implant 10 distally within the introducer tube 810. As the implant 10 is urged deeper (e.g., more distally) into the interior of the introducer tube 810, the implant 10 may become radially compressed by the interior shape (e.g., tapered portion 816a) of the introducer tube 810. If sufficient force is applied to the implant 10 by moving the clamp relative to the handle, the implant 10 can pass through the neck portion 806 of the introducer tube and into the implant site. In some embodiments, the motion limiter 828 or similar feature of the plunger 820 can contact the distal end of the slit or similar opening 818 of the introducer tube 810 when the implant 10 has been released from the delivery device 800 into the implant site. As depicted in FIG. 21C, this can help prevent the plunger 820 from continuing to move toward and into the implant site and possibly damaging the implant site and/or the implant 10. While the user grasps the handle 830 and the clamp 840 with one hand, he or she can apply a required force on the flange 819 that extends outwardly from the proximal end 802 of the introducer tube 810 with the other hand to stabilize and control the introducer 810.

Accordingly, the mechanically-assisted delivery devices disclosed herein, or equivalents thereof, can facilitate the compression and delivery of reverse tapered implants within a target implant site. In some embodiments, the mechanically-assisted delivery device can be configured to be operated at least partially with the assistance of a mechanical motor, a pneumatic device and/or another external device. For example, the clamp of the device can be moved relative to the handle by or with the assistance of one or more motors (e.g., regulated by a user using a button, knob, dial and/or other controller). Such embodiments can further facilitate the delivery of implants within an implant site of a patient.

In several embodiments, a kit is provided. The kit may include one or more tools for creating a wedge shaped opening or recess, one or more introducers and/or one or more implants. Two, three or more tools may be provided, alone or in combination with two, three or more implants (and/or corresponding introducers). Multiple tools and implants may be provided in a kit to provide flexibility in sizes and shapes.

Although several embodiments and examples are disclosed herein, the present application extends beyond the specifically disclosed embodiments to other alternative embodiments and/or uses of the various inventions and modifications, and/or equivalents thereof. It is also contemplated that various combinations or subcombinations of the specific features and aspects of the embodiments may be made and still fall within the scope of the inventions. Accordingly, various features and aspects of the disclosed embodiments can be combined with or substituted for one another in order to form varying modes of the disclosed inventions. Thus, the scope of the various inventions disclosed herein should not be limited by any particular embodiments described above. While the embodiments disclosed herein are susceptible to various modifications, and alternative forms, specific examples thereof have been shown in the drawings and are described in detail herein. However, the inventions of the present application are not limited to the particular forms or methods disclosed, but, to the contrary, cover all modifications, equivalents, and alternatives falling within the spirit and scope of the various embodiments described and the appended claims. Further, the disclosure herein of any particular feature, aspect, method, property, characteristic, quality, attribute, element and/or the like in connection with an implementation or embodiment can be used in all other implementations or embodiments set forth herein.

In any methods disclosed herein, the acts or operations can be performed in any suitable sequence and are not necessarily limited to any particular disclosed sequence and not be performed in the order recited. Various operations can be described as multiple discrete operations in turn, in a manner that can be helpful in understanding certain embodiments; however, the order of description should not be construed to imply that these operations are order dependent. Additionally, any structures described herein can be embodied as integrated components or as separate components. For purposes of comparing various embodiments, certain aspects and advantages of these embodiments are described. Not necessarily all such aspects or advantages are achieved by any particular embodiment. Thus, for example, embodiments can be carried out in a manner that achieves or optimizes one advantage or group of advantages without necessarily achieving other advantages or groups of advantages.

The methods disclosed herein include certain actions taken by a practitioner; however, they can also include any third-party instruction of those actions, either expressly or by implication. For example, actions such as "creating a recess or opening" or "delivering an implant" include "instructing crating a recess or opening" or "instructing delivering an implant," respectively. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1 mm" includes "1 mm." Phrases preceded by a term such as "substantially" include the recited phrase and should be interpreted based on the circumstances (e.g., as much as reasonably possible under the circumstances). For example, "substantially rigid" includes "rigid," and "substantially parallel" includes "parallel."

What is claimed is:

1. A method of treating a joint of a patient, comprising:

creating a cylindrical recess in a bone located at or near a targeted joint;

wherein the cylindrical recess comprises a surface opening along an outer surface of the bone, a bottom opening along the distal end of the recess and side walls generally extending between the surface opening and the bottom opening;

creating a wedge recess in the bone using a tool by removing additional tissue from the side walls of the cylindrical recess, wherein, once the wedge recess is created, a diameter or other cross-sectional dimension of the bottom opening is larger than a diameter or other cross-sectional dimension of the surface opening, wherein the tool comprises a cutting portion, the cutting portion comprising at least one cutter that is radially expanded by advancing an inner member within the cutting portion, wherein the wedge recess is created by manually rotating the tool so that the cutting portion rotates relative to the bone;

at least partially withdrawing the inner member of the tool from the cutting portion to radially retract the at least one cutter of the cutting portion;

at least partially radially compressing an implant having a wedge shape, the implant comprising a first end and a second end and body extending between the first end and the second end, said second end being generally opposite of said first end, wherein when the implant is in a radially uncompressed state, a diameter or other cross-sectional dimension of the first end is smaller than a diameter or other cross-sectional dimension of the second end;

inserting the implant within the wedge recess while the implant is in a radially compressed state, wherein the second end of the implant is inserted first within the wedge recess, wherein the second end of the implant is adjacent the bottom opening of the wedge recess, and wherein the first end of the implant is adjacent the surface opening of the wedge recess when the implant is properly positioned within the wedge recess; and releasing the implant from a radially compressed state to a less compressed state, when the implant is properly positioned within the wedge recess, wherein, when the implant is in a less compressed state, the diameter or other cross-sectional dimension of the second end of the implant is larger than the diameter or other cross-sectional dimension of the surface opening of the wedge recess.

2. The method of claim 1, wherein when the implant is in a radially uncompressed state, the body of the implant imparts a radial force at least partially along the side walls of the wedge recess, thereby helping to secure the implant within the wedge recess;
   wherein the cylindrical recess is created using a drill bit;
   wherein the at least one cutter is angled relative to a longitudinal axis of the tool when the at least one cutter is radially expanded;
   wherein the at least one cutter comprises at least two cutters; and
   wherein the implant is radially compressed and inserted within the wedge recess using an introducer.

3. The method of claim 1, wherein, when the implant is in a radially uncompressed state, the body of the implant imparts a radial force at least partially along the side walls of the wedge recess, thereby helping to secure the implant within the wedge recess.

4. The method of claim 1, wherein creating a cylindrical recess comprises using a drill bit.

5. The method of claim 1, wherein the at least one cutter is angled relative to a longitudinal axis of the tool when the at least one cutter is radially expanded.

6. The method of claim 1, wherein the at least one cutter comprises at least two cutters.

7. The method of claim 1, wherein the implant is radially compressed and inserted within the wedge recess using an introducer.

8. The method of claim 1, wherein a ratio of the diameter or other cross-sectional dimension of the bottom opening of the wedge recess to the diameter or other cross-sectional dimension of the surface opening of the wedge recess is approximately between 1.05 and 1.3.

9. The method of claim 1, wherein the diameter or other cross-sectional dimension of the bottom opening of the wedge recess is approximately 5% to 25% larger than the diameter or other cross-sectional dimension of the surface opening of the wedge recess.

10. The method of claim 1, wherein the tool is cannulated such that the tool is delivered to a targeted anatomical site over a guide pin.

11. A method of treating a joint of a patient, comprising:
    creating a cylindrical opening within a targeted anatomical site of a subject using a first device;
    removing additional tissue from the sidewalls of the cylindrical opening using a cutting member of a manually-operated tool to create a wedge opening within the targeted anatomical site using a second device, wherein the tool comprises an inner member that is at least partially advanced relative to an outer member to radially expand a cutting portion, the cutting portion comprising at least one cutter,
        wherein, once the wedge opening is created, a diameter or other cross-sectional dimension of a bottom surface of the wedge opening is larger than a diameter or other cross-sectional dimension of a top surface of the wedge opening;
    removing the tool from the wedge opening; and
    inserting an implant into the wedge opening.

12. The method of claim 11, wherein the at least one cutter is angled relative to a longitudinal axis of the tool when the at least one cutter is radially expanded;
    wherein the at least one cutter comprises at least two cutters; and
    wherein the diameter or other cross-sectional dimension of a bottom of the wedge opening is approximately 5% to 25% larger than the diameter or other cross-sectional dimension of a surface opening of the wedge opening.

13. The method of claim 11, wherein the at least one cutter is angled relative to a longitudinal axis of the tool when the at least one cutter is radially expanded.

14. The method of claim 11, wherein the implant is inserted within the wedge opening using an introducer, wherein the introducer radially compresses the implant for delivery into the wedge opening.

15. The method of claim 11, wherein the diameter or other cross-sectional dimension of a bottom of the wedge opening is approximately 5% to 25% larger than the diameter or other cross-sectional dimension of a surface opening of the wedge opening.

* * * * *